United States Patent [19]

Kennefick

[11] Patent Number: 5,826,213
[45] Date of Patent: Oct. 20, 1998

[54] METHOD AND APPARATUS FOR INVESTIGATING TOUGHENING MECHANISMS AND CRACK ADVANCE IN LIGHTWEIGHT MATERIALS

[76] Inventor: Christine Kennefick, 2029 Turtle Pond Dr., Reston, Va. 20191

[21] Appl. No.: 805,466

[22] Filed: Feb. 25, 1997

[51] Int. Cl.$^6$ .................................................. G01N 3/08
[52] U.S. Cl. .................................. 702/35; 73/87; 73/799
[58] Field of Search ............................ 702/35; 73/78–87, 73/785–851

[56] References Cited

U.S. PATENT DOCUMENTS

| | | | |
|---|---|---|---|
| 3,983,745 | 10/1976 | Juusola | 73/789 |
| 4,116,049 | 9/1978 | Barker | 73/87 |
| 4,299,120 | 11/1981 | Barker | 73/87 |
| 4,895,027 | 1/1990 | Manahan, Sr. | 73/799 |
| 5,249,137 | 9/1993 | Wilson et al. | 364/578 |
| 5,278,408 | 1/1994 | Kakibayashi et al. | 250/311 |
| 5,386,507 | 1/1995 | Teig et al. | 345/348 |
| 5,475,218 | 12/1995 | Kakibayashi et al. | 250/311 |
| 5,500,807 | 3/1996 | Lavin et al. | 702/22 |
| 5,602,329 | 2/1997 | Haubensak | 73/82 |

OTHER PUBLICATIONS

P. G. Charalambides, "Anisotropic Aspects and the Analysis of Mixed Mode Delamination Cracking in Fiber Reinforced and Laminated Ceramic Matrix Composites", Industry—University Advanced Materials Conference II, Denver, Colorado, pp. 108–122, Mar. 1989.

Jaroslav Pokluda and Pavel Sandera, "Problem of ideal strength", Metallic Materials, vol. 27, No. 2, Mar. 1989.

Bazant et al, "Random Particle Model for Fracture of Aggregate or Fiber Composites", Journal of Engineering Mechanics, vol. 116, No. 8, pp. 1686–1705, Aug. 1990.

James Dillon Kiely, "Fracture and Toughening Mechanisms of Metal–Ceramic Interfaces", UMI Dissertation Services, A Dissertation in Materials Science and Engineering, 1996.

J.C. Jaeger, Elasticity, Fracture and Flow, 1969, sections 4 and 15.

D. Broeck, Elementary Engineering Fracture Mechanics, 1986, 4$^{th}$ edition, Chapters 3 & 4.

W.H. Press et al., Numerical Recipes in Pascal The Art of Scientific Computing, 1989.

N.I. Muskhelishvilli, Some Basic Problems in the Theory of Elasticity, 2$^{nd}$ edition (English Translation), 1963, Sections 50 & 83a.

*Primary Examiner*—Emanuel Todd Voeltz
*Assistant Examiner*—Demetra R. Smith
*Attorney, Agent, or Firm*—Watson Cole Grindle Watson, P.L.L.C.

[57] ABSTRACT

The system consists of a series of programs that enable a user to investigate possible toughening mechanisms against crack growth in composites and brittle materials consisting of different combinations of materials and containing planar interfaces and elliptically shaped microstructures. The programs begin with various materials, sizes and orientations of microstructures, distances of a crack from a material interface, and possible formulas for energy absorption mechanisms of interest to the user. They then allow a crack to advance toward an interface numerically integrate over a circular and microstructural regions and thus calculate the balance of various energy quantities during crack advance. They then transform the final calculations into a graph display of net energy per incremental length of crack advance versus crack distance from the microstructural entity in question. An advantage of the system is that it allows a user to investigate possible toughening mechanisms against fracture without testing a new specimen each time in a laboratory.

40 Claims, 75 Drawing Sheets

Region of Elastic Energy Release Just Above And Below the Increment of Crack Advance

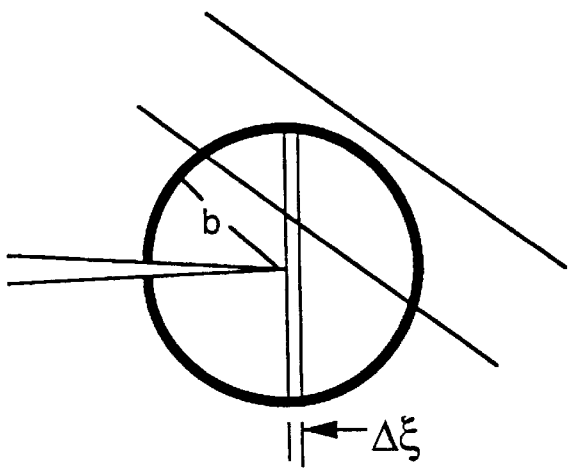
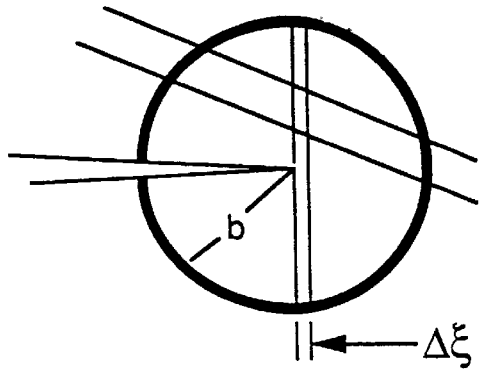
FIG. 9A
FIG. 9B
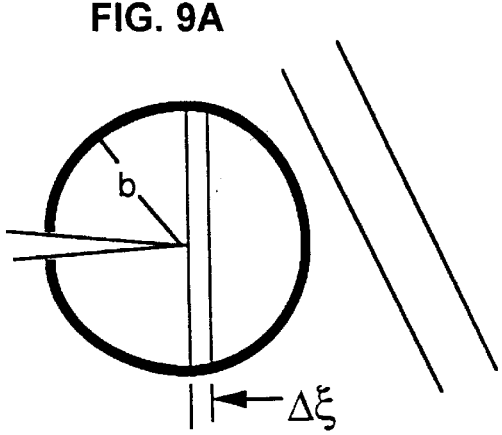
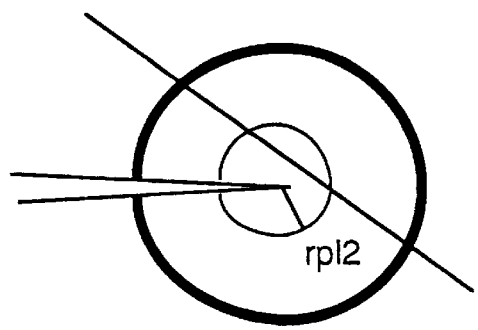
FIG. 9C
FIG. 9D
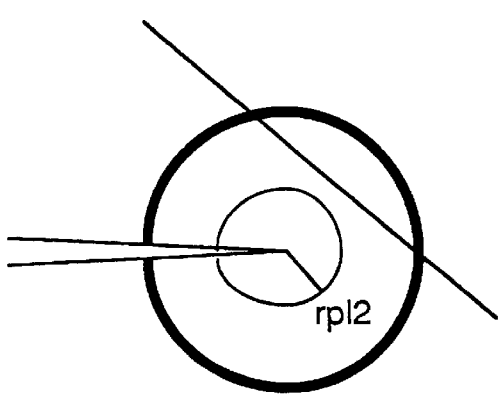
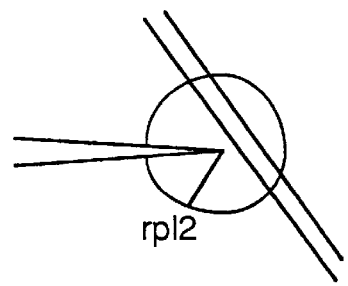
FIG. 9E
FIG. 9F Material 1

Material 2

|                   | PROGRAM 1 | PROGRAM 2 | PROGRAM 3 |
|-------------------|-----------|-----------|-----------|
| CRACK POSITION 1  |           |           |           |
| CRACK POSITION 2  |           |           |           |
| CRACK POSITION 3  |           |           |           |

FIG. 69

Text enclosed by unconnected straight lines denote actions and choices made by the user, such as gathering material data, inserting diskettes or running the next program.

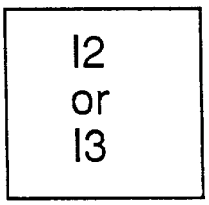

The user keys in the parameter in the square from a question posed directly by a program or keys in information from the inquiry denoted by the symbols within the square. The questions are usually for the geometric setup of the microstructural entity and initial and final positions of the crack.

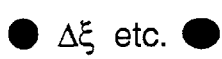

Calculation of a parameter(s) that internally controls the flow of the software

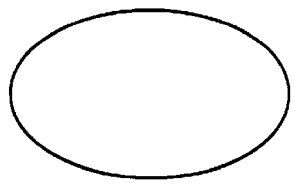

Procedures and calculations

Calculations discontinue for a particular crack position without storage into a datafile in memory because the crack and material setup is covered in another program

Variable or property is assigned in a program outside any dialogue and user input

storage of a result in a position in a datafile in memory

METHOD AND APPARATUS FOR INVESTIGATING TOUGHENING MECHANISMS AND CRACK ADVANCE IN LIGHTWEIGHT MATERIALS

BACKGROUND OF THE INVENTION

1. Field of the Invention

The present invention relates to the study and analysis of materials and in particular to a method and apparatus for studying or investigating the advance or progress of a crack through lightweight materials such ceramic, intermetallic, or metallic materials by determining the relative amounts of energy absorbed or released in a predetermined region as the crack incrementally advances.

2. Discussion of Related Art

There is a growing trend for components and devices to be made of lightweight ceramic, intermetallic, and metallic materials. The term "ceramic" refers to a class of materials primarily based on oxides of metal and on silicon that can withstand very high temperatures, usually have high electrical resistivity and are more resistant to oxidation and corrosion than metals, even at high temperatures. Ceramic used in pottery and cookware are a subset of this group of materials.

Some ceramic compounds have unique thermomechanical, electrostrictive or electrical resistive properties making them useful in, for example, sensors, actuators and electrical capacitors. Ceramic materials are also at the center of superconductor science. Also, due to their relatively low mass and high melting point, ceramic materials can be used in engine parts to increase the fuel efficiency of, for example, automobiles and aircraft.

Despite their advantages, ceramic materials and intermetallics are not used as extensively as expected because they tend to be brittle and thus tend to break or fracture easily. In other words, they are not tough. It is for this reason, for example, that extensive research on manufacturing brittle superconductors in the form of wires and other shapes has gone on.

To improve toughness, materials scientists engage in research on fracture and toughening of ceramic materials. "Toughening" here refers to increasing a material's resistance to fracture in the sense that it takes more energy for a crack in a particular material to move forward than is released in the process. Through plasticity, for example, a crack in a metal must use a lot of energy to move forward. Most metals are, accordingly, not brittle. Thus, the interplay between the energy released and that absorbed as a result of various potential toughening mechanisms as a crack moves forward is one measure of how brittle a materials is.

Although increasing plasticity is one well known technique for improving toughening, there are other less well known techniques that could prove useful in toughening ceramics. Such techniques involve elongating grains and exploiting differences in elastic constants and the angles with which cracks approach interfaces.

At a microscopic level, ceramic materials are comprised of crystallites called "grains". These grains are present even in homogeneous materials. Homogeneous materials are differentiated from composites, which refer to materials made of two or more compounds or are made of a mixture of a metal and a ceramic. An "interface" or bimaterial interface defines a boundary between two materials in a composite. A "particle" or particulate is a piece of one material (often having a size on the order of microns) disposed inside another in a composite. Depending upon the length of its axes, a particle can be, in two dimensions, either circular or elliptical. A long elliptical particle formed of the same material as the matrix surrounding it is referred to herein as an "elongated grain". The presence of elongated grains in ceramic materials generally has resulted in improved toughening properties. In the following discussion, the above mentioned interfaces, i.e., bimaterial and particle/matrix interfaces, will be referred to as "microstructural entities".

Finite element modeling is a known technique used to identify areas of high stress. The technique has been used to calculate other quantifiable properties. However, finite element analysis is not readily adapted to handle bimaterial interfaces and moving crack tips. Indeed, the determination of the number and geometry of the elements at a crack tip or across a bimaterial interface can be formidable. Moreover, running finite element analysis programs typically requires a supercomputer and a minimum of a few months of rigorous training to understand and implement the software to build the requisite models and plot final results.

To overcome the difficulties of using finite element analysis, it has been proposed to use methods that look at the breakage and rearrangement of atoms near the crack tip. These methods, however, have the limitations that the strength and breakage of atomic bonds do not, by themselves, necessarily account for everything in fracture processes, and the models can be limited geometrically in size by the number of atoms a computer can handle. Moreover, the above-described methods tend to be relatively expensive.

Other related art includes methods and apparatus for display and analysis of chemical molecules (U.S. Pat. Nos. 5,386,507, 5,249,137 and 5,500,807) or the display and arrangement of atomic defects in connection with images seen under a transmission microscope to identify atomic species causing leakage and poor resistance in ULSI devices (U.S. Pat. Nos. 5,278,408 and 5,475,218).

The following references give an overview of the state of the art. The disclosures of all of these references are hereby incorporated by reference into the present disclosure. The publications other than U.S. patents will be cited in the specification by numerals in parentheses, e.g., (1).

U.S. Patents:

| | | |
|---|---|---|
| 5,249,137 | 9/1993 | Wilson et. al. |
| 5,278,408 | 1/1994 | Kakibayashi et. al. |
| 5,386,507 | 1/1995 | Teig et. al. |
| 5,475,218 | 12/1995 | Kakibayashi et. al. |
| 5,500,807 | 3/1996 | Lavin et. al. |

Other Publications:

1. J. C. Jaeger, *Elasticity, Fracture and Flow*, Chapman and Hall, 1969, sections 4 and 15.
2. D. Broek, *Elementary Engineering Fracture Mechanics*, Martinus Nijhoff Publishers, 4th edition, 1986, chapters 3 and 4.
3. W. H. Press, B. P. Flannery, S. A. Teukolsky and W. T Vetterling, *Numerical Recipes in Pascal The Art of Scientific Computing*, Cambridge University Press, 1989.
4. N. I. Muskhelishvilli, Some Basic Problems in the *Theory of Elasticity*, 2nd edition (English Translation), 1963, sections 50 and 83a.

SUMMARY OF THE INVENTION

It is therefore an object of the present invention to provide a method and apparatus for simulating and modeling the advancement of a crack in various materials which can be implemented on a personal computer and which is inexpensive and relatively simple to implement.

It is a further object of the present invention to provide such a method and apparatus which can simulate and model the interplay between the energy released and that absorbed in a predetermined region as a result of testing various potential toughening mechanisms as a crack moves forward.

It is a further object of the present invention to provide a modeling system that accounts for the advancement of a crack toward a bimetallic interface or elliptical particle interface.

It is yet a further object of the present invention to provide a modeling system that does not rely on finite element analysis or atomic bonding properties.

It is yet a further object of the present invention to enable a user to change desired formulas and laws easily in the programs without having to reproduce an experimental setup geometrically inside the programs or test a new experimental sample immediately in a laboratory.

Other objects of the invention will become apparent to those skilled in the art upon study of the detailed description of the invention set forth later herein.

In an exemplary embodiment, the present invention comprises a method and apparatus for modeling the advancement of a crack by defining a circular region around the crack tip for plasticity and another circular region for elastic energy release. The crack is then incrementally "advanced" or "moved forward." It is then determined where the aforementioned circular regions overlap with the material interfaces and particles and the total energy is calculated by a sum of energy terms that are numerically integrated over the relevant overlapping areas for each increment of crack advance. The results are then internally plotted and can thereafter be viewed.

The method supports modeling with straight planar interfaces as well as elliptical particles. A choice of angle between the interface or particle with respect to the crack tip can also be chosen for the analysis. Finally, the angle of the crack with respect to an applied load can be specified and accounted for in the present invention.

The present invention, unlike the prior art described above, does not display or replicate a microscopic image or a molecule for analysis, but offers a method in which to investigate possible toughening mechanisms against crack growth in lightweight but often brittle materials with a proposed microstructure by having a crack "advance" toward the proposed microstructure. The method of allowing a crack to advance toward a proposed microstructure, recognizing where the crack tip is and numerically integrating various energy quantities over relevant areas means that the present invention is not limited to studying individual atoms and molecules, but also enables a user to evaluate toughening mechanisms defined on a per unit area or per unit volume basis that can be at either an atomic or a continuum level.

The method of the present invention operates at a much larger scale than an atomic bond analysis, needs no finite elements, and can be implemented on an IBM-compatible PC, even an XT-class machine.

The invention enables a user to specify and experiment with different toughening mechanisms without having to manufacture a new experimental specimen each time.

The technique involves no lattices, meshes or drawing of models or specimens on a screen. Scaling up for three dimensions, for example, requires only the addition of a loop of counting an integer where necessary to perform numerical integration in the third dimension.

In particular, the present invention comprises a series of operational steps to be performed by means of a computing device including a processor, means for receiving input from a user, and output means for displaying an output to the user. The series of operational steps comprises: (a) prompting the user, with the output means, for information regarding a material having a crack therein; (b) receiving the information from the user with the input means; (c) selecting an increment of crack advance; and (d) in accordance with the information received in step (b) and the increment of crack advance selected in step (c), integrating numerically by means of the processor over a region surrounding a tip of the crack to determine an energy change in the region caused by an advance of the crack by the increment of crack advance selected in step (c).

The present invention further contemplates a computing device comprising a processor, means for receiving input from a user, and output means for displaying an output to the user. The processor comprises means for controlling the computing device to perform the operational steps: (a) prompting the user, with the output means, for information regarding a material having a crack therein; (b) receiving the information from the user with the input means; (c) selecting an increment of crack advance; and (d) in accordance with the information received in step (b) and the increment of crack advance selected in step (c), integrating numerically by means of the processor over a region surrounding a tip of the crack to determine an energy change in the region caused by an advance of the crack by the increment of crack advance selected in step (c). The output means can be one or more of a video display, a printer, and other output devices capable of being used with computing devices.

According to another aspect, the present invention contemplates a computing device comprising: a processor; input means for receiving input from a user; and output means for displaying an output to the user; the processor comprising: means for prompting the user, with the output means, for information regarding a material having a crack therein; means for receiving the information from the user with the input means; means for selecting an increment of crack advance; and means for integrating numerically over a region surrounding a tip of the crack in accordance with the information and the selected increment of crack advance to determine an energy change in the region caused by an advance of the crack by the increment of crack advance.

The present invention further contemplates two series of operational steps to be performed on or by means of a computing device, the series of operational steps being useful to determine limits of numerical integration used in the invention. The first is preferably used in cases in which the microstructural entity has planar sides and comprises the steps of (a) prompting the user, by means of the output, to enter data comprising material characteristics of portions of the material within the first and second material regions, a thickness d of the second material region, a distance $\xi$ of the crack tip to the first boundary along a crack path, a radius b around the crack tip in which energy release caused by the crack is to be calculated, and an angle $\psi$ representing an orientation of the crack path with respect to the first boundary; (b) receiving the data from the user by means of the input; (c) calculating, in accordance with the data received in step (b), a shortest distance r1 from the crack tip to the first boundary and a shortest distance r2 from the crack tip to the second boundary; (d) calculating, in accordance with the material characteristics received in step (b), a radius of plasticity rpl1 of the portion of the material within the first material region and a radius of plasticity rpl2 of the portion of the material within the second material region, wherein the radii b, rpl1, and rpl2 define the at least one region of integration; (e) determining whether b<r1 or b>r1; (f) if b<r1, determining whether r1<rpl2 or r1>rpl2; (g) if b>r1, determining whether r2<rpl2 or r2>rpl2; and (h) determining the spatial relationship in accordance with results of the determining steps in steps (e)–(g).

The second series of operational steps is useful in the case of an elliptical microstructural entity and includes the steps of (a) dividing the ellipse into a plurality of regions, each of the regions being defined by four values boundleft, boundright, boundlower, and boundupper such that said each of the regions of the ellipse consists of points whose x coordinates lie between boundleft and boundright and whose y coordinates lie between boundlower and boundupper; (b) determining, by numerical approximation, a numerically approximated intersection point between the ellipse and said another curve, the numerically approximated intersection point having coordinates NRx and Nry; and (c) for each one of the plurality of regions: (i) determining whether boundleft$\leq$NRX$\leq$boundright; (ii) determining whether boundlower$\leq$NRy$\leq$boundupper; (iii) if both of determining steps (c)(i) and (c)(ii) yield affirmative answers, locating the intersection point within that one of the plurality of regions and assigning NRx and NRy as coordinates of the intersection point; and (iv) if at least one of determining steps (c)(i) and (c)(ii) yields a negative answer, determining that the intersection point lies outside that one of the plurality of regions; so that the intersection point is uniquely located in only one of the plurality of regions.

BRIEF DESCRIPTION OF THE DRAWINGS

The present invention will be described in detail with reference to the drawings, in which:

FIGS. 9A–9F show positions of radii of plasticity and elasticity with respect to a second material with planar sides used to set the value of a parameter finalflag;

FIG. 69 is a key for symbols used in the flow charts of FIGS. 25–66.

DESCRIPTION OF THE INVENTION

The detailed description of the invention will be organized in the following manner. First, an illustrative example will be given which should suffice to impart to those skilled in the art an understanding of the present invention. Second, specific implementations will be described in greater detail for those wishing an even deeper understanding of the present invention in practice.

Figure 1A:
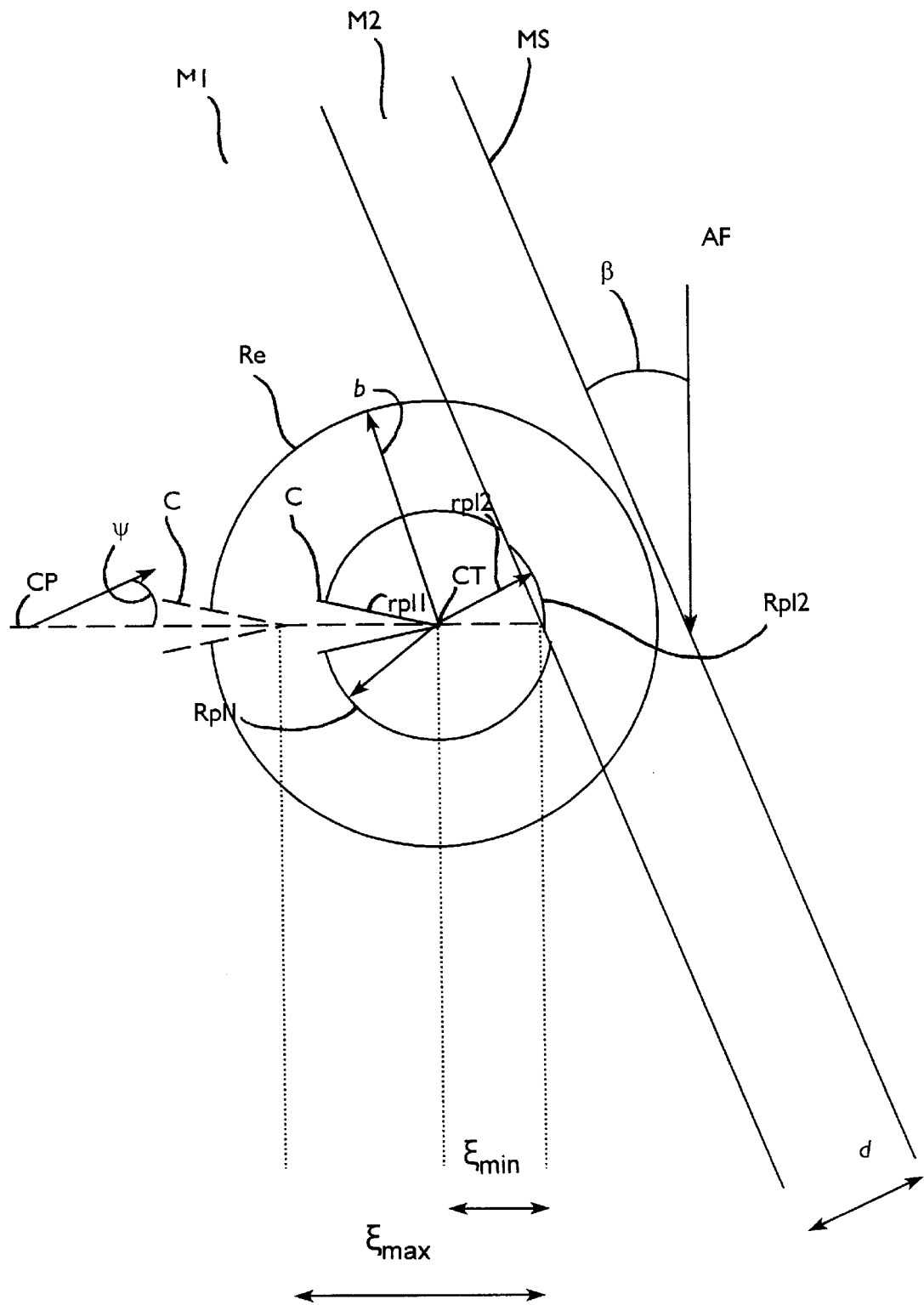
FIG. 1A shows a geometrical configuration of a material having a microstructural entity and a crack advancing toward that microstructural entity.

FIG. 1A shows the geometry used to calculate energy release during crack advance. The material has first material region M1 and second material region M2, the latter being defined by microstructure MS having thickness d. The second material region may include the same material as the first material region, a different material, or a void. The material is subject to an applied force along line AF which forms angle β with microstructure MS. The fraction of the second material region in the entire material, measured along a line perpendicular to AF, is f. Crack C having crack tip CT advances toward the microstructure along crack path CP which forms angle ψ with the microstructure. The crack tip has a displacement ξ from the microstructure which has minimum value $\xi_{min}$ (shown for crack tip CT) and maximum value $\xi_{max}$. The total initial crack length is a. The configuration shown for the microstructure is the simplest one considered, namely, one with two planar sides that are taken to have infinite extent for simplicity of calculation. Other configurations, namely, granules that can be approximated as ellipses, will be considered later.

The following regions are defined around the crack tip. Region Re of user-selected radius b is a region in which energy release is to be calculated. Region Rpl1 having radius rpl1, which is defined in terms of the physical characteristics of first material M1, is a first region of plasticity in which the first material absorbs energy released by advance of the crack. Region Rpl2 having radius rpl2 is defined in the same way with reference to second material M2; such a region may or may not exist, depending on the geometry and the physical characteristics of second material M2.

Figure 1B:
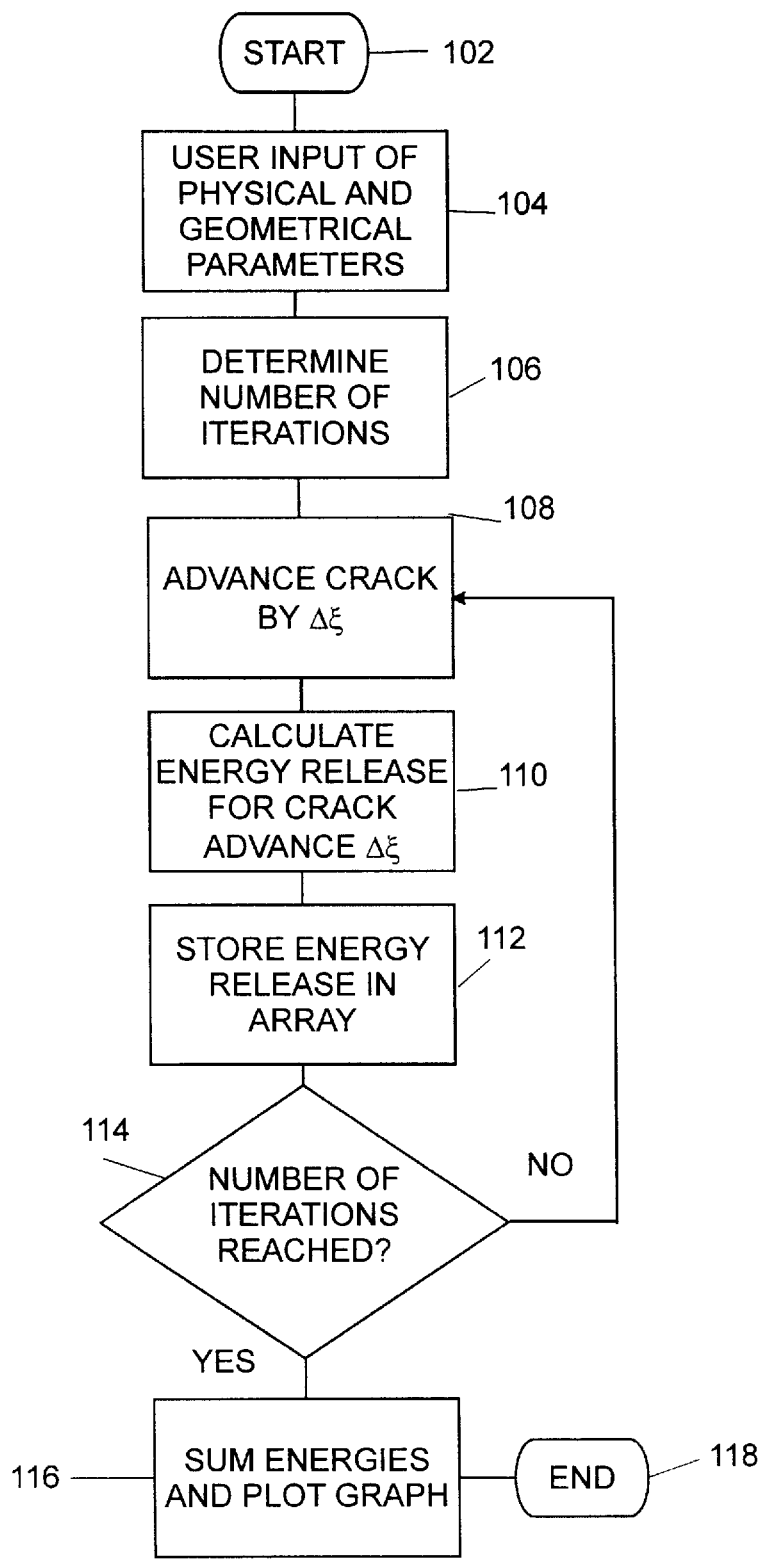
FIG. 1B is a flow chart showing a series of operational steps for computing energy release by advance of the crack of FIG. 1A.

In its simplest form, the process operates as shown in FIG. 1B. The process starts in step 102. In step 104, the computer either prompts the user for an input of physical and geometrical parameters or allows such an input by a change of assignment statements. The physical parameters are those needed to calculate energy release in the two material regions; as known to those skilled in the art, such physical parameters include a, the Young's moduli, shear moduli, Poisson's ratios, and yield strengths for the materials in the two material regions. The geometrical parameters include b, d, f, $\xi_{max}$, $\xi_{min}$, β, and ψ.

Once the physical and geometrical parameters are received, the number i of iterations is determined in step 106. This number is determined in accordance with $\xi_{max} - \xi_{min}$, which is the length traveled by the crack tip during the simulation, and can be derived, e.g., via a lookup table. Once the number of iterations is determined, an interval of crack advance Δξ is defined as $(\xi_{max} - \xi_{min})/i$. The relationship between $\xi_{max} - \xi_{min}$ and i, and thus between $\xi_{max} - \xi_{min}$ and Δξ, can be varied in accordance with the scale (atomic or larger) at which the user wishes to examine the processes occurring during crack advance.

In step 108, the crack is advanced by Δξ, and in step 110, the energy release caused by such a crack advance is calculated. The manner of calculation in step 110 will be explained below. In step 112, the energy release calculated in step 110 is stored in memory in an array having at least one dimension corresponding to the degree of crack advance (number of iterations up to that calculation). In step 114, it is determined whether the total number i of iterations has been reached; if not, the process returns to step 108. If the total number of iterations has been reached, the process proceeds to step 116, in which the values stored in the array are summed to obtain a total energy release, and the individual values are used to plot a graph of energy release as a function of crack advance. The energies are preferably stored separately in the array rather than simply summed as the process goes along so that such a graph can be made. The process ends in step 118.

Radius b is selected by the user in accordance with the scale (atomic or larger) on which the user wishes to investigate the physical processes occurring in the material during crack advance. This radius is typically 100 μm.

The specifics of calculation of the energy release depend on the materials, which may absorb the energy through plasticity or another mechanism. Those skilled in the art will be familiar with such mechanisms, e.g., through references (1), (2), and (4) cited above. The mechanism for each material will be represented by some value per unit area or per unit volume.

Figure 1C:
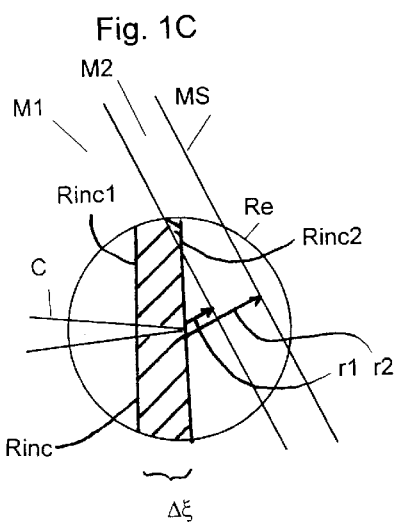
FIGS. 1C–1E show variations of the geometrical configuration of FIG. 1A.

For each crack advance, the elastic energy release, for example, can be calculated in a region of width Δξ extending up and down (perpendicularly to the crack path CP) from the crack advance. A simplest case is shown in FIG. 1C, where microstructure MS has planar sides and the energy release is calculated in region Re of radius b. For each increment, the energy release is calculated within incremental region Rinc of width Δξ bounded by the circle of radius b which defines the edge of region Re. The exact shape of Rinc varies with the type of energy absorbing mechanism occurring in each material and may extend beyond the width shown in FIG. 1C. Because this incremental region Rinc can extend into both first material region M1 and second material region M2, it can contain two incremental regions Rinc1 and Rinc2 within the two material regions. Of course, within each of these two incremental regions, the energy release must be calculated in the manner appropriate for the first or second material.

Figure 1D:
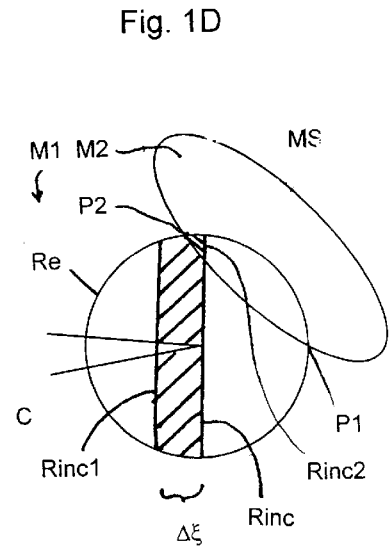

A more complicated situation is shown in FIG. 1D. Here, microstructure MS is bounded by an ellipse which intersects with the edge of region Re at points P1 and P2. Depending on the geometry of the particular crack advance and in particular on the geometrical relation between the increment of crack advance and points P1 and P2, Rinc may have only one region or two and may end at the edge of Re at both ends or at the edges of Re and MS. Even more complex configurations will be considered; for example, FIG. 1E shows a case in which the circle bounding Re and the ellipse bounding MS have four points of intersection P1, P2, P3, and P4.

Figure 1E:
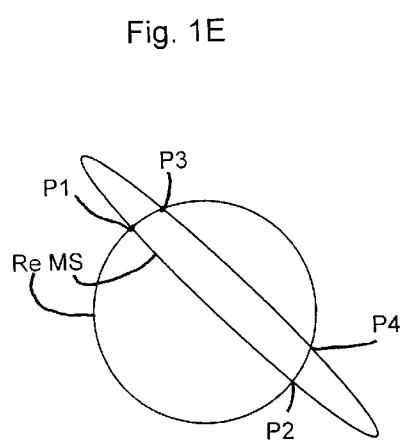

It will be seen from FIGS. 1C–1E that a numerical integration requires a determination of the spatial relationship among the various regions. The series of operational steps shown in FIGS. 1F and 1G are used to perform this determination.

Figure 1H:
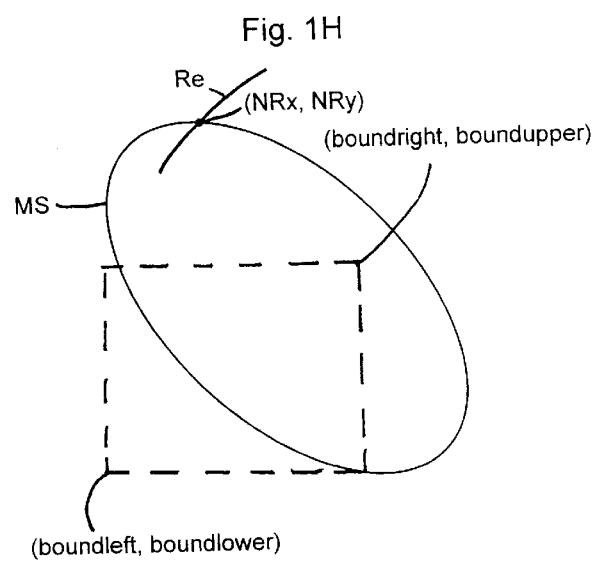
FIG. 1H shows a region of an ellipse used in the series of operational steps of FIG. 1G.
Figure 1F:
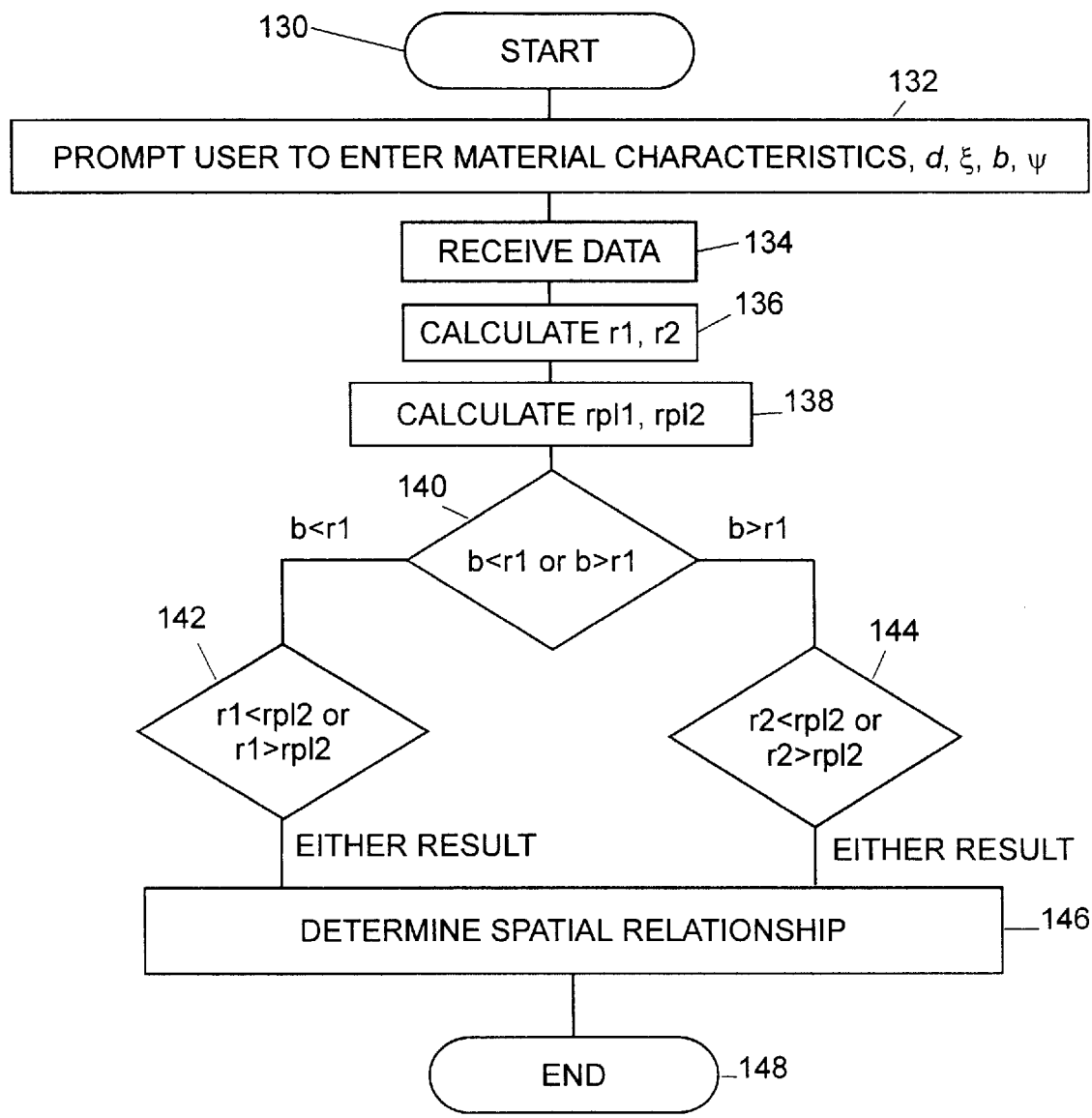
FIGS. 1F and 1G are flow charts showing series of operational steps used to determine limits of integration in the variations of FIGS. 1C–1E.

The first such series of operational steps, shown in FIG. 1F, is intended primarily for use in a situation in which the microstructure has planar sides, as shown in FIG. 1C, and starts in step 130. In step 132, the user is prompted to enter data comprising the material characteristics of portions of the material within the first and second material regions, d, $\xi$, and $\psi$. These data are received in the computing device in step 134. In step 136, the computing device calculates, in accordance with the data received in step 134, a shortest distance r1 from the crack tip to the first boundary and a shortest distance r2 from the crack tip to the second boundary. Distances r1 and r2 are shown in FIG. 1C. In step 138, the computing device calculates, in accordance with the material characteristics received in step 134, radii of plasticity rpl1 and rpl2; the radii b, rpl1, and rpl2 define at least one region of integration. In step 140, it is determined whether b<r1 or b>r1. If b<r1, it is determined in step 142 whether r1<rpl2 or r1>rpl2. If b>r1, it is determined in step 144 whether r2<rpl2 or r2>rpl2. In step 146, the spatial relationship is determined in accordance with results of the determining steps in steps 140–144. The series of operational steps ends in step 148.

Figure 1G:
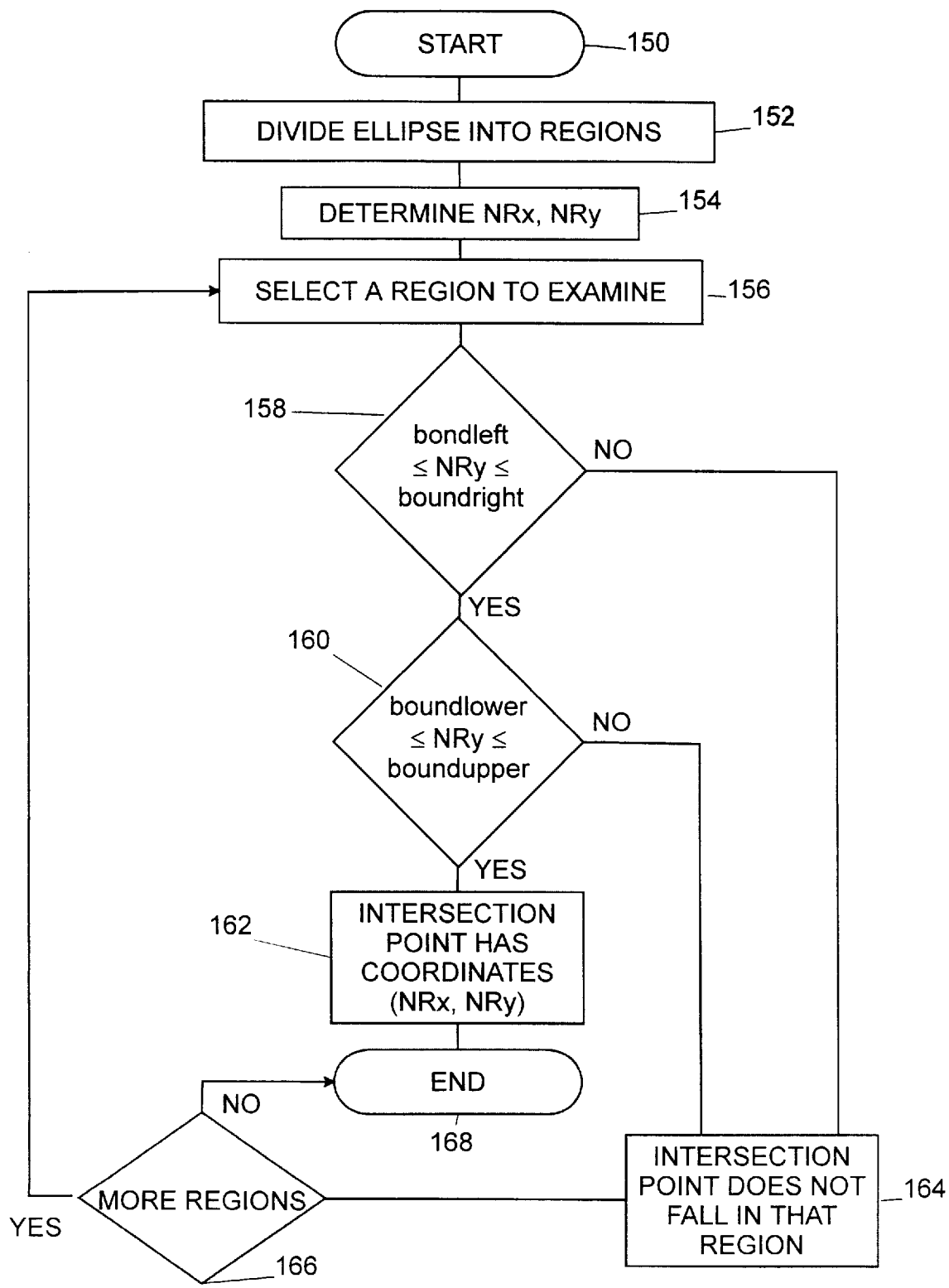

The second series of operational steps, shown in FIG. 1G, is intended primarily for a situation in which the microstructure is elliptical, as shown in FIGS. 1D and 1E, and starts with step 150. In step 152, the ellipse is divided into a plurality of regions, each of the regions being defined by four values boundleft, boundright, boundlower, and boundupper such that said each of the regions of the ellipse consists of points whose x coordinates lie between boundleft and boundright and whose y coordinates lie between boundlower and boundupper. Such a region is shown in FIG. 1H. In step 154, a numerically approximated intersection point is determined by numerical approximation, e.g., by a Newton-Raphson routine, between the ellipse and a region of integration (Re, Rpl1, Rpl2), the numerically approximated intersection point having coordinates NRx and Nry. Such an intersection point is shown in FIG. 1H. A region to examine is selected in step 156. For this region, it is determined (i) whether boundleft$\leq$NRx$\leq$boundright in step 158 and (ii) whether boundlower$\leq$NRy$\leq$boundupper in step 160. If both of determining steps 158 and 160 yield affirmative answers, the intersection point is located in step 162 within that one of the plurality of regions, and NRx and NRy are assigned as coordinates of the intersection point. If at least one of determining steps 158 and 160 yields a negative answer, it is determined in step 164 that the intersection point lies outside that one of the plurality of regions. If so, and if there are more regions as determined in step 166, another region is checked, beginning with step 156. Eventually, the intersection point is uniquely located in only one of the plurality of regions, and the process ends in step 168.

Those skilled in the art who have reviewed the above description should readily understand the invention. However, for those who wish a more detailed description of various embodiments, the following description is provided. This latter description makes reference to the following quantities:

b—radius within which elastic strain energy is calculated boundleft—a limiting boundary on the left of one of the regions used to find intersection points between a circle and an ellipse boundlower—a limiting boundary on the lower side of one of the regions used to find intersection points between a circle and an ellipse boundright—a limiting boundary on the right of one of the regions used to find intersection points between a circle and an ellipse boundupper—a limiting boundary on the upper side of one of the regions used to find intersection points between a circle and an ellipse c—vertical distance between the x2, y2 and x1, y1 coordinate systems cmax—a maximum value for c to ensure that an elliptically shaped entity intersects the crack path cmin—a minimum value for c to ensure that an elliptical entity depending upon the geometrical setup either does or does not intersect the crack path crprop—a collection of quantities for propagation related to the angular setup and initial crack length such as $\xi$, actual crack length, stress intensity factors and plastic radii d—thickness of a planar strip of the second material ed—energy densities EDiff—Total sum of desired energy terms for a particular crack position divided by $\Delta\xi$ ele(b)—total elastic energy in the circular area of radius b eleterm—total elastic energy term for a particular $\xi$ for the geometric region at hand f1—an intermediate flag in assigning finalflag that gets a 0 or 1 depending upon the lengths of r1 and r2 in comparison with the radius of elasticity b f2—an intermediate flag in assigning finalflag that gets a 0 or 1 depending upon the lengths of r1 and r2 in comparison with the radius of plasticity in material 2 firstpt—one abscissa in a pair of intersection points to be tested for the number integrations g—horizontal distance between the x2, y2 and x1, y1 coordinate systems hmin—final minimum distance of the crack tip from the center of the elliptical microstructural entity hmintest—a minimum distance for the closest distance of the crack tip from the center of the elliptical entity specified by the user to ensure that the entity does not intersect the crack path hmax—initial remote distance of the crack tip from the center of the elliptically shaped microstructural entity hmaxtest—a minimum distance for the furthest distance of the crack tip from the center of the elliptical entity specified by the user to ensure that the entity does not intersect the crack path I1, I2 and I3—inquiries for the geometrical setup of the crack and microstructural entity integrands(r)—integrand terms that are already the result of integration with respect to r and are ready for integration with respect to $\theta$.

IntResult—result of numerical integration j—length of the minor axis of an elliptically shaped microstructural entity k—length of the major axis of an elliptically shaped microstructural entity I1 to I6—limits of integration for y2 in the x2, y2 coordinates of the regions for numerical integration in the areas just in front of the crack limits left and right—integration limits for x'.

m—parameter measuring the eccentricity of the ellipse.

mode I—mode I crack propagation mode II—mode II crack propagation

NRx—an abscissa of an intersection point between a circle and the ellipse found by a Newton-Raphson method on the two equations for the circle and ellipse.

NRy—an ordinate of an intersection point between a circle and the ellipse found by a Newton-Raphson method on the two equations for the circle and ellipse.

ord1—ordinate on the lower side of the microstructural entity for a given x2 abscissa in the x2, y2 coordinate system.

ord2—ordinate on the upper side of the microstructural entity for a given x2 abscissa in the x2, y2 coordinate system.

pIwA1—plastic work per unit area in material 1 pIwA2—plastic work per unit area in material 2 pt1$i$x—abscissa of an endpoint of integration when only one integration is required pt2$i$x—abscissa of an endpoint of integration when two integrations are required pt3$i$x—abscissa of an endpoint of integration when three integrations are required r—radial coordinate in the r,θ coordinate system local to the crack tip R—radial parameter measuring the size of the ellipse if its eccentricity m were zero r1—distance from the crack tip to the edge of the microstructural entity at x2=Δξ that has the lower ordinate y2 in the x2, y2 coordinate system r2—distance from the crack tip to the edge of the microstructural entity at x2=Δξ that has the upper ordinate y2 in the x2, y2 coordinate system Result(i)—final energy terms stored in datafiles corresponding to the $i^{th}$ position of the crack.

sdpI—shortest distance between the crack tip and the second material when the second material is planar.

secondpt—a second abscissa in a pair of intersection points to be tested for the number of integrations.

str—stress quantities strprop—variables related to the assignment of stress and stress intensity factors such as initial crack length, applied stress and modification parameters due to a bimaterial interface test1, test2, test1$a$, test1$b$, test2$a$, test2$b$, test3$a$, test3$b$, test4—test variables used to get the number of integrations correct.

trialxreg—a trial abscissa for one of the regions 1$a$ to 4$b$ in Drawing 18 that gets either a value of 0 or the value of an actual abscissa obtained from a Newton-Raphson routine if the actual abscissa falls into that region along with its corresponding ordinate.

trialyreg—a trial ordinate for one of the regions 1$a$ to 4$b$ in Drawing 18 that gets either a value of 0 or the value of an actual ordinate obtained from a Newton-Raphson routine if the actual ordinate falls into that region along with its corresponding abscissa.

x'—horizontal coordinate in a local x', y' coordinate system for the ellipse x1—horizontal coordinate in a local x1, y1 coordinate system for the ellipse when it is not rotated with respect to the line parallel to the applied load x2—horizontal coordinate in the x2, y2 coordinate system local to the crack tip y'—vertical coordinate in a local x', y' coordinate system for the ellipse y1—vertical coordinate in a local x1, y1 coordinate system for the ellipse when it is not rotated with respect to the line parallel to the applied load y2—vertical coordinate in the x2, y2 coordinate system local to the crack tip α—an angle measure in the counterclockwise direction between the major axis of the ellipse and the remote applied tensile stress.

β—angle the microstructural entity makes with the applied load

γ—an angle between the r and σ directions

η—angular coordinate in an elliptical coordinate system for the ellipse

θ—angular coordinate in the r, θ coordinate system local to the crack tip

ξ—distance of the crack tip from the microstructural entity measured along the crack path ψ—angle the crack makes with the perpendicular to the applied load I. Fracture Toughening and Microstructural Entities (FIGS. 2A, 2B, 3–6, 7A and 7B)

As used herein, the term "toughening" refers to resistance to fracture in the sense that it takes more energy for a crack to move forward than is released in the process.

The term "applied stress" is the load per unit area applied to a material remote from the crack and microstructural entity that is present throughout the material including the region containing the crack and microstructural entity. An applied stress becomes concentrated or increased in the vicinity of a crack tip, and this increase is measured by the stress intensity factor. The resulting increased amount of elastic strain energy around a crack tip is energy that can be released as a crack moves forward, thus making it energetically favorable for a crack to move forward and release the load on the open crack surfaces behind it.

Toughening described herein also refers to two basic mechanisms that could counteract the energy release as a crack moves forward. One is plasticity or some other process that requires an absorption of energy in one of the circular regions encompassing the crack tip in FIG. 2B. The other is some process or microstructure that locally produces stresses that counteract the concentrated tensile and shear stresses around the crack tip itself, thus modifying the stress field for potential energy release or producing a stress field which the crack must overcome to move forward. This second mechanism will be referred to as a "modification of a stress field".

Figure 2A:
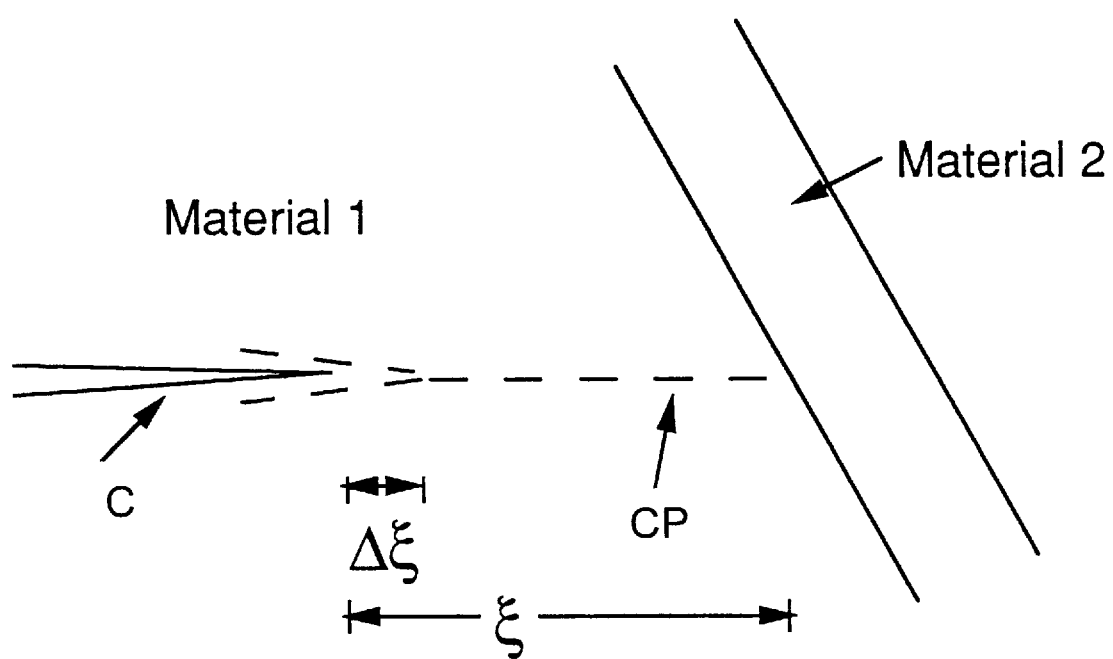
FIG. 2A shows a crack advance in a material.

The term "increment of crack advance" refers to one incremental length of advance in a program loop between the initial and final distances selected by the user and is labeled Δξ in FIG. 2A.

Figure 3:
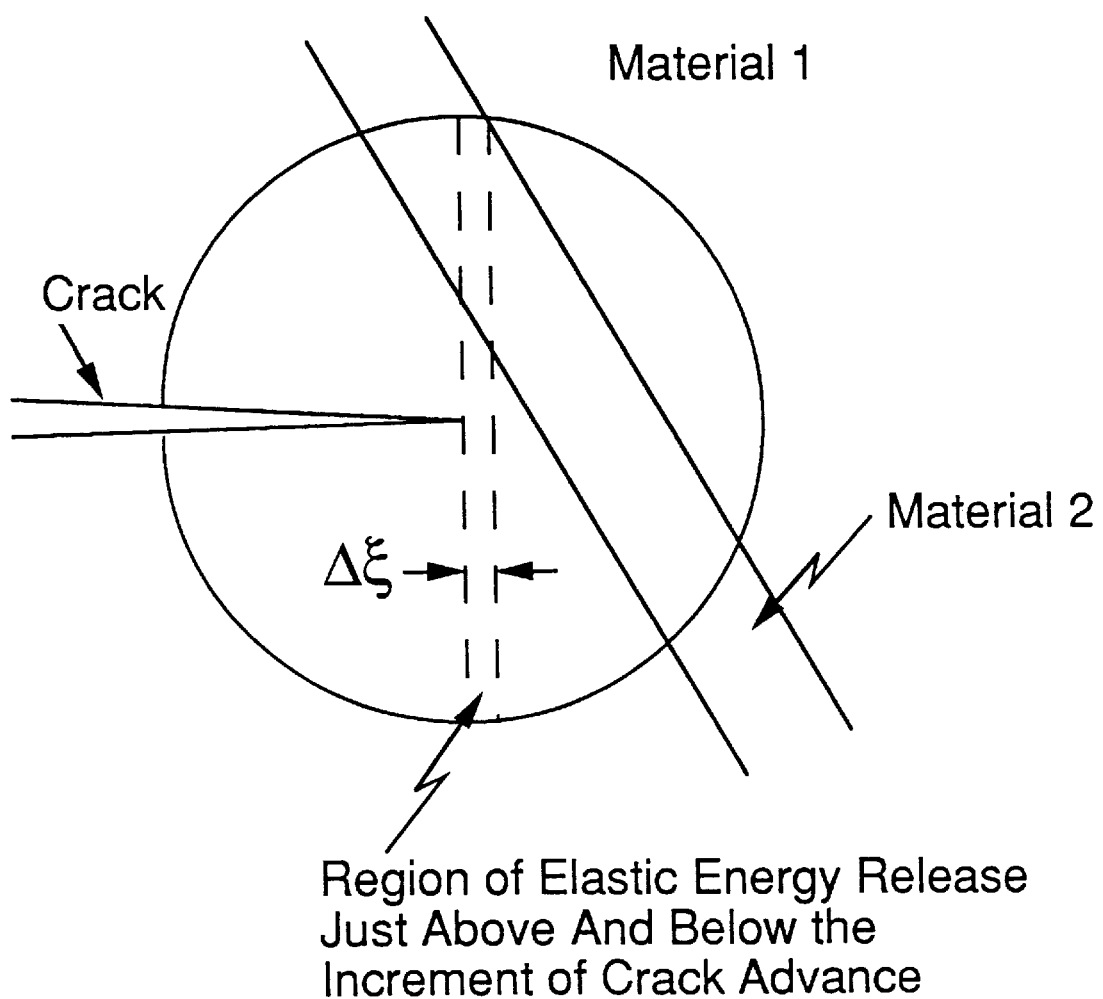
FIG. 3 shows a region of strain energy release just above and below the increment of crack advance where the material is unloaded.
Figure 4:
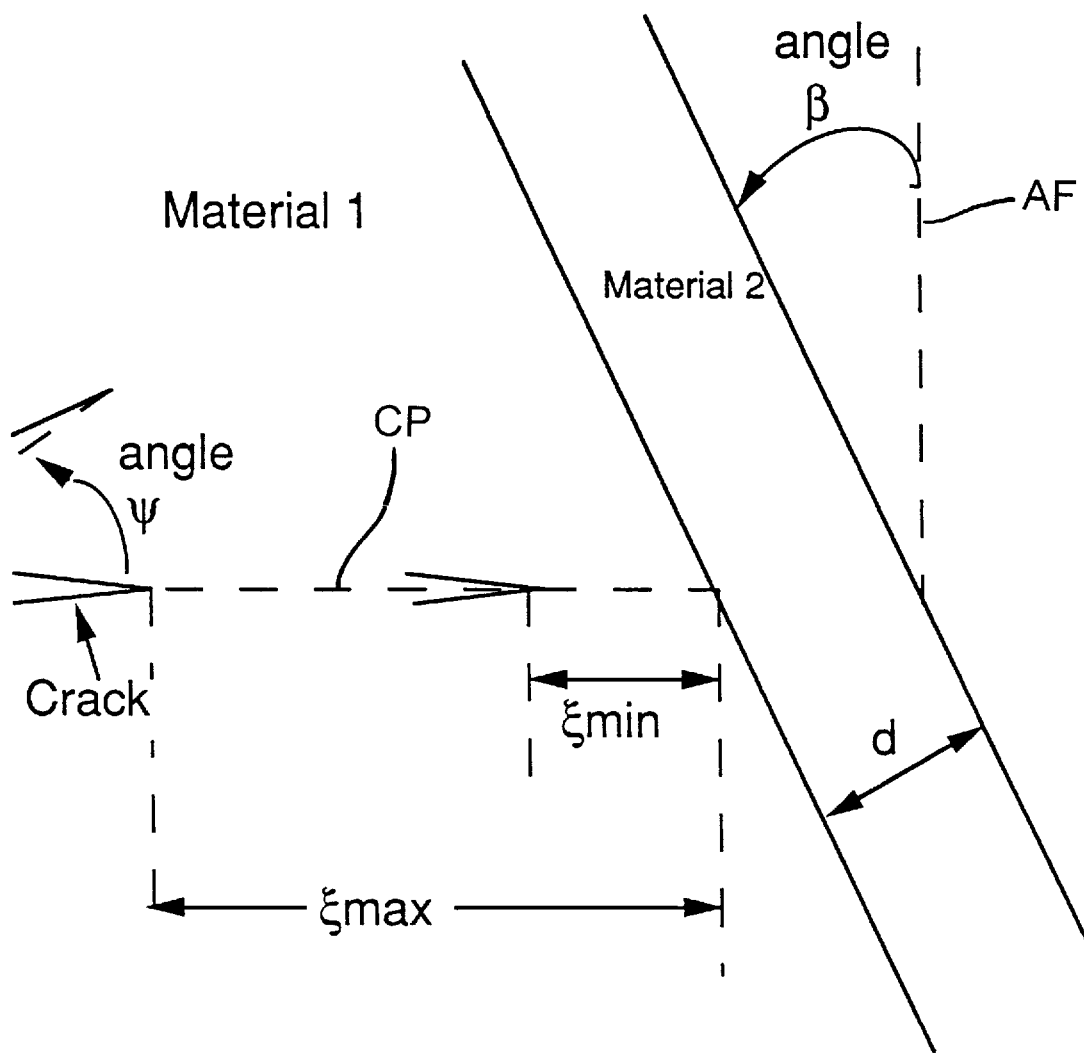
FIG. 4 shows a crack approaching an interface with planar sides.

The term "microstructural entity" refers to either a region of material finite or infinite in width with planar sides, as in FIGS. 3 and 4, or an elliptically shaped particle or grain shown in FIGS. 5, 6, 7A and 7B.

In the method and computer system described herein, the calculations used to set up the microstructural entities and toughening mechanism are analytical in the sense that they are calculated directly by numerical variables, equations and numerical integration. An elliptically shaped entity can therefore become a circularly shaped entity if the user specifies that the major and minor axes are the same or that its eccentricity m is zero. Alternatively, the major axis of the ellipse can be substantially elongated to represent a needle-like microstructure.

In modifying a stress field, the stresses are also calculated analytically. This gives the user the alternative of allowing either the planar or elliptically shaped entity to be a pore, hole, crack or void with a stress field in a possible compound or microstructure around it contributing to toughening.

The term "material 1" refers to the region outside the microstructural entity that contains the crack. The term "material 2" refers to the region within the microstructural entity and can be a completely different material from material 1 with different elastic constants. The analytical calculations in the programs also allow "material 2" to be a different phase or compound of material 1, a grain of material 1 itself, or a region of open space such as a pore or crack.

II. Definition and Preparation of Basic Data

IIA. Introduction

There are two kinds of inputs and data that the programs use to analyze the crack advance. Some inputs are geometric that allow the selection of the orientation of the microstructure and the initial and final positions of the crack. Others are material properties such as elastic constants found in handbooks and in literature that allow the user to select whether the system containing the crack will include one material or two, and if two, which two materials.

An initial crack length can also be set by the user. The actual crack length is calculated inside the programs as the crack advances. Material and crack properties such as radii of plasticity and stress intensity factors that depend upon crack length are therefore calculated and prepared further inside the programs when the crack length changes.

IIB. Basic Geometric Parameters (FIGS. 2A, 2B, 3–6, 7A, 7B, 8 and 35–37)

IIB.1 Geometrical Parameters Common to All Programs (FIGS. 2A, 4, 5, 6, 7A and 7B)

There are two angles common to all programs that the user keys in at the beginning. One is the angle $\beta$, which has units in degrees and which measures the angle of tilt of the microstructural entity with respect to the applied load, as shown along the vertical dotted line marked AF in FIGS. 4, 5 and 6. When the microstructural entity is planar, the angle $\beta$ is measured between the line of the applied load AL and a line parallel to the sides of the entity (FIG. 4). When the microstructural entity is elliptically shaped, the angle $\beta$ is measured between the line of the applied load AL and the line coinciding with the major axis of the ellipse of length k (FIGS. 5 and 6).

Figure 5:
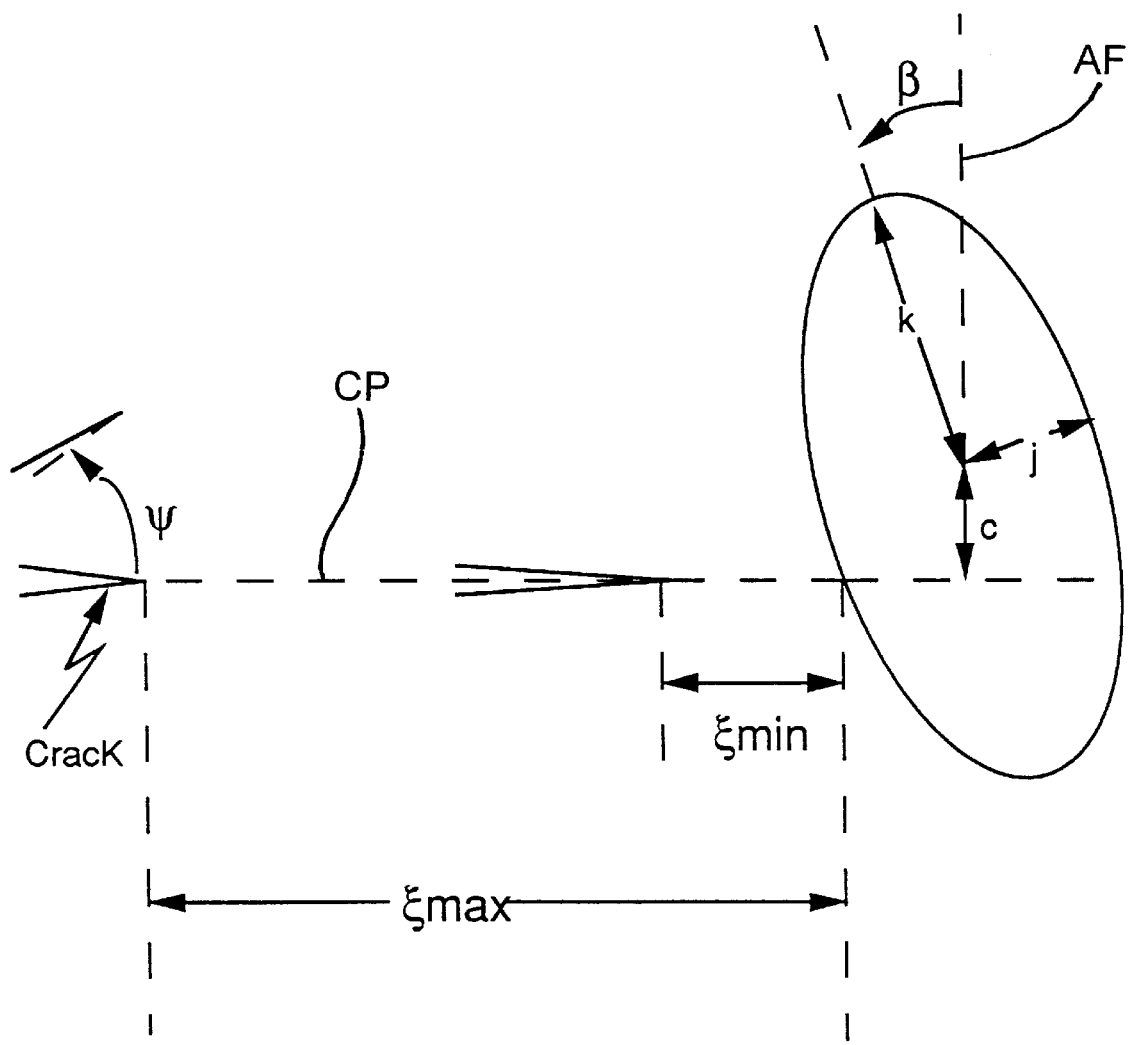
FIG. 5 shows a crack approaching an elliptically shaped entity.
Figure 6:
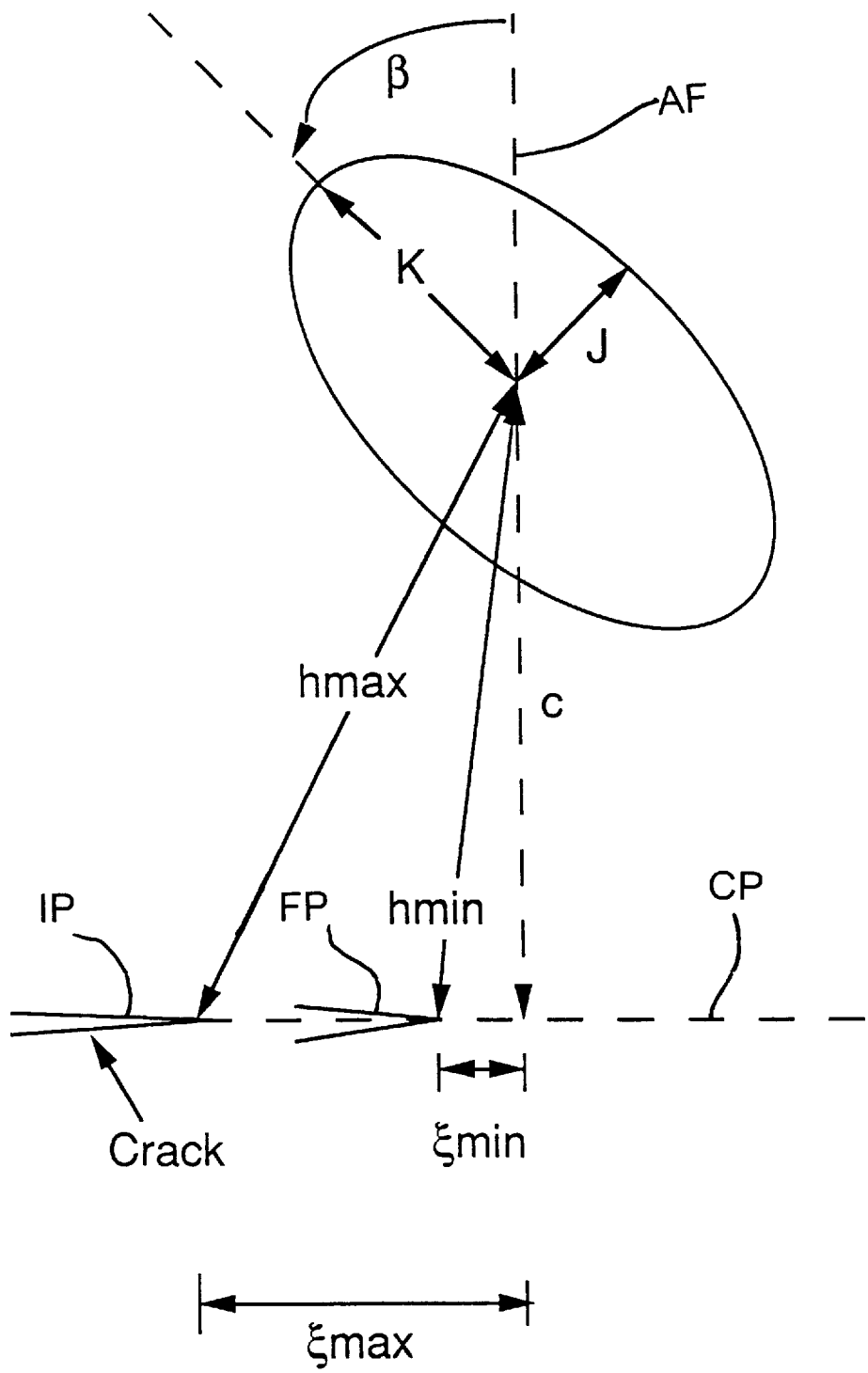
FIG. 6 shows geometrical parameters used in program setup when an elliptically shaped entity does not intersect the crack path.

The other angle that the user keys in as an input in all the programs is the angle $\psi$, which measures the angle in degrees of tilt that the crack makes with respect to the applied load, as shown in FIGS. 4, 5 and 6. It is measured from a line perpendicular to the applied load to the line of the crack path CP, as shown in FIG. 4.

The significance of the angle $\psi$ is that it enables a user to change the relative amounts of tensile and shear loading on the crack. The term "mode I" refers to a crack under tensile stress, and the term "mode II" refers to a crack propagating under shear stresses. The angle $\psi$ is one method enabling a user to control the relative amounts of energy release from mode I and mode II loading calculated later in the programs. The functions that calculate the stress intensity factors use angle $\psi$ as an input and the stress intensity factors are in turn used to calculate elastic stresses and elastic strain energy density, as discussed herein in section IIC. The other method of controlling the relative amounts of mode I and mode II loading, that of specifying the mode I and mode II stress intensity factors directly, is also discussed in section IIC.

The term "crack path" used in the last paragraph to define $\psi$ and used throughout this description and in the flow charts of FIGS. 25–66 refers to a straight line between the crack tip and the nearest edge of the microstructural entity, as shown as CP in FIG. 2A. It is also the line along which the parameters $\xi$, $\Delta\xi$, $\xi_{min}$ and $\xi_{max}$ are measured, as shown in FIGS. 2A, 4, 5 and 6.

Figure 7A:
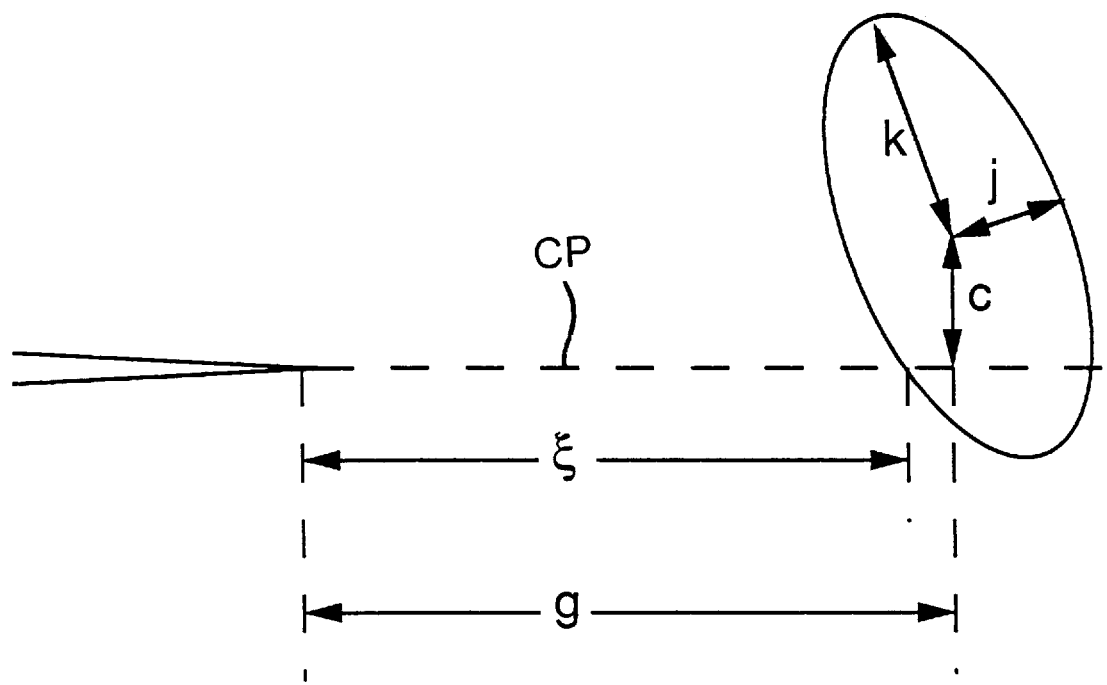
FIGS. 7A and 7B show a difference between $\xi$, g and c when an elliptically shaped entity does and does not intersect the crack path.
Figure 7B:
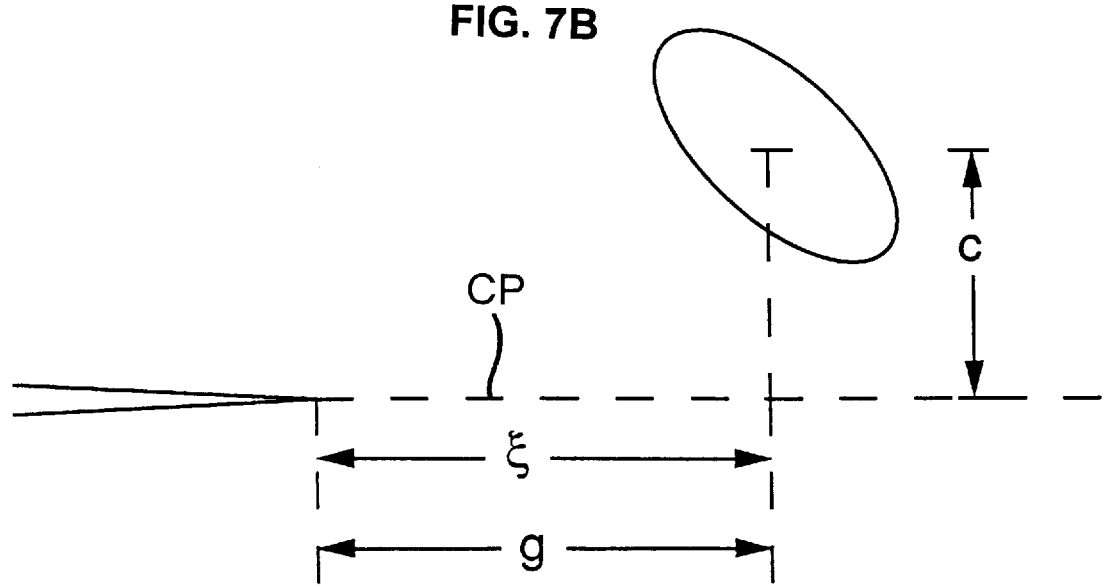

When an elliptically shaped entity is positioned above the line of direction of crack advancement when the crack moves in a straight line, as shown in FIGS. 6 and 7B, the term "crack path" (CP) refers to a straight line running between the crack tip and the point of intersection between this line CP and the line c running from the center of the ellipse perpendicular to this same line. In this setup, as shown in FIGS. 6 and 7B, it is said that the elliptically shaped entity "does not intersect the crack path". In the setup shown in FIGS. 5 and 7A, it is said that the elliptically shaped entity "intersects the crack path".

In the programs described herein the crack path CP remains a straight line between the crack tip and the interface. It is one object of the present programs to determine what would happen to the net energy released and absorbed if a crack were to attempt to move without deviating from a straight path toward the interface. It is also an object of the programs to enable a user, if desired, to change this angle easily during a hypothetical crack propagation through either a simple assignment statement or as a result of some energy quantity from a preceding crack position. In these cases the term "crack path" would refer to a line extending from the crack tip through the length $\Delta\xi$ shown in FIG. 2A.

Figure 35:
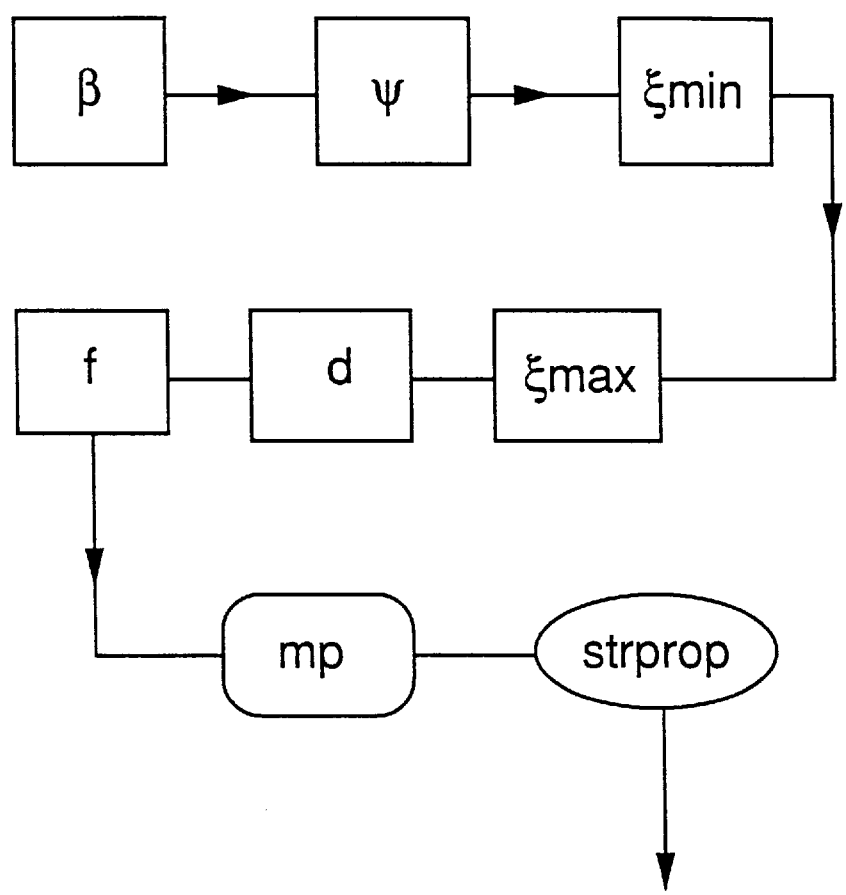
FIGS. 35–37 are flow charts for inquiries made of the user, inputs made by the user, and setup of material parameters.

IIB.2 Geometrical Parameters for Entities With Planar Sides (FIGS. 2A, 4 and 35)

The sequence of geometric variables that a user keys in at the beginning of the programs for microstructural entities with planar sides is shown in FIG. 35. The rectangular shaped boxes around the variables $\beta$, $\psi$, $\xi_{min}$, $\xi_{max}$, d and f denote inputs prompted by questions written in the programs and displayed on the screen in sequence after each input.

The variable $\xi$ for an entity with planar sides in the present programs measures the distance in microns (1 micron=$10^{-6}$ meter) from the crack tip to the nearest edge of the microstructural entity along the crack path, as shown in FIG. 2A. $\xi_{min}$, also measured in microns and shown in FIG. 4, is a minimum distance for $\xi$ selected by the user and is the closest that the crack tip will get to the microstructural entity. Similarly, $\xi_{max}$ is a maximum distance in microns selected by the user and is the initial distance of the crack tip from the interface.

Two other variables, d and f, are shown in FIG. 35 as parameters keyed in by the user for an entity with planar sides. d is the thickness of material 2, measured in microns, as measured along a line perpendicular to the planar sides, as shown in FIG. 4. The variable f is a dimensionless number defining the fraction of material 2 in a composite as measured along a line perpendicular to the applied load. The fraction is stored as the variable f in case a user would want to use it in modifying applied stresses and stress intensity factors to take into account a bimaterial composite.

IIB.3 Geometrical Parameters for Elliptically Shaped Entities (FIGS. 5, 6, 7A, 7B, 8, 36 and 37)

Figure 8:
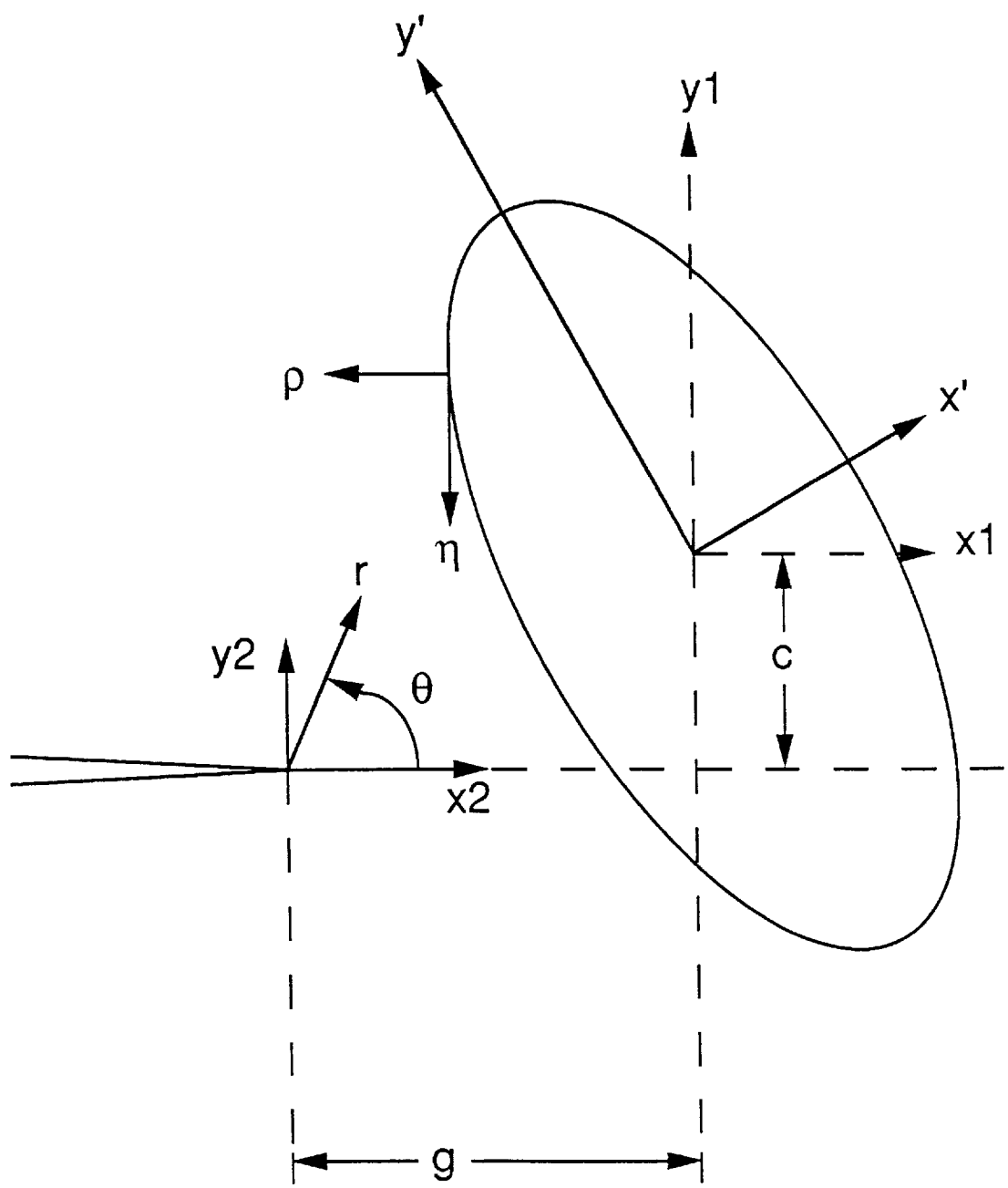
FIG. 8 shows coordinate systems used in the preferred embodiment.

Geometric variables for an elliptically shaped entity, shown in FIGS. 5, 6, 7A, and 7B, are different from those of a planar entity. In the ellipse representing the elliptically shaped entity, k is the length in microns of the major axis of the ellipse, and j is the length in microns of the minor axis of the ellipse (FIGS. 5, 6 and 7A). c is the vertical distance in microns from the center of the ellipse to the line of the crack path, as shown in FIGS. 5, 6, 7A and 7B. The variable c may also be expressed as the vertical distance in microns between the x2, y2 and x1, y1 coordinate systems measured along the y2 and y1 axes as shown in FIG. 8.

The definitions of $\xi$, $\xi_{min}$ and $\xi_{max}$ for elliptically shaped entities depend upon whether the entity intersects the crack path, as shown in FIGS. 5, 6, 7A and 7B. When the entity intersects the crack path, $\xi$ is, as in the case of an entity with planar sides, the distance in microns from the crack tip to the nearest edge of the ellipse as measured along the crack path and as shown in FIG. 7A. Similarly, the parameters $\xi_{max}$ and $\xi_{min}$ are the initial and final distances in microns of the crack tip to the nearest edge of the ellipse as measured along the crack path, as shown in FIG. 5.

When the elliptically shaped entity does not intersect the crack path CP, $\xi$ is the distance in microns of the crack tip to the point of intersection between the line along which c is measured and the line coinciding with the crack path, as shown in FIG. 7B. $\xi_{max}$ and $\xi_{min}$ are then similarly the initial and final distance of the crack tip measured in microns along the crack path to this same point of intersection, as shown in FIG. 6.

When an elliptically shaped entity does not intersect the crack path CP, there are two geometric parameters keyed in by the user at a question displayed on the screen by the programs. They are $h_{min}$ and $h_{max}$, measured in microns, and shown in FIG. 6. $h_{max}$ measures the distance between the center of the ellipse and the initial position IP of the crack tip selected by the user. $h_{min}$ is the distance between the center of the ellipse and the final position FP of the crack tip selected by the user. The final position of the crack tip is either the point at which the line intersects the crack path or is at the closest distance to that point that a user would want to the crack tip to get after advancement is complete.

After values to the angles $\beta$ and $\psi$ have been assigned, another important angle is calculated in all the programs. The angle is $\phi$, measured in radians, and is the difference between the angles $\beta$ and $\psi$. $\beta$ and $\psi$ are first converted to radians in a known manner by dividing by 180 and multiplying by $\pi$ before the quantity $\beta-\psi$ for $\phi$ is calculated.

The significance of the angle $\phi$ is that it is related to the actual angle of approach between the crack tip and microstructural entity. Once $\beta$ is set, the actual angle of approach will be set by the angle of tilt $\psi$ of the crack. The actual angle of approach is $(\pi/2)-\phi$. When $\beta$ is 45 degrees, for example, and the crack is tilted upward by an angle $\psi$ of 45 degrees, $\phi$ will be zero, and the crack will approach the microstructural entity at a right angle.

In this discussion and in the Flow Charts, specifically in FIGS. 28 and 30 (to be described in detail below), the term "approach at a right angle" in the case of a planar microstructural entity means that the line coinciding with the crack path is perpendicular to a line parallel to the sides of the planar entity. The sides of the planar entity are depicted as solid lines in FIGS. 2A and 4 marking the boundary or interface between materials 1 and 2. When the entity is elliptically shaped, "approach at a right angle" means that the line coinciding with the crack path is perpendicular to the line coinciding with the major axis of the ellipse of length k in FIGS. 5 and 6.

Figure 36:
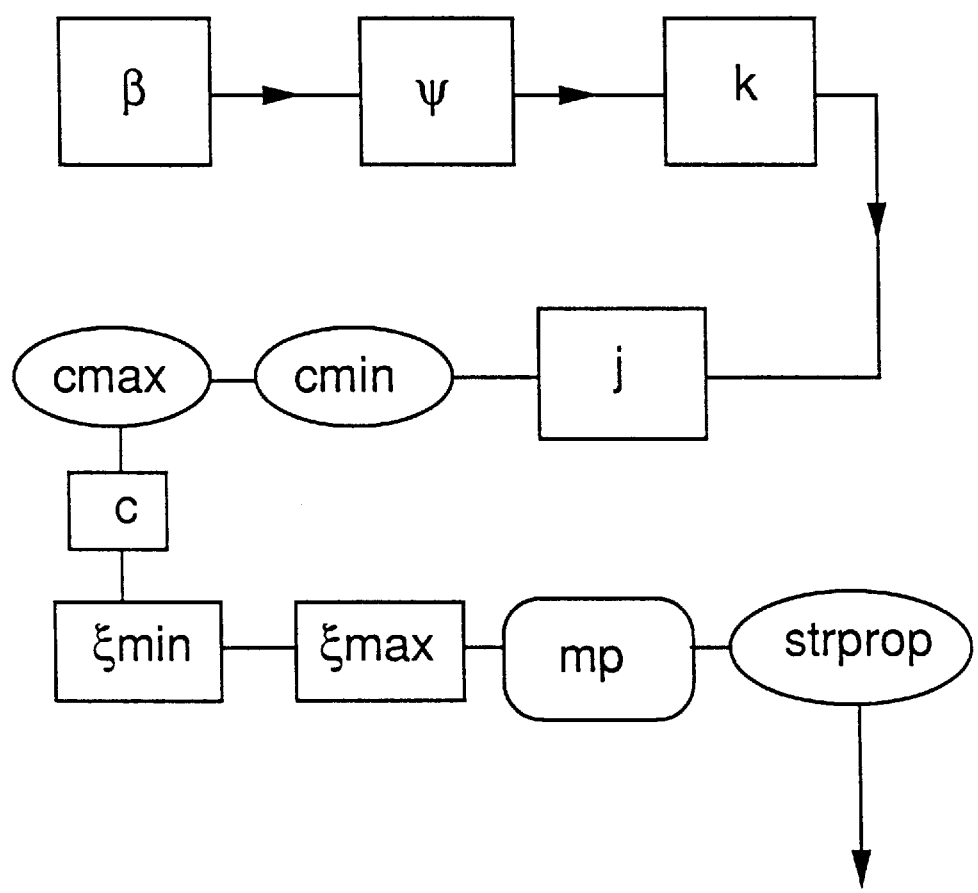
Figure 37:
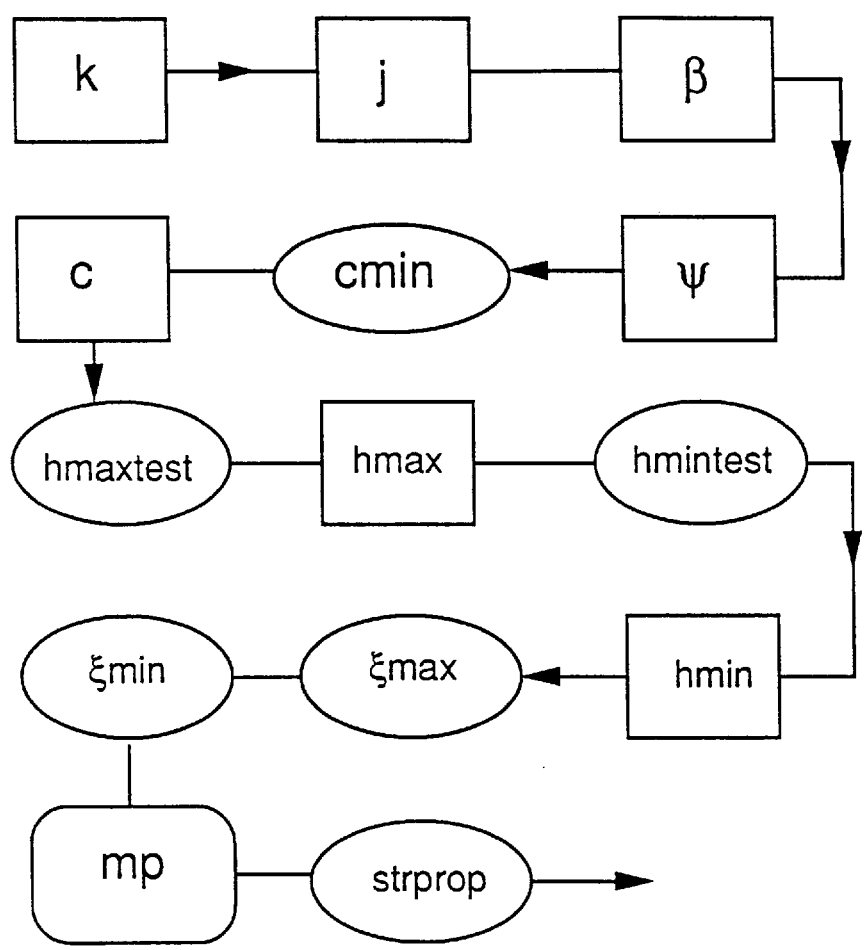

The sequence of steps for assigning the first geometric parameters for elliptically shaped entities is shown in FIGS. 36 and 37. FIG. 36 shows the sequence when the entity intersects the crack path. Parameters cmin and cmax are calculated before a user keys in c to give an estimated range of c to ensure that the entity intersects the crack path. Since c can be positive or negative, cmin and cmax are estimated at negative and positive (k×cos$\phi$×0.8) when $\phi$ is not a large angle. cmin and cmax can also be set by the user in a simple assignment statement. $\xi_{min}$ and $\xi_{max}$ are entered directly by the user at a question prompt.

FIG. 37 shows the sequence of steps taken to assign the basic geometric parameters when an elliptically shaped entity does not intersect the crack path. A minimum value cmin is estimated at (1.2×k×cos$\phi$) for $\phi$ not large before a user types in c to ensure that the entity does not intersect the crack path. cmin again can be changed by a user in a simple assignment statement.

Parameters hmaxtest and hmintest are assigned the values of c before a user keys in hmax and hmin to ensure that the crack itself does not intersect the entity and that again the entity does not intersect the crack path, as shown in FIG. 7B. hmaxtest and hmintest can also be changed in a simple assignment statement. $\xi_{min}$ and $\xi_{max}$ then become quantities calculated inside the programs from the right triangles formed by $\xi$, c, and hmin or hmax respectively.

IIB.4 Assignment of i, $\Delta\xi$ and $\xi$

Within a large main loop in the programs the positions of the crack are changed. Inside this same loop the necessary checks and calculations for energy are done for a particular program. The loop is labeled "i loop", is controlled together by the counting integer i and $\Delta\xi$, and appears in FIGS. 32, 33, 38, 41, 42, 43, 44, 45, 46, 47, 55, 56, 57, 58, 59, 60, 61, 62, 63 and 64. The parameter labeled "i" appearing next to $\Delta\xi$ near the top of these figures labels the number of iterations for the loop. The two filled circles next to $\Delta\xi$ and i and next to other parameters in the Flow Charts mean that they play some role in controlling the flow of the software.

The functions that calculate i and $\Delta\xi$ use $\xi_{min}$ and $\xi_{max}$ selected by the user as inputs. The difference between $\xi_{max}$ and $\xi_{min}$ is taken, and, depending upon the size of this difference, an integer for i is assigned. $\Delta\xi$ is obtained by dividing the difference between $\xi_{max}$ and $\xi_{min}$ by i. A user with some knowledge in programming can therefore change the size of i and $\Delta\xi$ to have the crack advance over long distances or, alternatively, look at energy calculations taken at many increments of advance in a smaller region of interest.

Inside the programs $\xi$ is actually assigned so that the crack tip begins at the position $\xi_{min}$ and backs up to $\xi_{max}$. A user can therefore see what kinds of energies are being calculated first very near an interface. The procedure uses $\xi_{min}$, i and $\Delta\xi$ as inputs and assigns $\xi$ as ($\xi_{min}+((i-1)\times\Delta\xi)$), where i runs from 1 to its maximum value. Energy differences per unit length of crack advance are calculated in the programs as if the crack were advancing toward the interface, however, with the graph at the end having $\xi$ decreasing when moving from left to right along the horizontal axis as shown consistently in FIGS. 2A, 4, 5 and 6.

IIC. Assignment of Material Data and Radii of Circular Regions (FIGS. 2A, 2B, 3–8, 9A–9F, 11A–11F, 13, 17, 19, and 35–37)

There are two kinds of preliminary data assigned to the materials and to the crack itself inside the programs. There are data that are largely independent of the crack length, which are mainly elastic constants and yield stresses found in handbooks and in literature. There are also data that depend explicitly upon the instantaneous value of the crack length, which include the crack length itself, stress intensity factors and radii of plasticity.

Data not largely dependent upon the instantaneous position of the crack are assigned in simple assignment statements before the main i loop. They can be easily changed by a user with some knowledge of computer programming and include the elastic constants of the materials, thus allowing the user to decide what materials 1 and 2 will be in FIGS. 2A, 4, 5 and 6 or if the system containing the crack will consist of only one material.

Data that are assigned before the main i loop that are material properties are listed just before this discussion with their units. They include the Young's moduli E1 and E2 for materials 1 and 2, the shear moduli G1 and G2 for materials 1 and 2, the Poisson's ratios v1 and v2 for material 1 and 2, and the yield strengths ys1 and ys2 for materials 1 and 2. The Young's moduli are usually recorded in literature in gigapascals but for computational purposes are assigned in megapascals. The Poisson's ratios are dimensionless decimal fractions in the range of 0.2 to 0.35, and the yield strengths are in megapascals. A surface energy can also be assigned by the user within a simple assignment statement. It is usually recorded in literature in joules/meter$^2$ but for computational purposes is assigned in joules/micron$^2$. When it is desired to take surface energy into account, a unit thickness, when $\Delta\xi$ is in microns, is 1 micron. The amount of surface energy absorbed for each increment of crack advance can then be approximated by a surface energy selected by the user multiplied by $\Delta\xi$.

Two other parameters, a and b, are also assigned before the main loop. a is the initial crack length in millimeters. b is the radius of the circle within which elastic energy is calculated shown in FIGS. 2B, 9A–9E, 11A–11E, 13, 17 and 19. In this discussion the term "radius of elasticity" will refer to this parameter b in microns. It is a radius easily adjusted by the user of a circular area within which changes in elastic strain energy locally affect crack propagation.

It is one object of the system to allow a user to investigate crack growth and toughening mechanisms occurring at the atomic level or over larger areas. The radius b can therefore be adjusted by the user. In the current programs it is set within 100 microns because the elastic stresses used to calculate strain energy density are valid in the vicinity of the crack tip. For plasticity or some other toughening mechanism that could be modeled at the atomic level, the user need only know what the mechanism is per unit area or volume. The user could also know or set the quantity as a function of spacial variables in either the x2, y2 coordinate system at the crack tip or in the local x', y' coordinate system in the ellipse if the entity is elliptically shaped. The numerical integration in the programs will calculate the energy in the appropriate regions.

If it is desired that the entire system itself consisting of the crack and interface be investigated at a nanometer scale or, alternatively, at a millimeter scale or larger, the only adjustment a user would need to do is change the units and conversion factors throughout the programs and procedures used. A user would not necessarily need to change to a completely different kind of modeling on another computer system.

The parameters depending explicitly upon the crack length are abbreviated "crprop" and are the stress intensity factors and the radii of plasticity. The actual crack length itself is calculated within the i loop by taking the difference between $\xi_{max}$ and the value of $\xi$ at that point, adding the difference to the initial crack length and converting the result to meters for later calculations.

The functions for the stress intensity factors use the applied stress, $\psi$ and crack length a as inputs. The tensile and shear components of the applied stress acting oil a plane coinciding with the plane between the two crack surfaces[1] are calculated by multiplying the applied stress by $\cos^2\psi$ for the mode I factor and by $\cos^2\sin\psi$ for the mode II factor. The functions in the programs approximate some intensity factors for an edge crack by multiplying these results by 1.12 and by the square root of a.

It is an object of the programs to enable a user to investigate potential toughening mechanisms without having to construct entirely new models for different specimens and testing geometries that result in different stress intensity factors. A user with some programming experience can change these formulas for the stress intensity factor for cracks of other shapes or for intensity factors for specimens of specific dimensions. Alternatively, values for intensity factors for experiments already performed can be assigned through simple assignment statements. They can also be adjusted if desired to take into account that the crack is near a bimaterial interface. The user need not draw a new model on a computer screen for a new specimen or test a new specimen in a laboratory right away.

Figure 2B:
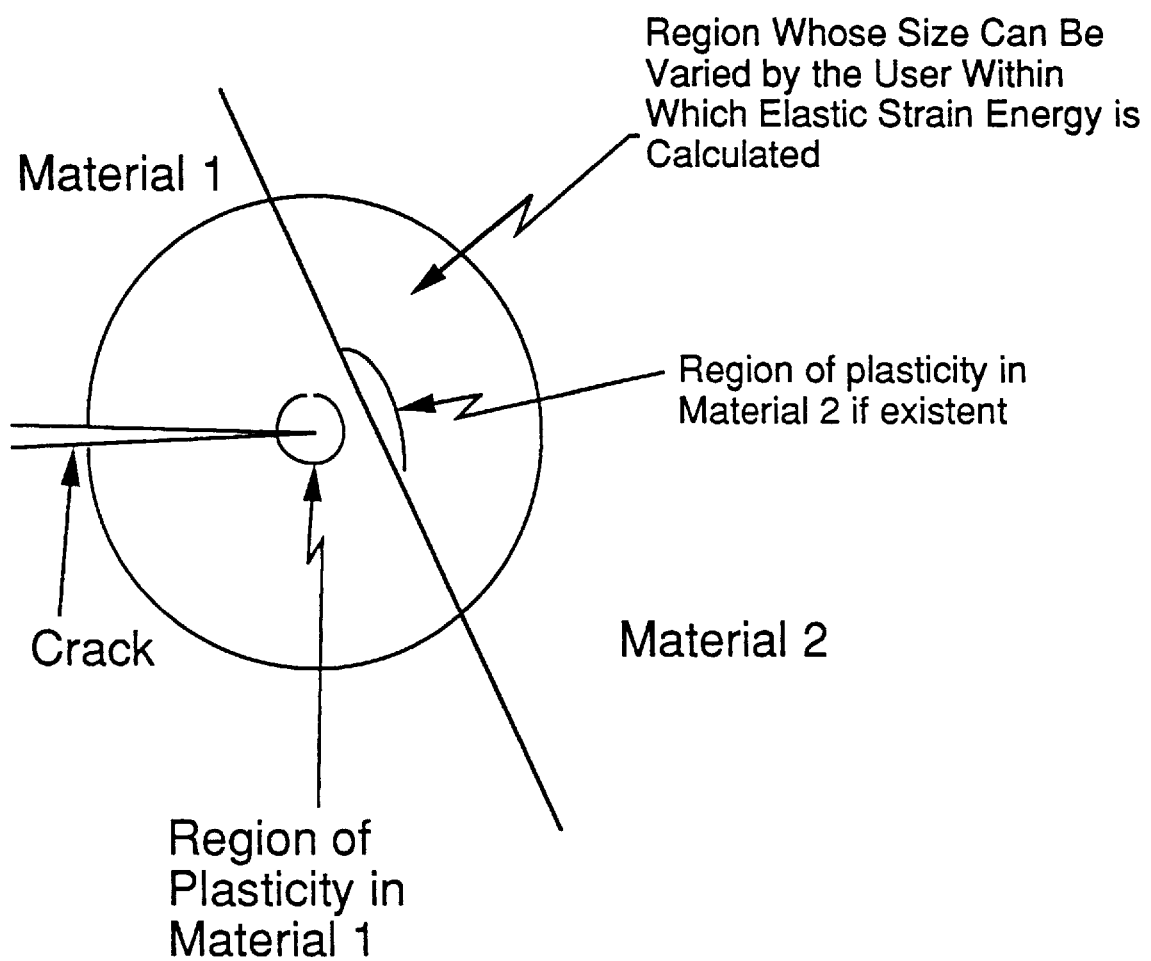
FIG. 2B shows circular regions used for numerical integration.

The term "radius of plasticity" refers to the radius of a circular region within which yielding, work from plasticity or any other process that could absorb energy and counteract the strain energy release is being done for a particular material. For plasticity, the regions can have various shapes to them[2] for various modes of loading but in the present programs are approximated as circles, as shown in FIG. 2B.

The functions for the radius of each material use the yield stress and stress intensity factors as inputs. The square of the stress intensity factor is divided by both 2 $\pi$ and by the square of the yield stress and then converted to microns to give an approximate radius[2] for each material in question. If some other process other than plasticity is absorbing energy in material 2, the user can set the radius from the crack tip within which the process occurs.

IID. Summary

In summary, geometric parameters assigned at the beginning of all the programs are $\beta$, $\psi$, $\xi_{min}$, $\xi_{max}$ and b. When the microstructural entity is planar, d and f are assigned. When the microstructural entity is elliptically shaped, j, k and c are assigned. When an elliptically shaped entity does not intersect the crack path, hmin and hmax are assigned and $\xi_{min}$ and $\xi_{max}$ are calculated.

Material properties that are assigned before the crack advancement begins are a, E1, E2, G1, G2, v1, v2, yield strengths of materials 1 and 2, the applied stress and surface energy. For each increment of crack advance inside the i loop, the length of the crack, stress intensity factors for modes I and II for both materials and plastic radii for material 1 and 2 are calculated. These properties have been described herein above.

The label "mp" in FIGS. 35–37 is for the assignment of material properties such as E1, E2, v1 and v2 before the i loop that are found in handbooks and in literature and are not explicitly dependent upon crack length. The rounded rectangular box denotes a series of simple assignment statements.

The term "strprop" refers to calculations of stress properties or calculations on the applied stress that optionally can be set by a user with some programming experience to take into account a bimaterial interface before the stress intensity factors are calculated.

The entire sequence of variable assignments before the main i loop in FIGS. 35–37 are denoted Inquiries 1, 2 and 3, respectively, or I1, I2 and I3 for short in other figures. One or more of the sequences I1, I2 or I3 appears in a rectangular box and begins the flow of software in FIGS. 32, 33, 38, 41–47, and 55–64.

Properties such as crack length, stress intensity factors and plastic radii calculated during crack advance are abbreviated "crprop". The abbreviation crprop appears in FIGS. 32, 33, 38, 41–48, and 57–64.

III. Structure of the Programs on the Apparatus and Method of Use by the User

IIIA. Introduction

Figures 67, 68:
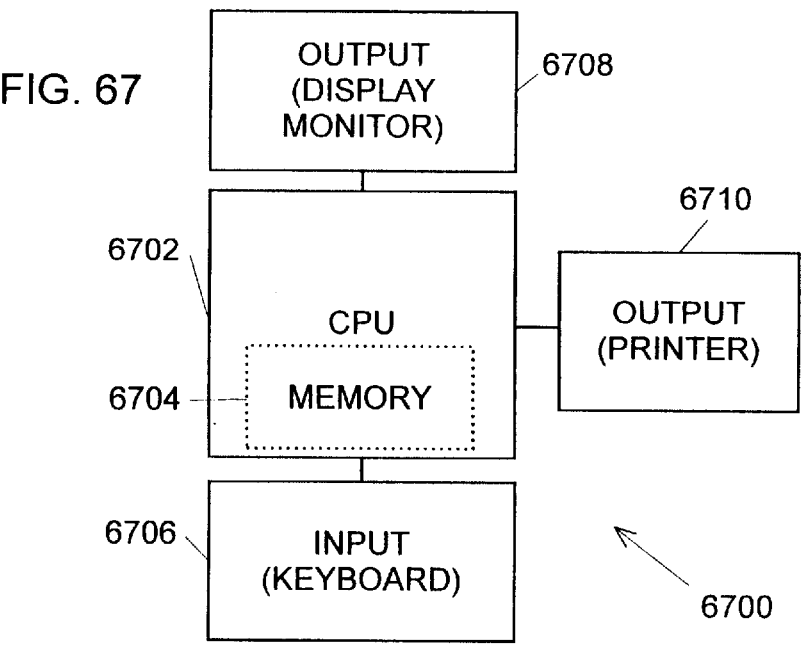
FIG. 67 shows a block diagram of an IBM compatible personal computer on which the present invention can be implemented.
FIG. 68 shows a data structure formed in accordance with the preferred embodiment.

This section describes how the interactive series of programs for crack advancement, recognizing where the crack is, performing necessary numerical integrations over regions and storing data in memory and in a final graph is structured to work on a personal computer. The series of programs is currently written and works on an IBM compatible personal computer with an 8087 mathematics coprocessor. As shown in FIG. 67, such a computer 6700 includes CPU 6702 with memory (RAM, disk drive(s), and other storage) 6702, inputs including keyboard 6704, and outputs including display monitor 6708 and optionally also printer 6710. The section refers to FIGS. 25–31 and shows how a user would use the system of programs.

It is one advantage of the present system that it has been structured to run by using a series of diskettes and programs on a personal computer. Scaling the system up for potentially more complex or automated processes desired by a user would only require lengthening the processes herein described on a personal computer or combining processes herein described for placement on a larger computer. Those skilled in the art who have reviewed this specification will readily understand how to do so. The opposite step of configuring the programs from a structure running on a supercomputer to that on a work station would not need to be done.

IIB. Basic Structure of the System (FIGS. 25 and 26)

IIB.1 Overview

Figure 25:
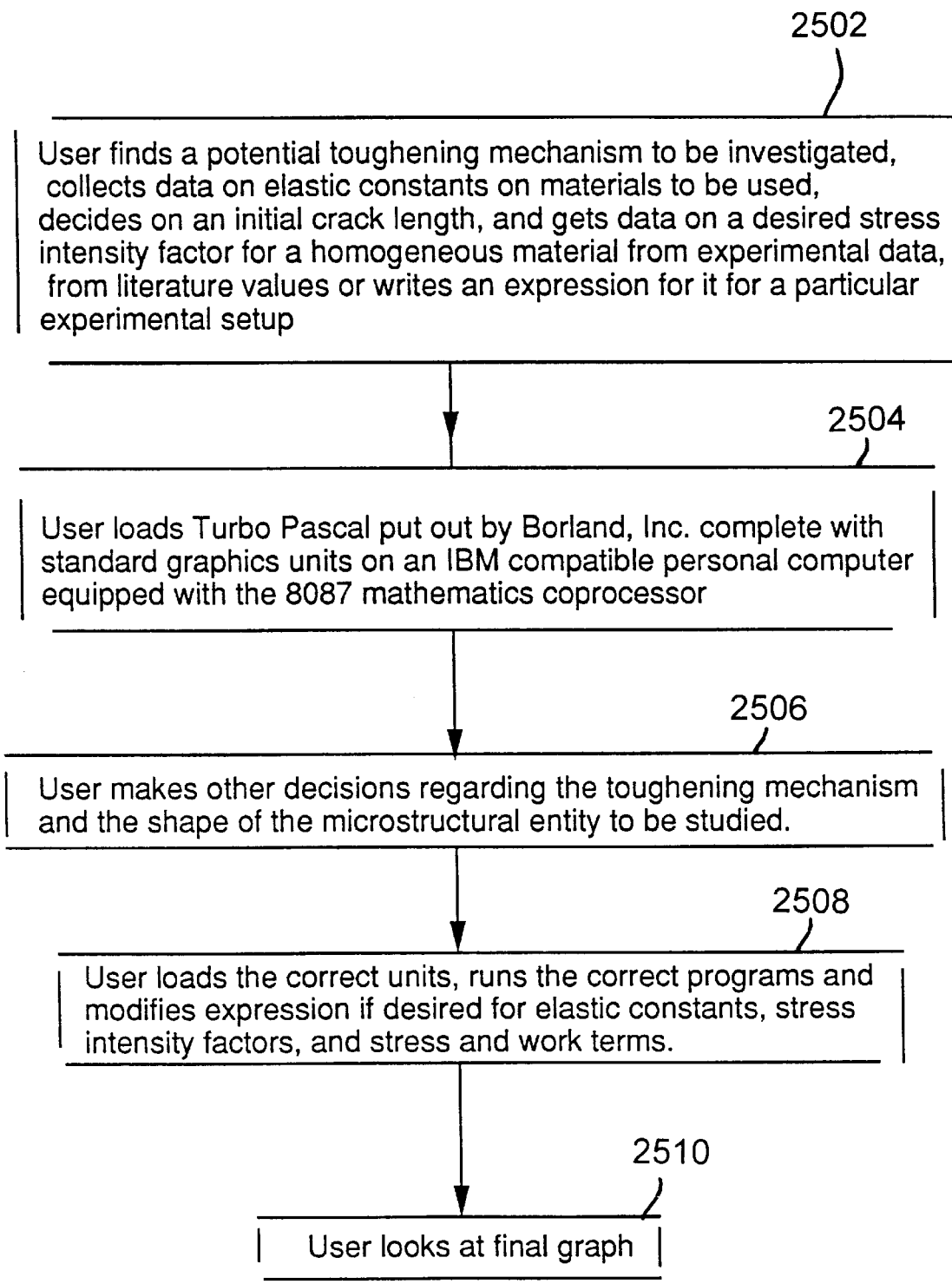
FIG. 25 is a flow chart showing an overview of the user's interaction with the method an apparatus of the preferred embodiment.
Figure 26:
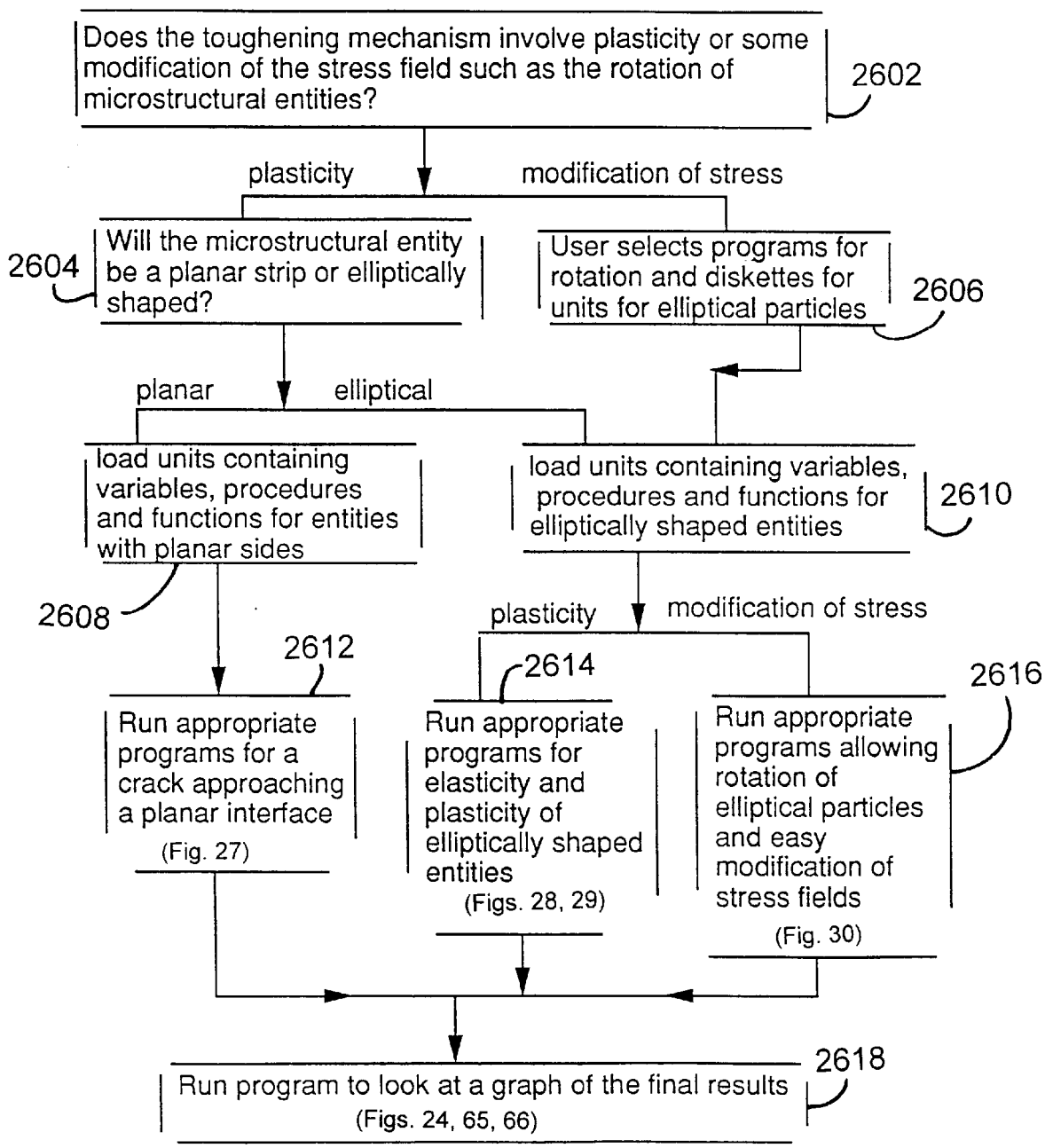
FIG. 26 is a flow chart of initial decisions and actions.

FIG. 25 shows an overview of decisions and actions made by a user in terminology discussed in the previous two sections. In step 2502 the user exercises alternatives discussed earlier about choosing the material system, getting data on elastic constants and deciding on an initial crack length and stress intensity factors. The current set of programs are written in Pascal so a user would load the indicated backup software to run the programs in Pascal, as indicated in step 2504.

The programs are run in specific series depending upon the shape, size, orientation and position of the microstructural entity. They are also run in specific series depending upon whether the toughening mechanism will depend upon plasticity or upon modification of a stress field. These options open to a user mentioned steps 2506 and 2508 in FIG. 25 are shown in more detail in FIG. 26.

The sequence of programs a user would run for various setups are shown in FIGS. 27–31. Listings and descriptions of actual programs are located at the end of this specification. The final step is to look at various net energy terms added up or look at a final graph of net energy versus the distance $\xi$ of the crack tip from the microstructural entity, as in step 2510 of FIG. 25.

FIG. 26 outlines the actual steps a user would take with the programs on a personal computer. Currently there are programs for the rotation of elliptically shaped entities, but it is possible to modify the stress field for other mechanisms within the radius b for a planar entity. The term "units" refers to groups of procedures and functions used by the programs that are organized into a structure like a program running in the background when using Turbo Pascal. For plasticity, one moves down the chart based upon whether the microstructural entity is planar or elliptically shaped. Once the array of final data for each crack position is stored in memory, the same program labeled Rtest1 at the bottom of FIGS. 27–31 can be run to produce a graph regardless of the prior series of programs run.

IIIB.2 Structure of the Data Stored in Memory

In each series of programs run by the user, each energy quantity calculated is stored in its own data file. Strain energy released within the region of width $\Delta\xi$, for example, is stored in one file. The change in strain energy for each increment of crack advance for the entire region of radius b is stored in a different file. Plastic work in materials 1 and 2 would be stored in yet two other files.

For some combinations of cracks and elliptically shaped entities, more than one file fills with a particular energy. Each position corresponding to a crack position in each file in this case gets that energy quantity integrated over a portion of a possible region of overlap. The listing of some representative series of programs after the glossary of terms for the flow charts at the end of the specification shows the different files filling for different programs.

Each data file for an energy result is a one dimensional array. Each position in the array corresponds to each crack position in the advancement and retains a value of zero unless specific overlap conditions between a region for the energy quantity and one of the materials is met. If the conditions are met, a numerical value for energy is stored in the data file.

At the end of running a series of programs the structure of the data stored in memory will look like a large two dimensional array, as shown in FIG. 68. One dimension of the array is the series of data files used for all the series of programs run. The other dimension of the array is the series of crack positions corresponding to each crack increment $\Delta\xi$ between $\xi_{min}$ and $\xi_{max}$.

In preparing results for a graph at the end, the data files are opened. For each crack position, the numbers in all the files corresponding to that position in the are added together. The numbers added together could be a combination of zeros and nonzero numbers. A user with some programming experience could at this point could look at one energy quantity alone or a partial list of them.

IIIB.3 Preliminary Preparation of Data Files and Description of Rfile0

A program labeled Rfile0 appears at the beginning of FIGS. 27–31 and sets the numbers stored in all or selected data files just discussed in the preceding paragraphs to zero. It first asks the user to key in the values of $\xi_{min}$ and $\xi_{max}$ that will be used in all programs run for a particular crack advancement of interest. The maximum counting integer for the main loop i is then calculated as discussed in section II on Definition and Preparation of Basic Data. Two or more loops of counting integer i are used to open all the data files, and as i increments to the next integer, the corresponding position in each file is given a value of zero.

In the program discussed in the previous paragraph a user can adjust the assignment statements so that all the positions in all or one or only a few of the data files are set to zero. At the beginning of a new geometric setup and crack advancements, all files could be set to zero. If a user wanted to collect data again, for example, for plasticity in material 2, and keep all other energy quantities in other data files intact, the user would need only to adjust the assignment statements so that the data file for plasticity in material 2 is set to zero.

IIIC. Programs for an Entity With Planar Sides (FIG. 27)

Figure 13:
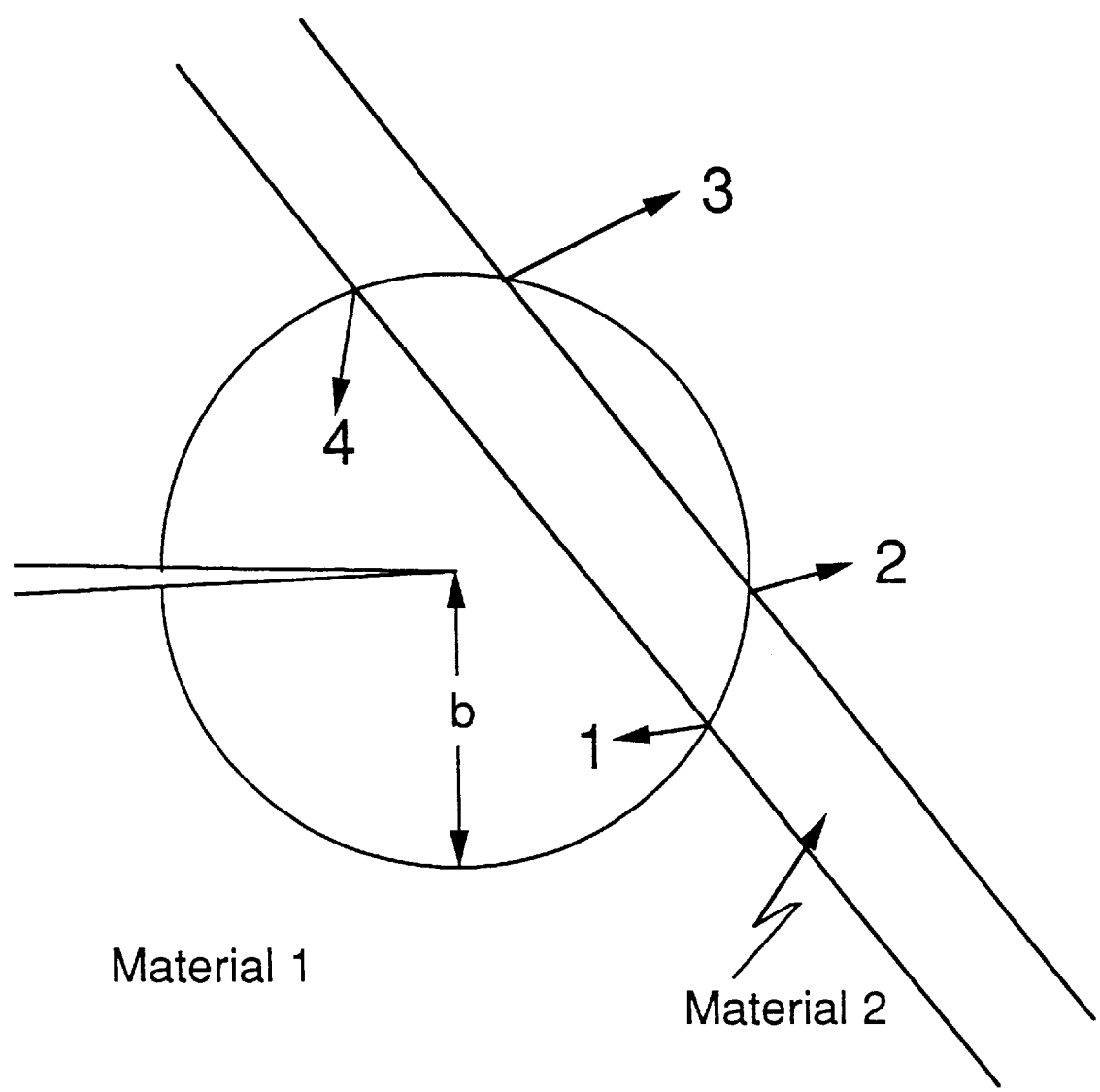
FIG. 13 shows a circular region containing a planar entity of a material within which elastic energy is calculated.
Figure 27:
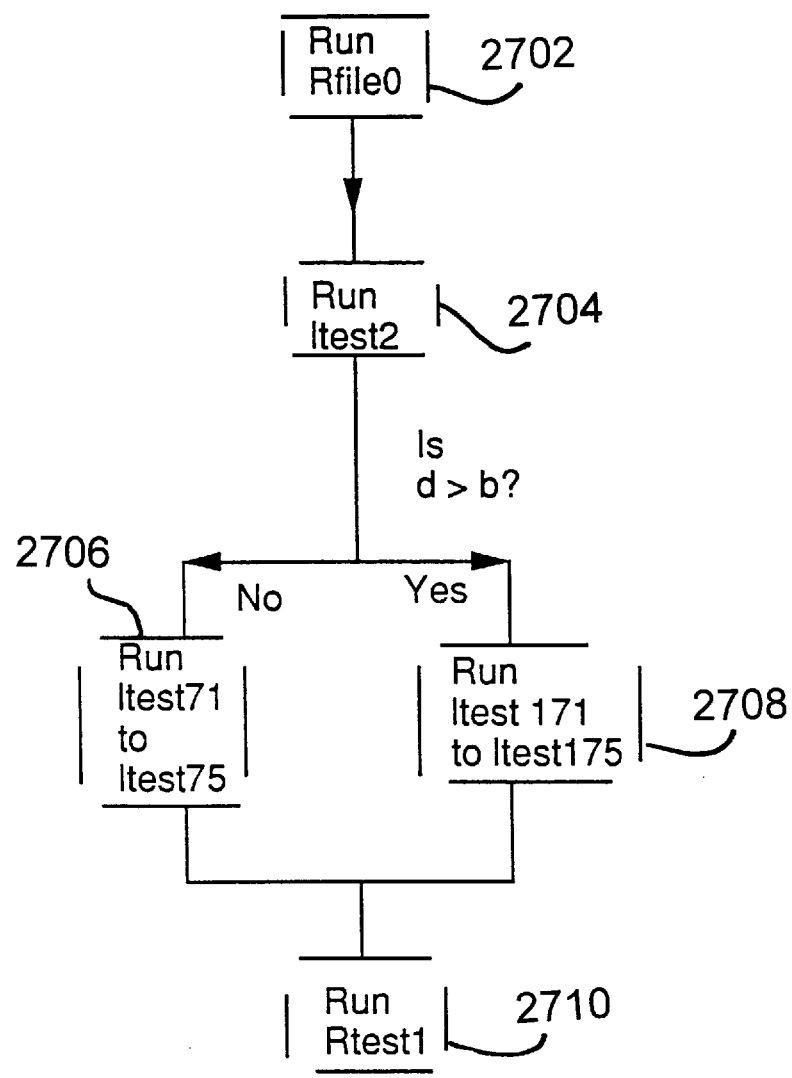
FIG. 27 is a flow chart of operations performed when the second material is a planar strip.

FIG. 27 shows a sequence of steps when the microstructural entity has planar sides. The first step (step 2702) is running the program labeled Rfile0 just discussed. The second step (step 2704), running a program Itest2, calculates strain energy release just above and below the increment of crack advance $\Delta\xi$. The question "Is d>b?" is asking whether the circle of radius b will be contained within material 2, as shown schematically in FIG. 2B, or will extend over material 2 and back into material 1, as shown in FIG. 13. If the setup is as shown in FIG. 13, one moves to the left in the chart to run a series of programs labeled Itest71 to Itest75 (step 2706) before running the program Rtest1 for a final graph (step 2710). In the case in which material 2 is a semi-infinite plane so to speak in comparison with the radius b, another set of programs labeled Itest171 to Itest175 is run (step 2708).

IIID. Programs for Elliptically Shaped Entities (FIGS. 28–31)

Figure 28:
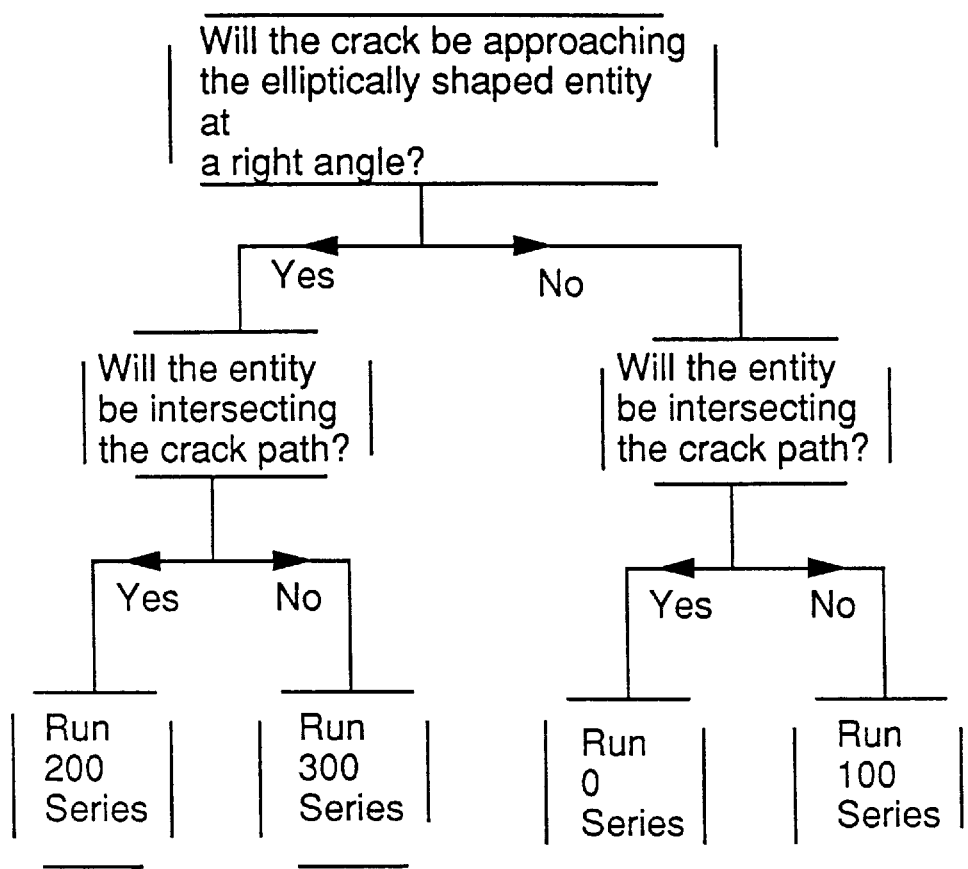
FIGS. 28–30 are flow charts of operations performed when the second material is elliptically shaped.
Figure 29:
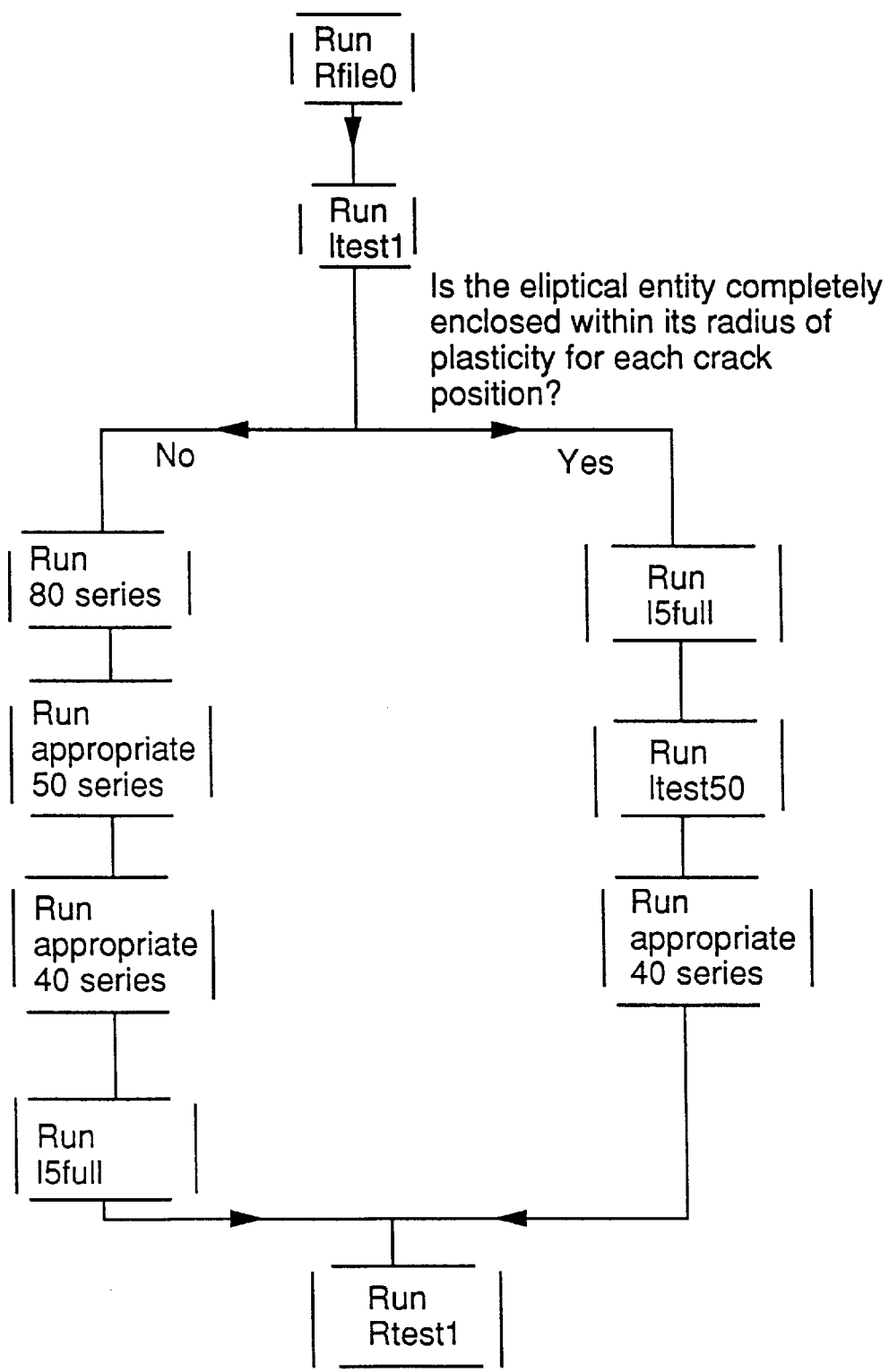
Figure 30:
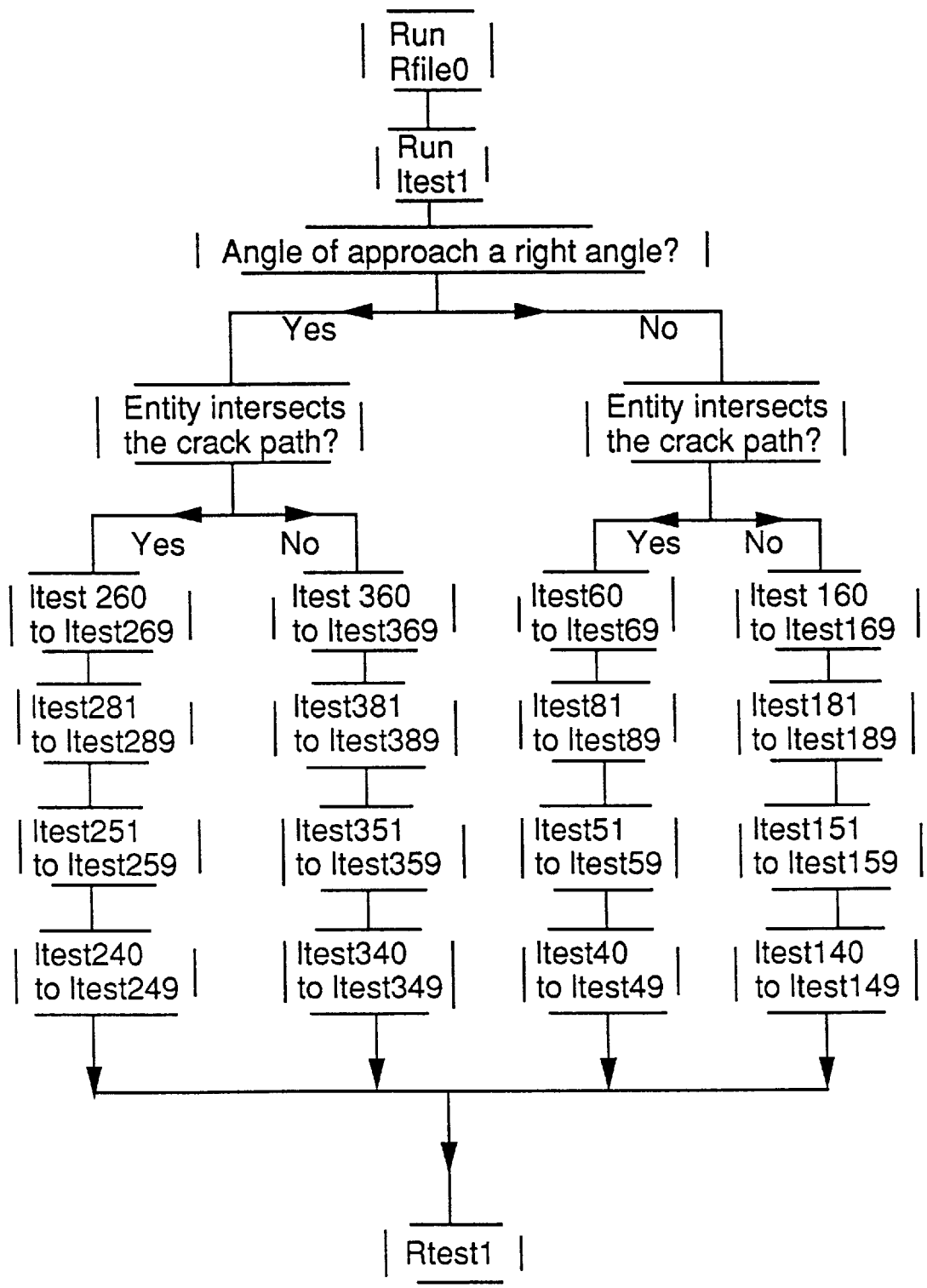

FIGS. 28–30 show the sequence of choices made and programs run when the microstructural entity is elliptically shaped. FIG. 28 first gives an overview of selecting the correct series to use depending upon the angle of approach of the crack to the entity and upon whether or not the entity intersects the crack path. The term "run appropriate series" in FIG. 29 and the numbers in the hundreds place in FIG. 30 refer to these series.

In summary, if the crack does not approach the entity at a right angle and the entity intersects the crack path, there is a 0 or no digit in the hundreds place, and the series is referred to as the 0 series. If the crack does not approach at a right angle, but the entity does not intersect the crack path, there is a 1 in the hundreds place, and the series is referred to as the 100 series. The 200 and 300 series are for cases when the crack approaches the entity at a right angle. In the 200 series the entity intersects the crack path, and in the 300 series it does not. Further explanation of the numbering of the programs is in a note after the listing of the programs.

FIG. 29 shows choices made and programs run when the elliptically shaped entity is completely enclosed within the circle of radius b or perhaps also within the region for plasticity in material 2. There are particular programs run in which appropriate numerical integration will occur over the entire elliptically shaped entity without needing all the checks and flags for partial overlap. The first step in running Itest1 refers to getting the strain energy release if desired within the region of width $\Delta\xi$ just in front of the crack tip and will be discussed in more detail in the next section.

One moves to the left in FIG. 29 if the entity is enclosed within the circle of radius b but when there could be no plasticity in the entity or only over a portion of it. I5full finds the elastic strain energy change within the radius b including the entity. The 80 series subtracts out elastic strain energy in a region where plasticity could be occurring. The 50 series finds plastic work or energy absorbed through plasticity in material 2, and the 40 series finds plastic work in material 1. The right hand side of the chart is for a very small entity near the crack tip that is always plastically deforming. The program Itest50 finds plastic work in the entire entity.

FIG. 30 is for a larger elliptically shaped entity for which the region within which elastic strain energy is calculated only partially overlaps the entity. Likewise, plasticity could be occurring over part of the entity or not at all. The programs in the series determine spatially what must be calculated and are chosen again by whether the angle of approach will be a right angle and whether the entity intersects the crack path. Within this setup there is also the option of running Itest1 for energy release just within $\Delta\xi$ and looking at a final graph with Rtest1.

Figure 31:
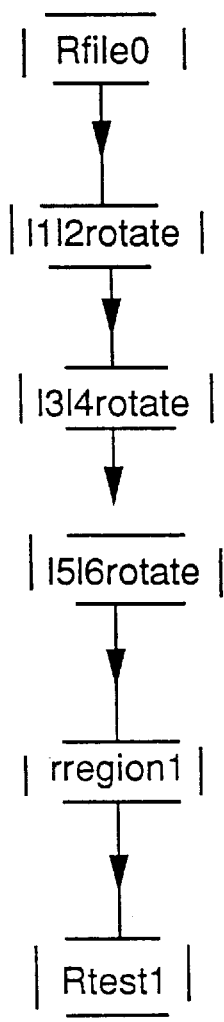
FIG. 31 is a flow chart of operations performed when there is a rotation of the elliptically shaped entity.

FIG. 31 shows a sequence of programs when there is rotation of the elliptically shaped entity or some other modification of a stress field and formulas in the $\rho$, $\eta$ coordinate system in FIG. 8 are needed. I1I2rotate, I3I4rotate and I5I6rotate refer to programs running within the region of width $\Delta\xi$ and within the limits of integration I1, I2, I3, I4 and I5 discussed in the next section.

IV. Crack Advancement and Assessment of Potential Toughening Mechanisms

IVA. Crack Advancement Toward an Entity With Planar Sides (FIGS. 2A, 3, 4, 9A–9F, 1A–10B, 13–16, 38, 39A, 39B, and 40–44)

IVA.1 Energy Release Just Above and Below the Increment of Crack Advance Including the Setting of Final Flag (FIGS. 2A, 3, 4, 9A–9F, 10A–10B, 13–16, 38, 39A, 39B and 40)

Suppose a crack approaches an entity with planar sides, as shown in FIGS. 2A, 3 and 4. When a crack advances by an increment $\Delta\xi$, the region of material lying vertically above and below the length $\Delta\xi$ shown in FIG. 3 will be released from the applied load. Before the incremental crack advance, the applied stress is particularly concentrated just above and in front of the crack tip. After the incremental crack advance, this same region that is now unloaded will have a stress distribution that is part of the distribution within the entire area of radius b, but the amount of stored strain energy is lower.

The system allows the user however to find the large strain release just in front of the crack tip during the time it is moving forward. Other programs will find elastic strain energy and its changes in the entire region of radius b shown in FIG. 13 and are discussed later in this section.

Figure 38:
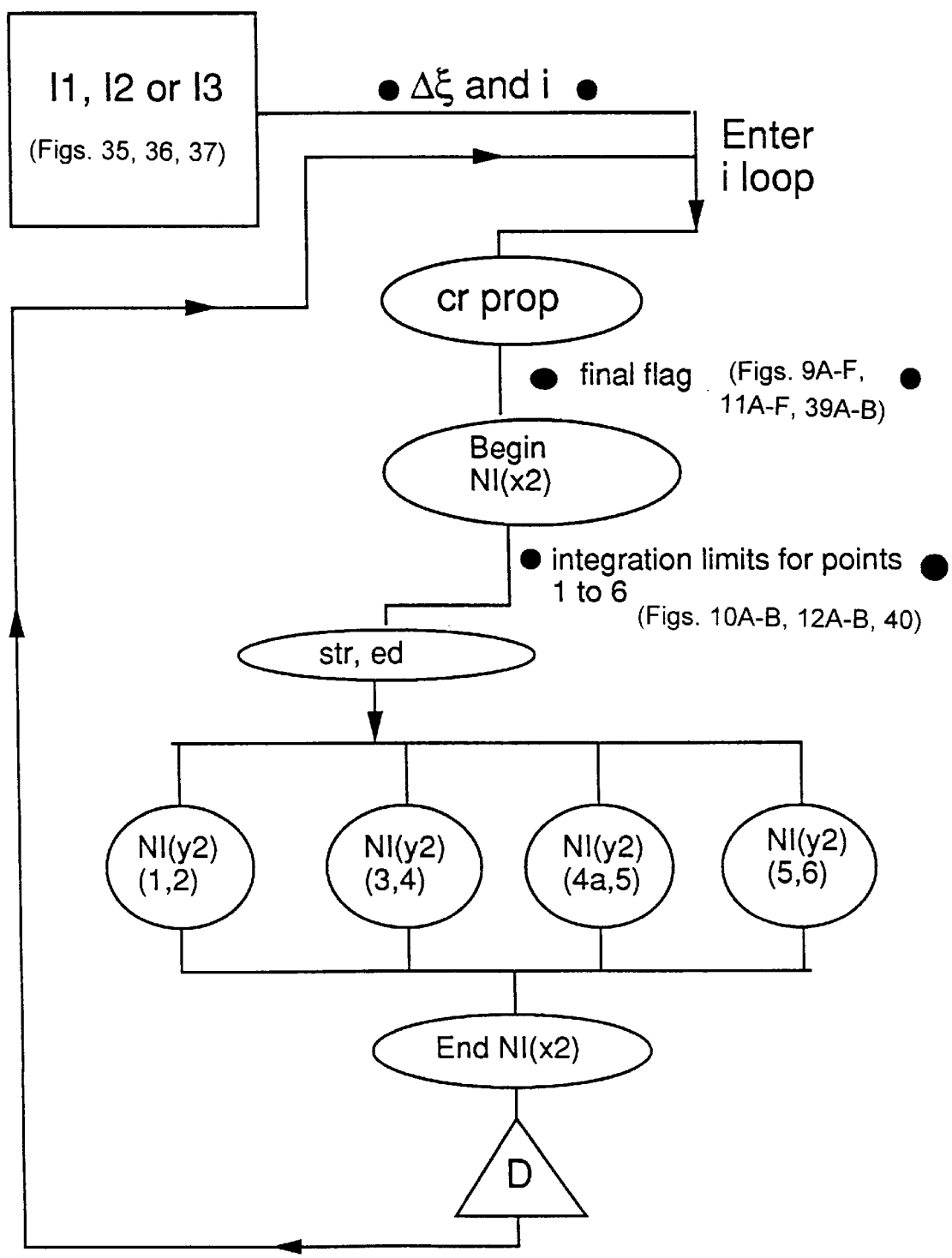
FIGS. 38, 39A, 39B and 40 are flow charts involving energy release just above and below the increment of crack advance.

The flow of software for the strain energy release in the region shown in FIG. 3 is shown in FIG. 38. After the accumulation of basic data, entering the main i loop and calculating the properties abbreviated crprop discussed in section II under Definition and Preparation of Basic Data, it first must be recognized where the crack tip is with respect to the planar microstructural entity. To assess this position, a two digit flag called finalflag is set.

The conditions and flow of software used to set finalflag are shown in FIGS. 9A–9F. FIGS. 9A, 9B and 9C show where the circular region of radius b can be with respect to the planar entity. These three conditions set an initial flag f1 to 0, 1 or 2. f1 begins at 0, which is the case shown in FIG. 9C when there is no overlap between the circular region and the planar entity. For the configuration in FIG. 9B, f1 is 1. For FIG. 9A, f1 is 2.

FIGS. 9D, 9E and 9F show the conditions of the radius of plasticity in material 2 with respect to the planar entity. Although energy absorption for plasticity in material 2 is later calculated within material 2, the radius within which these processes occur is calculated as if the crack were in material 2 and the resulting radius is labeled rpl2 and it is used to set an intermediate flag f2 to 0, 1 or 2. In FIG. 9D, the region of plasticity for material 2 extends into material 2 and f2 is 1. In FIG. 9E, there is no plasticity in material 2 and f2 is 0. In FIG. 9F, the radius of plasticity extends over the second material and back into material 1 and f2 is 2.

Inside the procedure used to set f1 and f2, the variables r1 and r2 are used. r1 is the distance from the crack tip to the nearest edge of the planar entity at an abscissa $\Delta\xi$ in the x2, y2 coordinate system. The x2, y2 coordinate system is a Cartesian coordinate system with an origin 0, 0 at the crack tip, as shown in FIG. 8. r2 is similarly the distance from the crack tip to the more distant edge of the planar entity having the higher ordinate in the x2, y2 coordinate system at the abscissa $\Delta\xi$ in the same coordinate system. The procedures used to calculate the ordinates at the edge of the planar entity at x2=$\Delta\xi$ use d, $\phi$, $\xi$ and $\Delta\xi$ as inputs, use an intermediate angle $((\pi/2)-\phi)$ and the slope of the line representing the interface in the x2, y2 coordinate system.

Returning to FIGS. 39A and 39B, the first five loops are assignments of f1 and f2 as discussed previously with regard to FIGS. 9A–9F. The questions on the left hand side ask how large r1 and r2 are with respect to rpl2 and b to assign f1 and f2. Continuing down the flow chart, when f1 is zero, neither the radius of elasticity b nor the radius of plasticity rpl2 extends into material 2 as shown in FIG. 9C and finalflag is immediately set at 0.

Once f1 and f2 have been assigned, the rest of the flow chart beginning with the question "Is f1=1?" assigns finalflag based upon combinations of f1 and f2. Finalflag is a two digit flag of number 10, 11, 12, 20, 21 or 22. The digit in the ones' place is f2, and the digit in the tens' place is f1. The flag denotes the various combinations of rpl2 and b with respect to material 2.

Continuing down the chart, for example, if f1 is 1 and f2 is 1, the configuration is that of FIG. 9D in which both the regions for elastic strain energy and for plasticity extend into material 2 and finalflag is 11. If f1 is 1 and f2 is 0, finalflag is 10. For this finalflag the region for elastic strain energy overlaps into material 2 but there is no plasticity in material 2. If f1 is 1 and f2 is 2, finalflag is 12 and the situation resembles that of FIG. 9F in which rpl2 extends beyond material 2 and back into material 1, but the radius b within which elastic energy is being calculated is set at a very small value so that the region extends into but not over material 2.

The final part of the flow chart shows the combinations giving a finalflag of 20, 21 or 22 in which material 2 has a small width d and the region of radius b extends over material 2 and back into material 1, as shown in FIG. 9B. When f2 is 1, finalflag is 21 and rpl2 extends a bit into material 2 as in FIG. 9D but with b still extending over material 2 as in FIG. 9B. When f2 is 0, finalflag is 20, and there is no plasticity occurring in material 2. The final combination at the end gives a finalflag of 22 giving the case illustrated in FIG. 9F in which both the regions for elasticity and for plasticity extend over material 2 and back into material 1. At the bottom of the chart at the word "End" finalflag has a value 0, 10, 11 12, 20, 21 or 22.

After finalflag is set in FIG. 38, numerical integration begins with respect to x2 running from 0 to $\Delta\xi$ using Simpson's Rule. The increment for advancement during numerical integration is set at $(\Delta\xi/10)$ but can be adjusted by the user. Once x2 is at a particular value in the numerical integration, it is held fixed within its numerical integration counting loop and inside this loop numerical integration with respect to y2 begins. Before it begins, however, integration limits must be set for y2, which is the next step in FIG. 38.

Figure 10A:
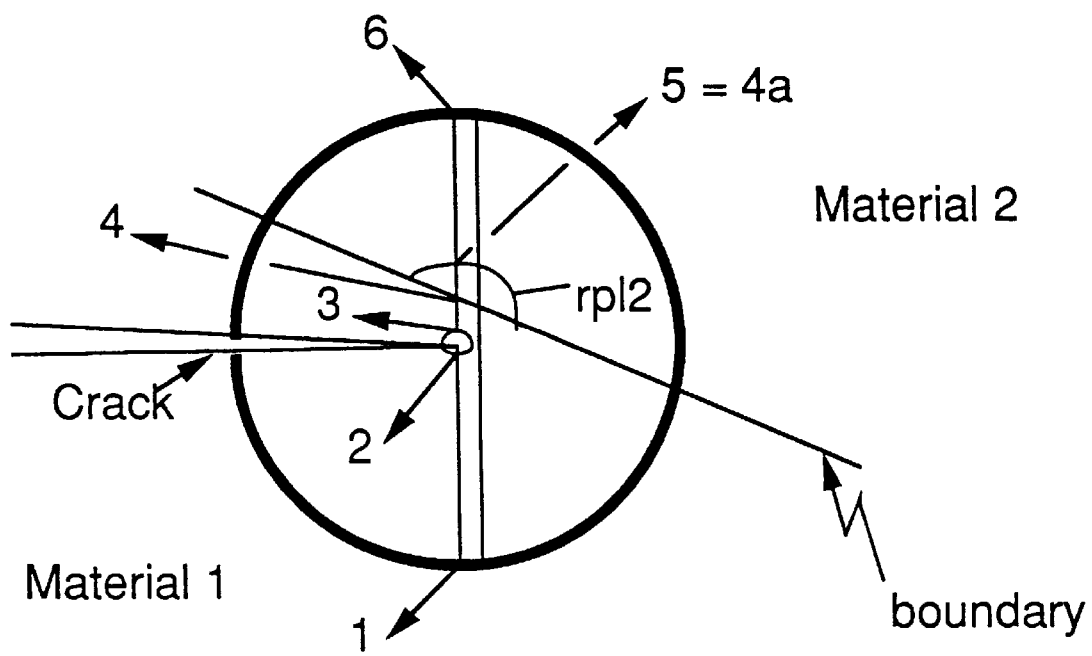
FIGS. 10A and 10B show integration limits for a region of width $\Delta\xi$ for a second material with planar sides.
Figure 10B:
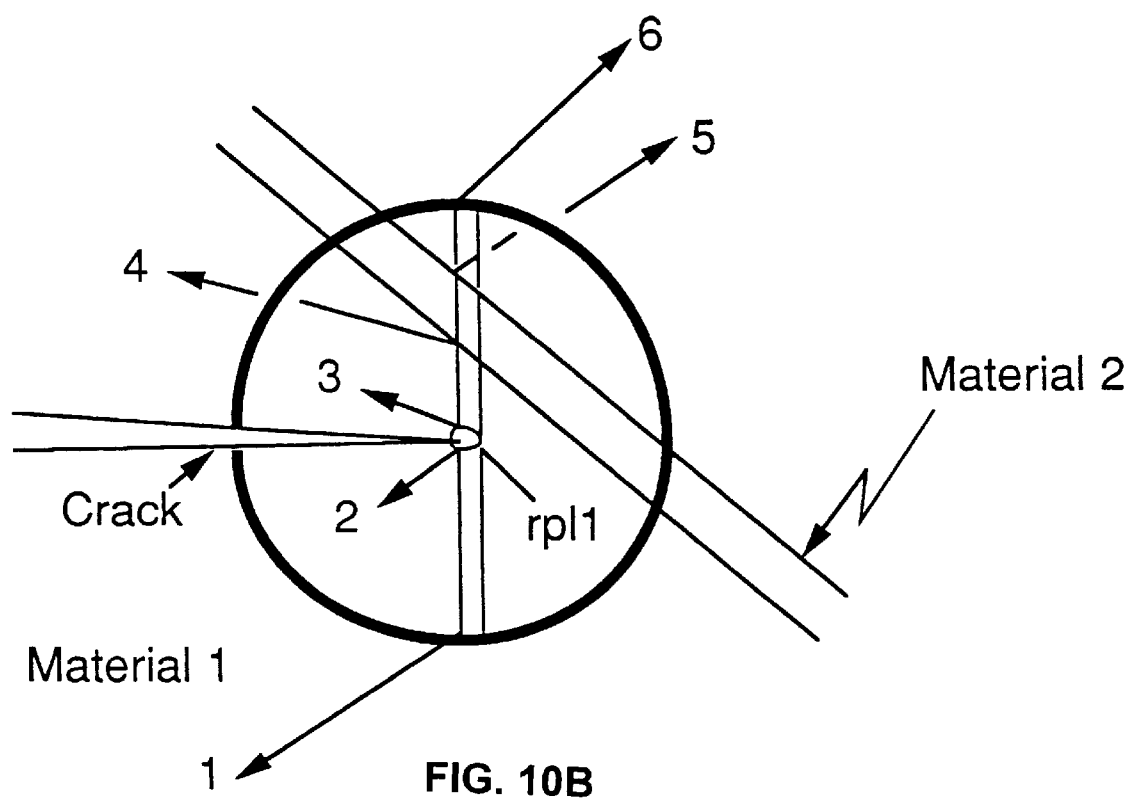

The integration limits for integration with respect to y2 are at points 1 to 6 in FIGS. 10A–10B. The points 1 to 6 are at ordinates in the x2, y2 coordinate system and the integration limits are set by the same conditions used to set finalflag in FIGS. 9A–9F. In other words, final flag is used to set the integration limits.

FIGS. 10A and 10B show two representative cases in which the limits of integration change. If there is plasticity occurring in material 2, the stress is assumed to be beyond the point at which reversible elastic extension occurs. Consequently, in a region where plasticity is occurring, elastic strain energy to be released upon crack extension is not calculated for that region. The limits of integration to obtain elastic strain energy are set accordingly using the finalflag discussed previously in this section.

Points 1, 2, 3 and 6 in FIGS. 10A and 10b are essentially always in the same place. Point 1 lies at an ordinate of –b. Points 2 and 3 lie on a circle indicating a region of plasticity in material 1. The region of plasticity around the crack is always present even if very small so numerical integration for strain energy does not occur there. The radius of the region of plasticity in material 1 is abbreviated rpl1. Point 6 always lies at an ordinate of b.

Figure 39A:
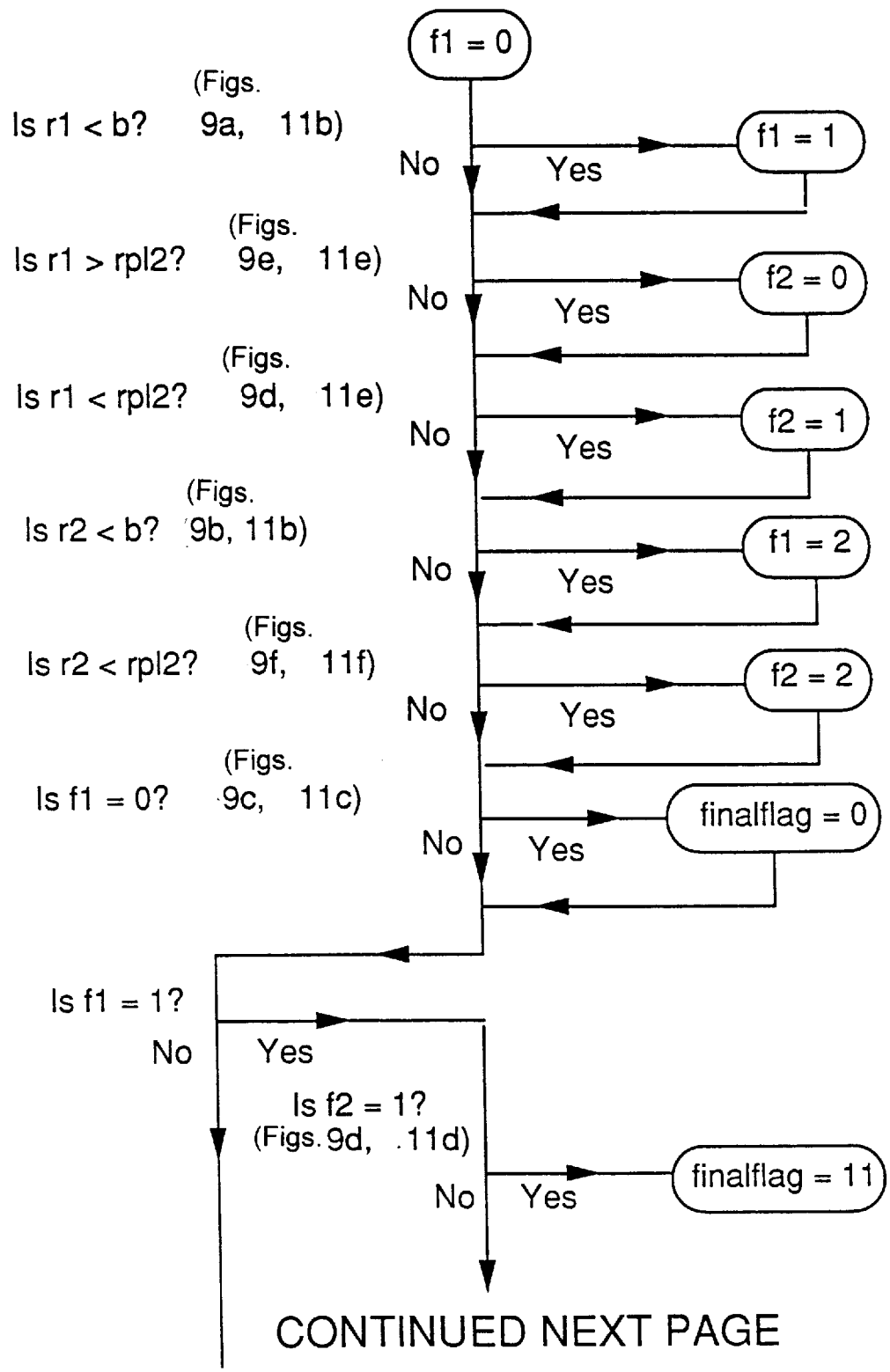
Figure 39B:
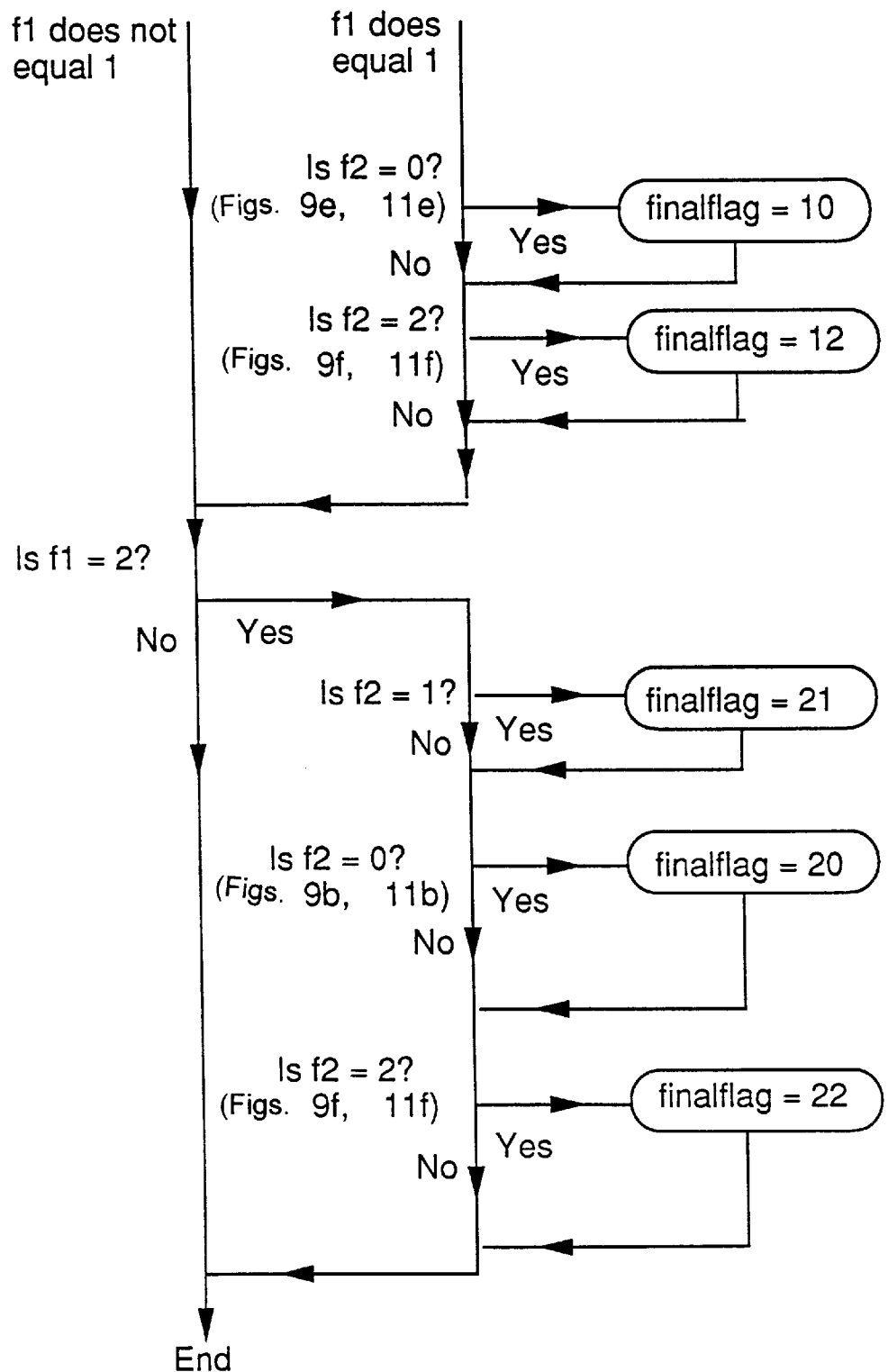
Figure 40:
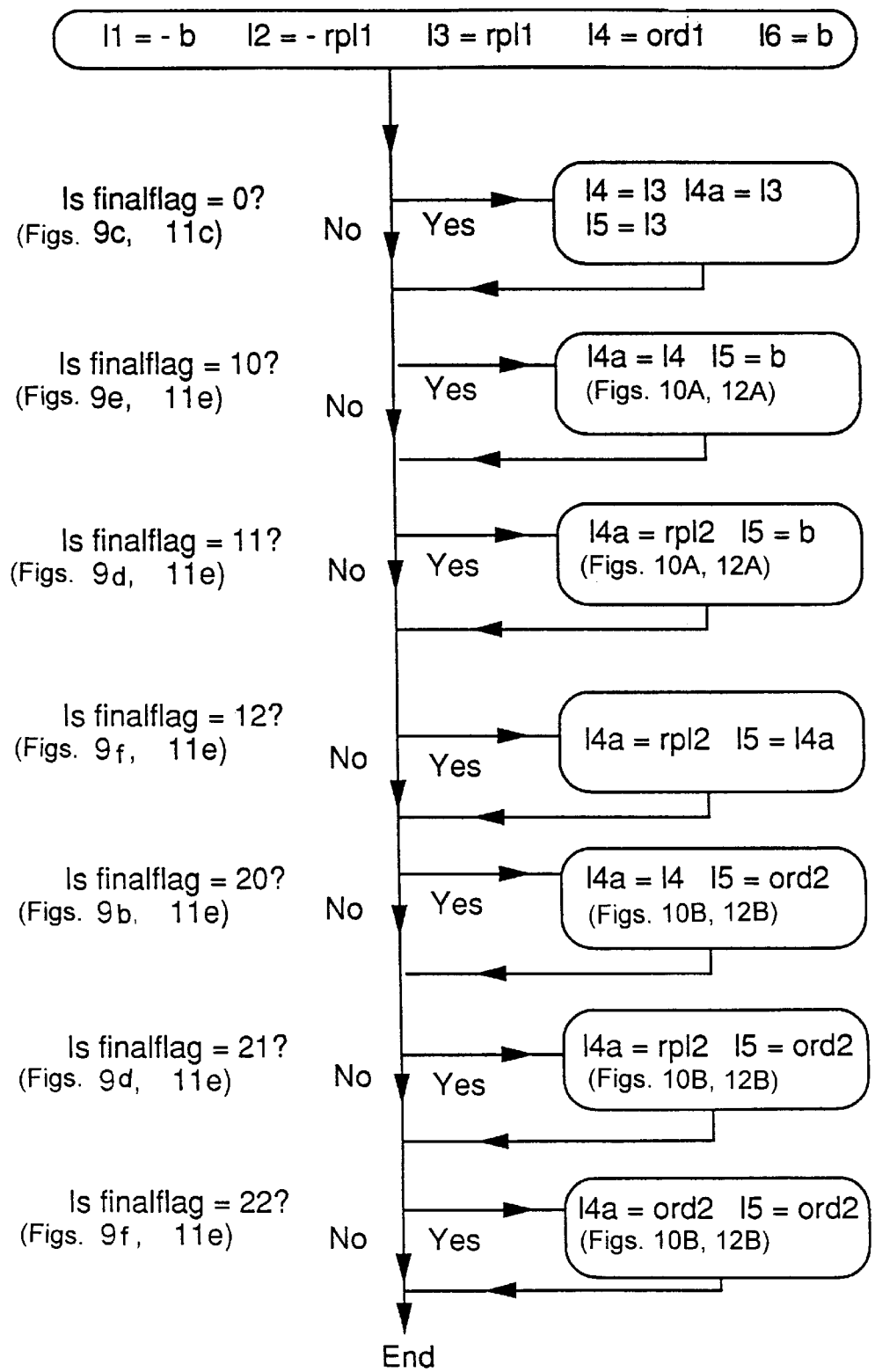

The routines for assigning the integration limits themselves are in FIG. 40. The limits corresponding to points 1 to 6 are labeled I1 to I6 respectively and appear with starting values at the top of the chart. The limits I1, I2, I3 and I6 corresponding to points 1, 2, 3 and 6 are set at the values discussed in the last paragraph and are shown at the top of the chart. The rounded rectangular boxes throughout FIGS. 39A, 39B and 40 correspond to variables and flags being set by simple assignment statements. In the rounded box at the top it is seen that I1 is set at –b, I2 at –rpl1, I3 at rpl1 and I6 at b. I4 corresponding to point 4 in FIGS. 10A and 10B is often at an ordinate labeled "ord1" so it is initially set there. Ord1 is the ordinate in the x2, y2 coordinate system along the line corresponding to the lower interface nearest the crack tip.

I4a is a limit of integration that is an ordinate in the x2, y2 coordinate system that is n the circle of radius rpl2. It is used for integration in material 2 up to the edge of material 2 at I5. When there is no plasticity in material 2, I4a is set at I4 at ord1. When there is a region of plasticity in material 2, it is set on rpl2. Integration for elastic strain energy can then begin at the edge of this region and not include it.

The procedure for assigning ordinates in the x2, y2 coordinate system along the circles with radii rpl1, rpl2 and b use x2, rpl1 rpl2 and b as inputs. The ordinates y2 are found by right triangles formed by rpl1, rpl2 and b with x2.

The next question of FIG. 40, "Is finalflag 10?" corresponds to the situation of FIG. 9E in which there is not plasticity in material 2 but the region of radius b does not extend back over into material 1. In this case, I4a is set at I4 and I5 at b. Integration will then proceed between I3 and I4a in material 1 and between I4a and I5 at the radius b in material 2. As in all cases being discussed, integration will also proceed between I1 and I2 below the crack tip in material 1.

In the third step of FIG. 40, a finalflag of 11 denotes a simple overlap of both regions within rpl2 and b with the material 2 as shown in FIG. 9D. Here I4a is set at rpl2 and I5 at b. Integration will then proceed between I1 and I2 and between I3 and I4 in material 1 and between I4a and I5 in material 2.

A final flag of 12 in the next step would be a situation in which the user has set b to a very small value and the crack tip is near a strip of ductile material so that the circle of radius rpl2 extends over material 2 and back into material 1, as illustrated in FIG. 9F. The circular region of radius b still has a simple overlap into material 2, however, as shown in FIG. 9E. Both I4a and I5 are set at rpl2, the result of which is that integration for elastic strain energy proceeds only between I1 and I2 and between I3 and I4 in material 1.

In the last three steps of FIG. 40, the circle of radius b extends over material 2 and back into material 1. I5 is set at a variable ord2, which is analogous to ord1 except that it is the ordinate in the x2, y2 coordinate system along the line of the interface more distant from the crack tip or the interface with the higher ordinate in the x2, y2 system. Integration for strain energy will proceed in material I between I5 at ord2 and I6 at the circle of radius b.

In the same last three steps in FIG. 40, I4a is then set by the ones' digit of the finalflag. When the digit is 0, there is no plasticity in material 2, as shown in FIG. 9E, and I4a is at I4 or ord1. Integration for elastic strain energy can proceed in material 2 to its fullest extent between ord1 and ord2. With a finalflag of 21, I4a is set at rpl2 so that integration skips the region of plasticity in material 2. In the final possibility at a finalflag of 22, I4a is set at I5 or ord2 so that integration in material 2 between I4a and I5 is given a value of 0.

Once the integration limits for points 1 to 6 have been assigned, the flow chart of FIG. 38 continues downward to show procedures to assign elastic stresses and energy densities. These two sets of quantities are abbreviated "str" and "ed" in the next step for elastic stresses and energy densities. The ellipse around them denotes set of procedures and functions that are for calculations.

Elastic stresses in front of a crack tip[2] are often written in polar or r, θ coordinates. The r, θ coordinate system for the programs herein described has an origin 0, 0 at the crack tip similar to the x2, y2 system, as shown in FIG. 8, and is written parametrically as $x2 = r\cos\theta$ and $y2 = r\sin\theta$. Since other numerical integration elsewhere in the programs is done in polar coordinates for planar shaped entities, one procedure is used to assign a set of elastic stresses around the crack tip in the computer system. Other procedures are then used to convert the r, θ coordinate system to any of the local coordinate systems shown in FIG. 8 for integration in the region at hand.

Just before the setup in FIG. 38 marked str, ed, a procedure sets expressions down that use x2 and y2 as inputs and r and θ as outputs. Pairs of abscissas and ordinates in the x2, y2 system that later get actual numerical values can then be converted to the r, θ system before the elastic stresses are calculated.

The procedure for assigning a set of elastic stresses in front of the crack tip uses r, θ and a total of four stress intensity factors as inputs. The four intensity factors are for both modes I and II for materials 1 and 2. The intensity factors for material 2 will differ from those of material 1 if the user adjusts them earlier to take into account a bimaterial interface as discussed in section IIC titled Assignment of Material Data and Radii of Circular Regions. r, θ and the stress intensity factor for material 1 are used as inputs, for example, to calculate the tensile stresses in the r and θ directions and the shear stress in the θ direction on the plane perpendicular to the r direction[2]. Similar processes are used to give the same three stresses with the three other intensity factors to give a total of 12 stresses as outputs.

The procedure to assign strain energy assigns a strain energy each to mode I and mode II for material 1 and 2 using an expression for strain energy[1] that uses the two tensile stresses in the r and θ directions and the shear stress in the θ direction on a plane perpendicular to the r direction. The energy density from both modes are added together to give a total energy density for each material.

Numerical integration with respect to y2 shown in the next part of FIG. 38 is done using Simpson's Rule. FIG. 38 branches into four sections because numerical integration occurs between all the limits even if one or more get set to zero because the limits are the same, as discussed in the description earlier in this section for FIG. 40.

The function for numerical integration uses pairs of integration limits I1 and I2, I3 and I4, I4a and I5, and I5 and I6 to set the interval of advance of y2 within the numerical integration counting loop. The energy densities are prepared for integration in two dimensions by multiplying by a unit thickness in the third dimension of 1 micron (1 micron=$10^{-6}$ meter). The energy density for material 1 or material 2 as a function of x2 and y2 is then an integrand for the function doing the numerical integration. Between I1 and I2, between I3 and I4, and between I5 and I6 the energy density for material 1 is used. Between I4a and I5 the energy density for material 2 is used.

The results of numerical integration with respect to y2 are added together and used as the integrand as a function of the immediate value of x2 in the loop for numerical integration with respect to x2 that is still continuing. Once numerical integration with respect to x2 is complete, as shown in the next step, the result is a strain energy that can be released just in front of the crack tip within $\Delta\xi$. Since it is an energy quantity being released, it is multiplied by −1 before being stored in a data file in memory. Energy quantities calculated in other programs that are energies that could be absorbed and represent work that must be done within the material for the crack to move forward are stored in memory as positive quantities.

Storage of a result in memory is denoted by a triangle with a capital D inside in the Flow Charts. The arrow extending back to the beginning of the i loop in FIG. 38 means that the process discussed in this section repeats for each increment of crack advance.

Figure 41:
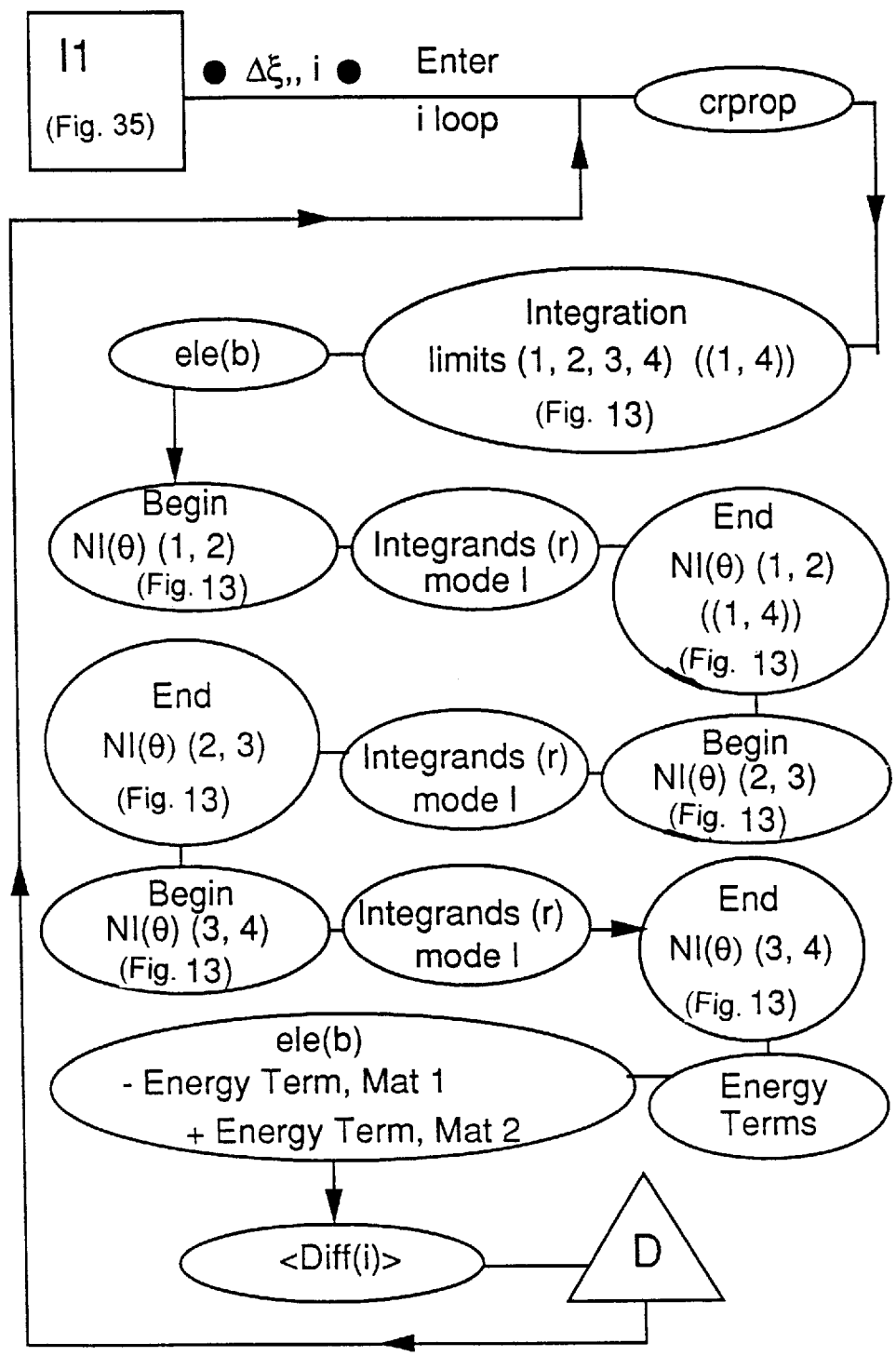
FIGS. 41–45 are flow charts for routines when the second material has planar sides.
Figure 42:
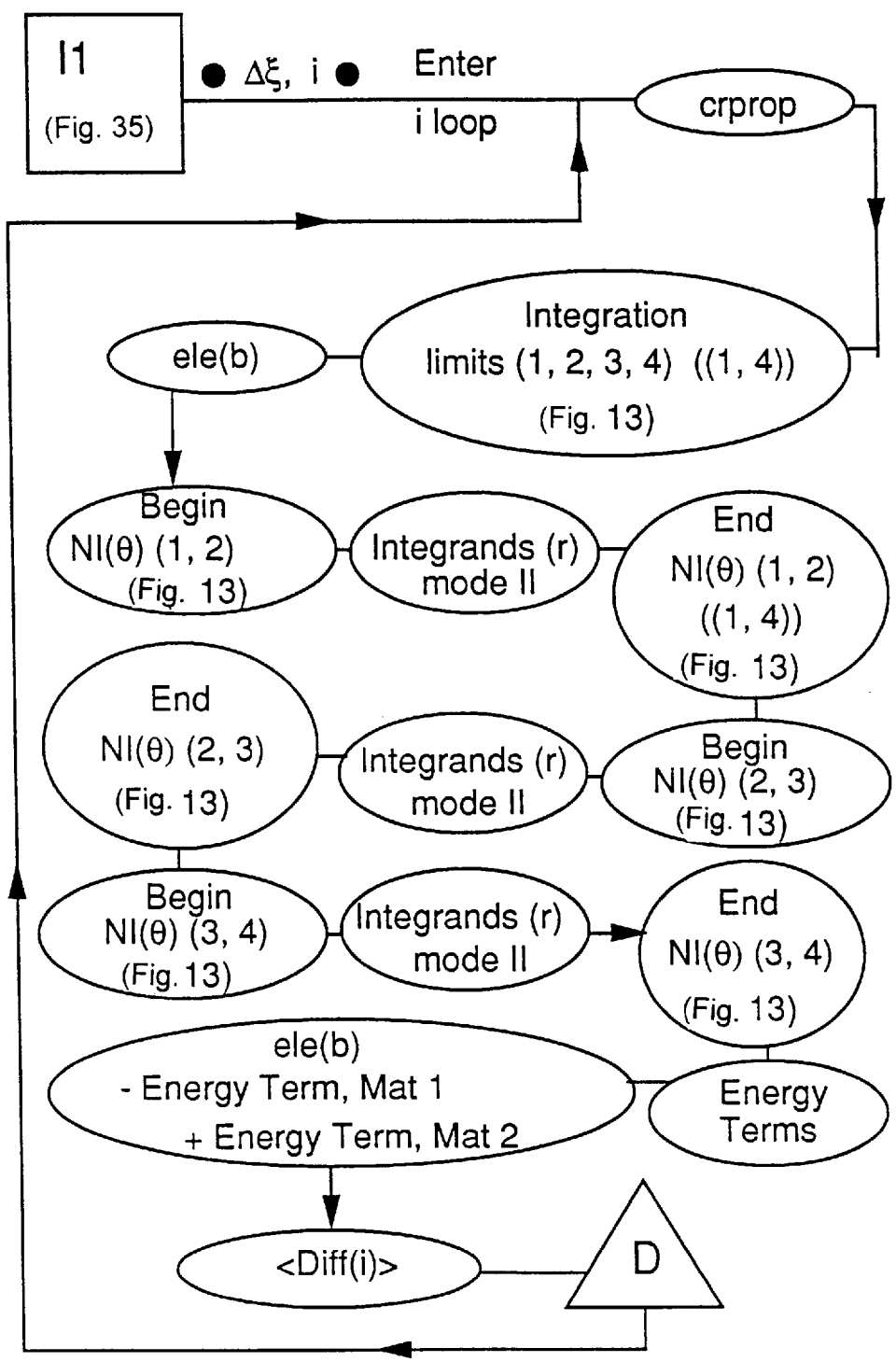

IVA.2. Elastic Strain Energy Changes Within the Entire Circle of Radius b (FIGS. 13, 41 and 42)

This section explains the sequence of software for obtaining elastic strain energy changes in the entire circle of radius b, as shown in FIG. 13. The amount of total strain energy within the circle depends upon the size of the stress intensity factor. The intensity factor in turn depends not only on the size of the applied stress, but also upon the crack length itself, with the intensity factor increasing as the crack length increases. Consequently, when a crack moves forward by a length $\Delta\xi$, the elastic strain energy alone stored around it is greater in the final position when the crack length is $a+\Delta\xi$ than in its initial position with length a.

The programs give a user the alternative of calculating this change in stored elastic energy with each advancement $\Delta\xi$ along with the strain energy released above and below $\Delta\xi$. With some minor adjustments in assignment statements a user can also look at a total release in strain energy within the entire circle of radius b in keeping with more traditional approximate calculations of strain energy release.

The overall procedure that the programs use consists of three steps. The first is that elastic energy is calculated for material 1 within the entire circular region of radius b as if material 2 were not there. It then sets up angular limits of integration where material 2 is and subtracts out strain energy of material 1 in the region where material 2 is. Strain energy of material 2 in the same region is then calculated. These last two steps are actually performed within the same loop for numerical integration with separate but simultaneous summations occurring with various integrands representing strain energy components of materials 1 and 2.

FIGS. 41 and 42 show the flow of software for assigning and storing strain energy within the circular region of radius b. FIG. 42 is very similar to FIG. 41, with the only difference being that strain energy for a mode II component is being calculated. Both charts begin with Inquiry or I1 for short, calculations of $\Delta\xi$ and i, entering the main loop for crack advance and calculating crack properties abbreviated crprop as discussed in section II on Definition and Preparation of Basic Data.

FIG. 13 illustrates the steps taken in FIGS. 41 and 42 after the procedures in crprop. A procedure first calculates strain energy for material 1 within the radius b. Integration in the r, θ coordinate system will then proceed within the region bounded by the lines shown connecting points 1, 2, 3 and 4. Integration to subtract out strain energy in material 1 and add in strain energy of material 2 proceeds between points 1 and 2, between points 2 and 3 and between points 3 and 4. Three numerical integrations are used because the limits, of integration for r change between these points. When the thickness d of material 2 is greater than b, integration will proceed between points 1 and 4.

The calculation of strain energy in material 1 in the entire circle of radius b, labeled "ele(b)" for elastic energy within b in FIGS. 41 and 42, does not necessarily require numerical integration and can be before or after the step marked integration limits. Depending upon the stresses used around the crack tip, once they have been assigned[2] and strain energy[1] calculated, it can be possible to integrate r from rpl1 to b and θ from 0 to 2 π analytically. r begins at rpl1 or the radius of plasticity in material 1 because there is some plasticity around the crack tip even if rpl1 is in angstroms because the concentrated stresses there will exceed the yield stress at which plasticity begins to occur in the material. The procedure to assign ele(b) uses b, v1, E1, G1 rpl1 and the stress intensity factor for mode I in material 1 as inputs. It assigns the strain energy by using an expression found analytically by integrating an expression for strain energy[1] from elastic stresses[2] in polar coordinates. In the integration r extends from rpl1 to b and θ extends from 0 to 2 π.

The step labeled integration limits refers to angles for the θ coordinate in the r, θ coordinate system between the line of the crack path and the lines between the crack tip and points 1, 2, 3 and 4. Angletest is a preliminary variable for φ in degrees that checks to see if the crack is approaching the entity at a right angle.

Another variable, $\xi_2$, assigned as $\xi+(d/\cos\phi)$, is the distance along the crack path to the more distant side of the entity from the crack tip. The functions for the polar angle to points 1 and 4 use angletest, b, $\xi$ and φ as inputs and are calculated geometrically. The functions for the angles to points 2 and 3 use angletest, b, φ and $\xi_2$ as inputs and are calculated in a similar manner.

The integrands(r) modes I and II in the middle of FIGS. 41 and 42 are integrands for both materials 1 and 2 that are strain energy densities as a function of θ. They are found the same way as those for the mode I and mode II integrands used to find ele(b) discussed earlier in this section. They are found by using expressions for stresses in polar coordinates near the crack tip and equations for strain energy density. While holding θ fixed, it is easy to integrate with respect to r between the two lines representing the interface and between the line along the interface and the radius b. The integrands afterwards are then only functions of θ. The "(r)" next to the integrands denotes that they have already been integrated with respect to r. They are assigned negative values for material 1 and positive values for material 2 so that strain energy for material 1 is subtracted out and strain energy for material 2 is added in.

The resulting numerical integration is done with respect to θ and is abbreviated NI(θ) in the Charts. When d is much greater than b, integration proceeds between points 1 and 4. When it is less than b, as shown in Drawing 13, integration begins and ends as shown in the Charts between points 1 and 2, between points 2 and 3 and between points 3 and 4.

The results of the integration are combined with elastic constants to produce final energy terms under the step labeled Energy Terms. The term calculated for material 1 in the region for material 2 is subtracted out of the energy for the entire circular region and the energy term for material 2 is added in as discussed previously and shown in the next step of the chart. The difference of this entire energy term is taken between two adjacent increments of the crack and the result is stored in memory as shown. The top of the main loop is then begun again for the next crack position and the steps and calculations discussed in this section are repeated.

IVA.3 Plasticity in Materials 1 and 2 for an Entity With Planar Sides (FIGS. 14–16 and 43–45)

In regions in which the stresses exceed the yield strength of either material 1 or 2, yielding or plasticity is expected to occur. These are processes that absorb energy and will lead to positive values for energy stored in the data files in memory. If some process other than plasticity is occurring to absorb energy in material 2, a user can set the radius within which the process occurs and type in an expression(s) for the energy in the appropriate place in the program calculating plasticity in material 2.

There will be some plasticity in a region about the crack tip in material 1 even if the region is very small. The programs take this into account by recognizing where this region is with respect to the interface between materials 1 and 2, by calculating the appropriate amount of energy for plastic work in material 1 for each increment of crack advance and by storing the result in the appropriate data file.

Figure 14:
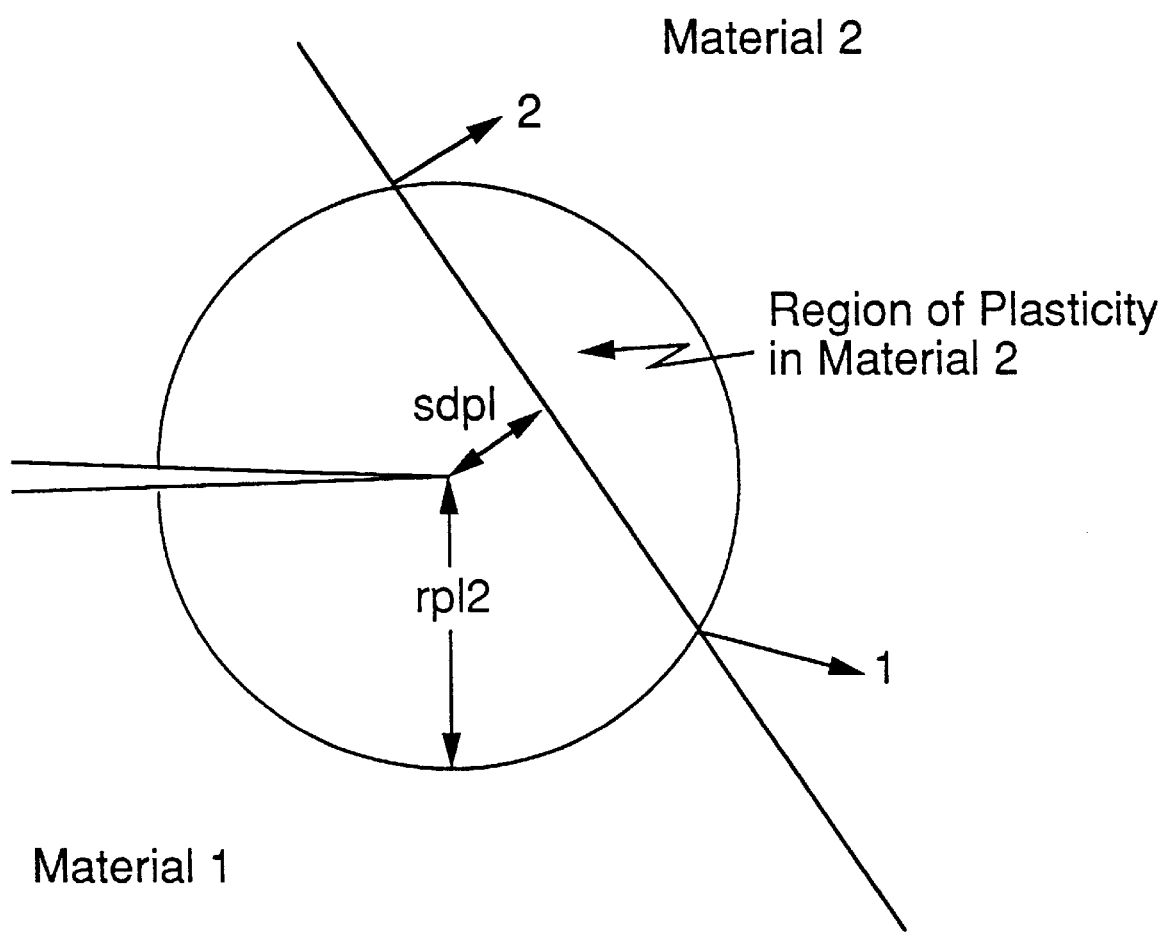
FIG. 14 shows parameters used to determine plasticity in a material when the material has planar sides.
Figure 15:
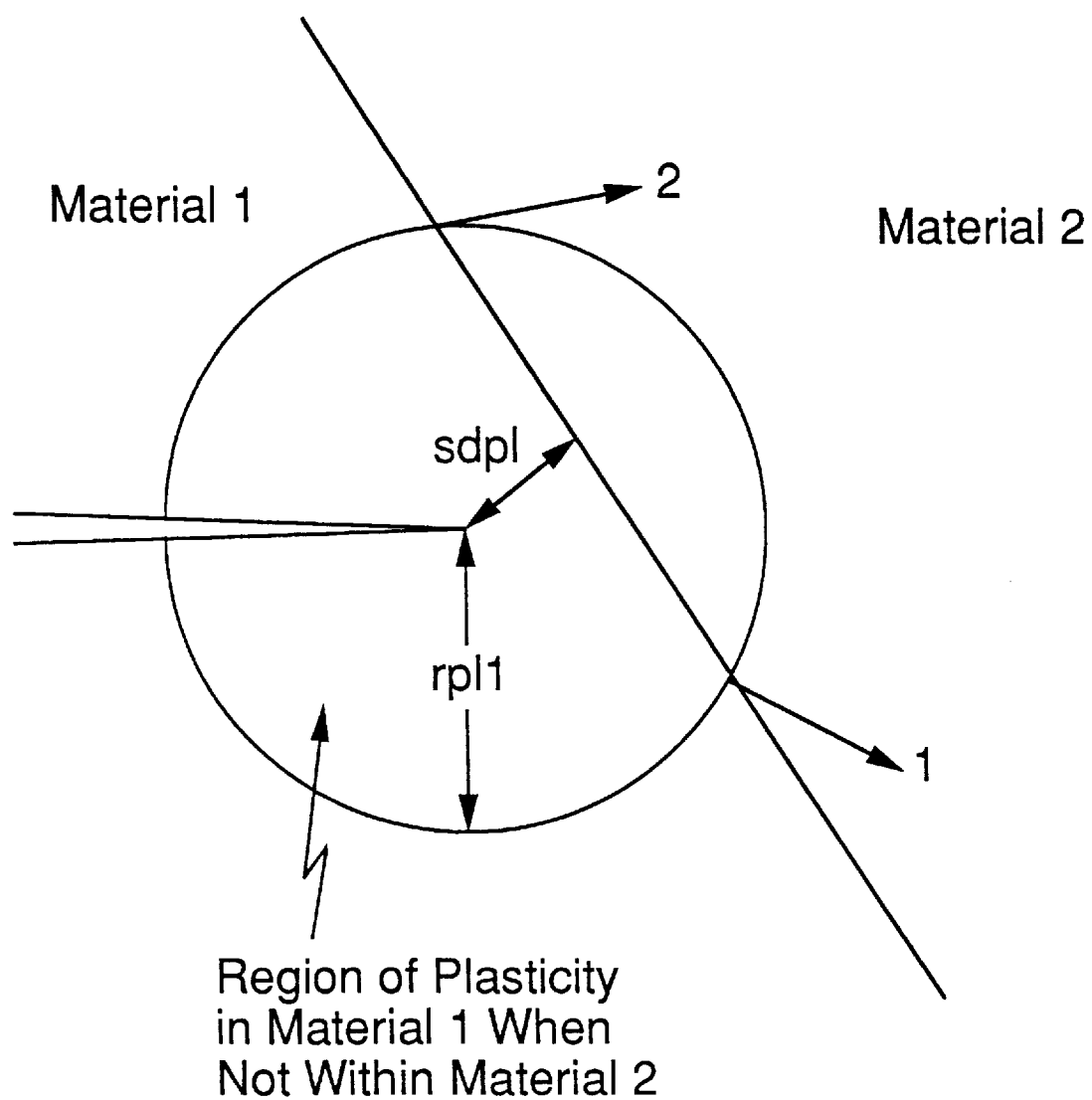
FIG. 15 shows a region of plasticity in a first material when a second material has planar sides.
Figure 16:
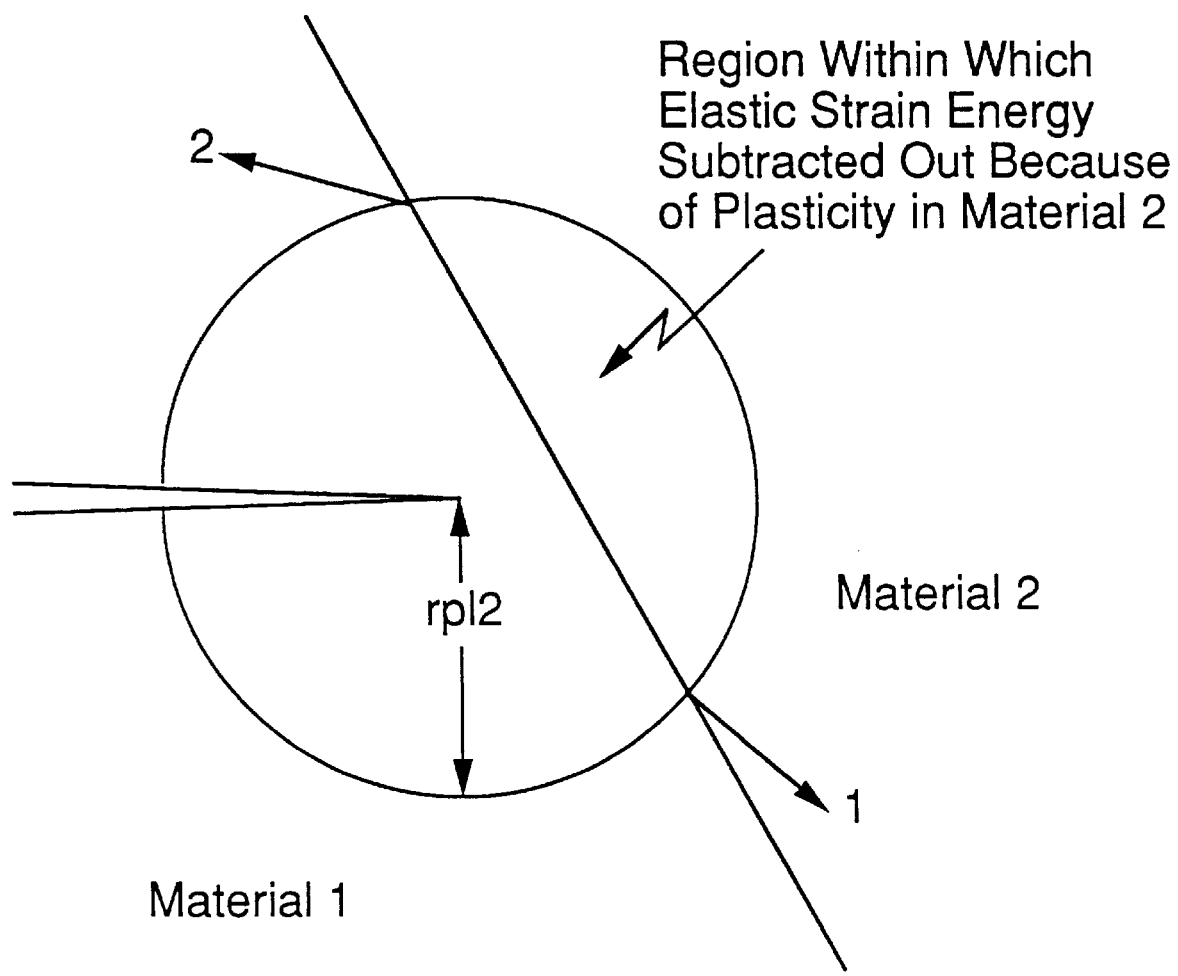
FIG. 16 shows a region of plasticity in a second material when the second material has planar sides.

FIGS. 14, 15 and 16 illustrate the processes that the programs use to take into account plasticity or some other energy absorbing process. FIG. 15 shows how plasticity in material 1 discussed in the last paragraph is accounted for. When the crack is not near the interface, plastic work in material 1 will be calculated within the entire circular region of appropriate radius for material 1 abbreviated rpl1 in the figure. rpl1 can be set by the user or is automatically calculated as described in the section IIC entitled "Assignment of Material Data and Radii of Circular Regions".

The programs recognize whether the crack tip is near the interface by calculating the shortest distance to the interface affecting an amount of plasticity, abbreviated "sdpl" in FIGS. 14–16. For an entity with planar sides, sdpl is simply $\xi\times\cos\phi$, and for plasticity in material 1 it is compared with rpl1. When sdpl is less than rpl1, numerical integration occurs to subtract out plasticity in material 1 between points 1 and 2 in the region where material 2 is in FIG. 15.

If plasticity is occurring in material 2, elastic strain energy calculated previously in the region is first subtracted out, as shown in FIG. 16. The programs will recognize where the crack is with respect to a region where elastic strain energy must be subtracted out and numerically integrated between points 1 and 2 to find the strain energy computed earlier in another program in the region in Drawing 16. If a user is looking at an energy absorbing process other than plasticity that does not require elastic strain energy to be subtracted out, a user may elect not to run the 80 series programs and keep the values in the appropriate data file for energy subtraction at zero.

FIG. 14 then shows the same region in the corresponding FIG. 16 where plasticity is occurring in material 2. The programs will evaluate this term if present for each increment of crack advance by calculating sdpl, comparing it with rpl2, the radius within which plasticity in material 2 occurs, and numerically integrating over the region between points 1 and 2. rpl2 may be set by the user or is automatically calculated from other parameters as described in section IIC entitled "Assignment of Material Data and Radii of Circular Regions".

Figure 43:
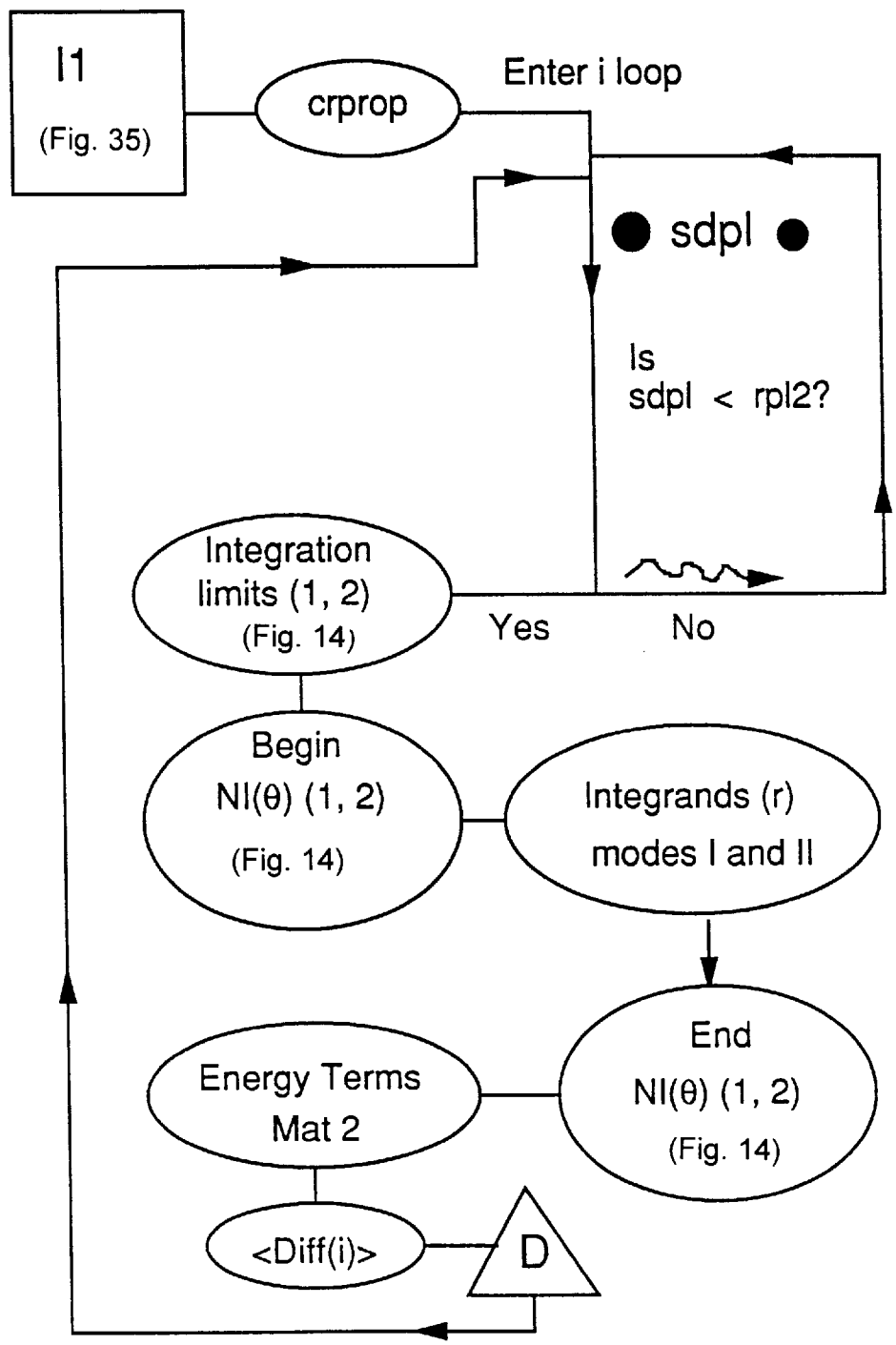
Figure 44:
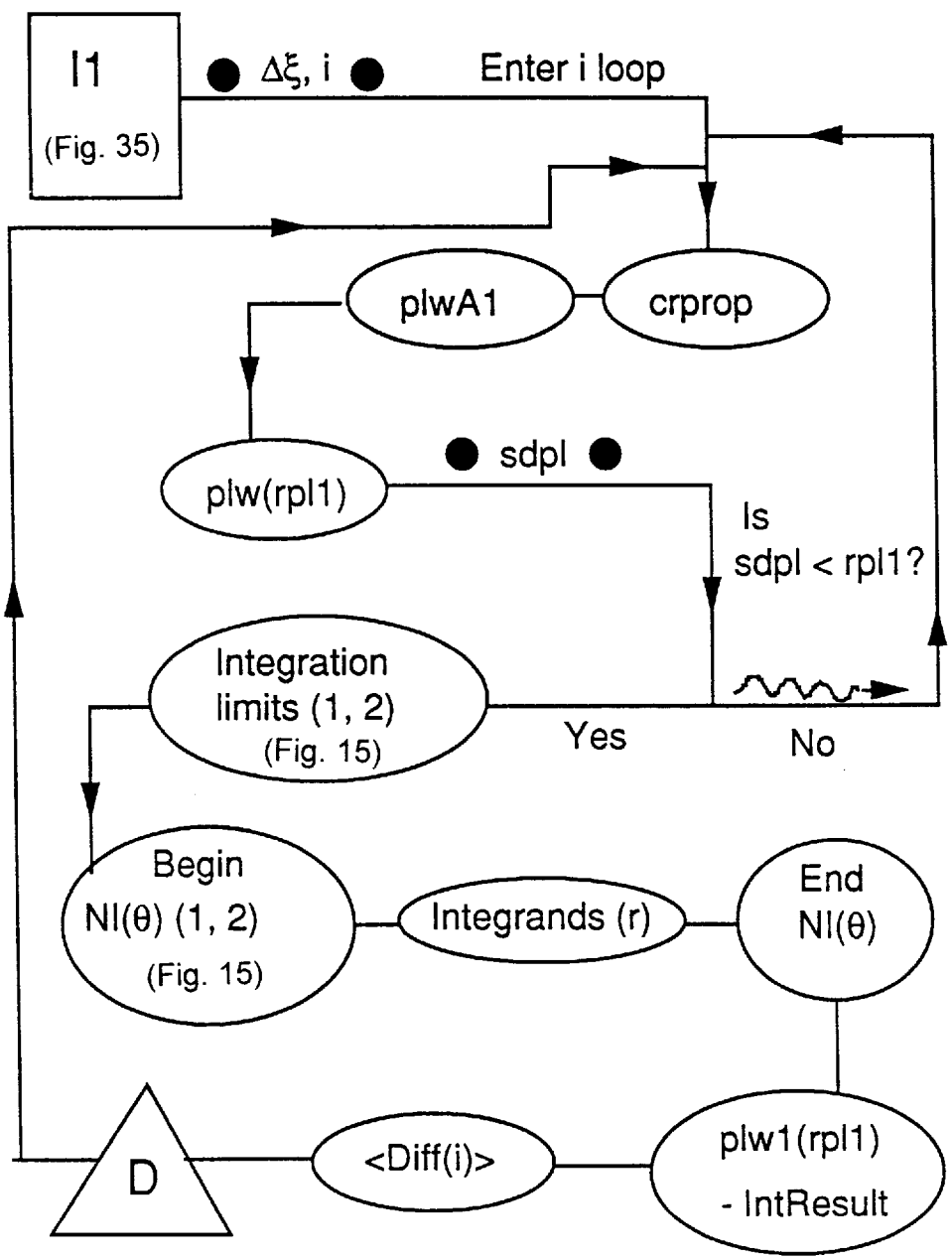
Figure 45:
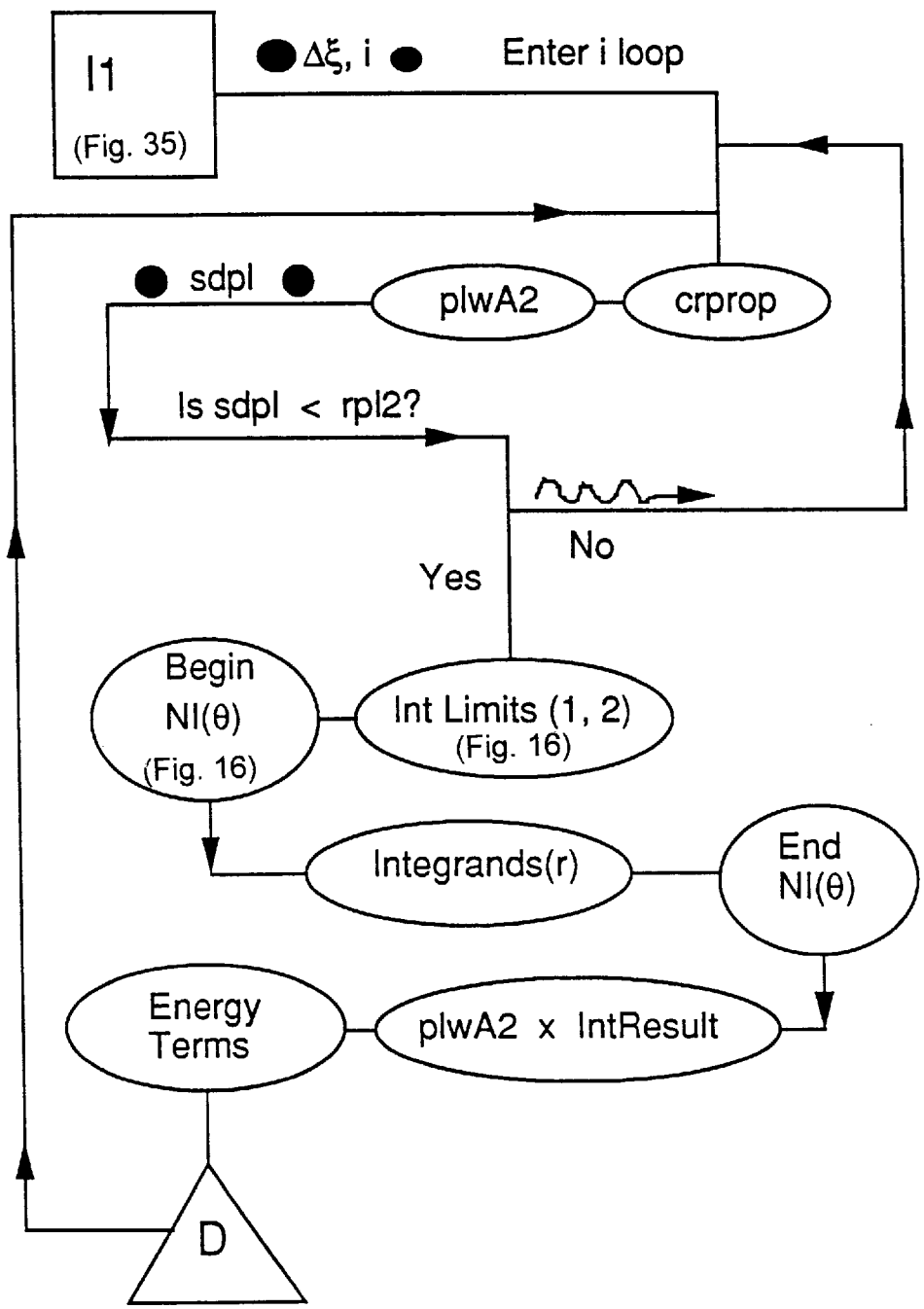

FIGS. 43–45 show the flow of software for obtaining the positive energy quantities resulting from energy absorbing processes. Each begins with Inquiry 1 or I1 and crprop shown in more detail in FIG. 35 to set up geometric and material parameters as described in sections IIB and IIC under Basic Geometric Parameters and Assignment of Material Data and Radii of Circular Regions. After the main loop is entered for crack advancement, sdpl is calculated and compared appropriately with rpl1 or rpl2 to check for overlap of a region into material 2. If sdpl is greater than rpl1 or rpl2 appropriately, no overlap occurs and the program proceeds to the next crack increment. The arrow with a wavy line means that some condition for overlap is not met when recognizing where the crack is and the crack is moved to the next position without storage of a result in memory.

If there is plasticity in material 2, FIG. 43 continues to the left at the word "Yes". Angular integration limits in the r, θ coordinate system are then calculated between points 1 and 2 as described in section IVA.2 entitled "Elastic Strain Energy Changes Within the Entire Circle of Radius b". As described in more detail in the same section, numerical integration with respect to θ begins, the integrands for strain energy density are integrated over the appropriate region. Results are combined with elastic constants and kept at a positive number to "subtract" them from the negative values being stored in another data file. Again, the energy can be calculated for each crack position or differences taken between successive crack positions.

FIG. 45 shows a similar process for assigning plastic work in material 2 in the same region as just discussed for FIG. 43. The term "plwA2" refers to plastic work per unit area in material 2, and if it is not a function of r and θ, it can be assigned after procedures for crack properties (abbreviated crprop). A simple approximation would be a dislocation density multiplied by the yield stress, all multiplied by a unit thickness of 1 micron, which is then multiplied by an estimated portion of the Burger's vector for a displacement during plastic work. It is here that some users would want to put in a variety of models and if the work term were a function of θ, a user would put an expression for it in the step marked Integrands(r).

Otherwise, the integrands are used to get areas that will then be used to calculate an area either between points 1 and 2 or within an area between points 1, 2, 3 and 4 as in FIG. 13 if appropriate. From an element of area in two dimensions rdθdr in polar coordinates, these integrands can be independent of θ when θ is held fixed and are $r^2/2$ after integration, in which r runs between the lines denoting the interface and the radii of plasticity as appropriate. The procedure to assign the integrands therefore uses θ, ξ, ξ2, φ, rpl2 and rpl1 as inputs and returns 0.5 times the square of rpl2 minus the square of r along the left interface, 0.5 times the square of rpl1 minus the square of r along the left interface, and 0.5 times the square of r at the right or more distant interface from the crack tip minus the square of r at the left interface. These three variables returned are used as appropriate in the programs.

In FIG. 44, plastic work in material 1 is assigned in a manner similar to the previous discussion in this section. The only difference is that the work is calculated in the entire region of radius rpl1 first and is abbreviated plw(rpl1). The step plwA1 is plastic work per unit area in material 1 if needed. The result from integration near the bottom of the Chart marked "IntResult" is then subtracted from plw1 (rpl1). In the case in which the circular region never overlaps into material 2, a program calculates plw1(rpl1) and stores it in the data file for plastic work in material 1 for each crack position. A complete circuit in FIG. 44 would produce quantities that would change these values in some or all positions in the data file.

IVB. Crack Advancement Toward an Elliptically Shaped Entity

IVB.1. Energy Release Above and Below the Increment of Width Δξ (FIGS. 11A–F, 12A, 12B, 18, 38, 39A, 39B and 40)

Figure 11A:
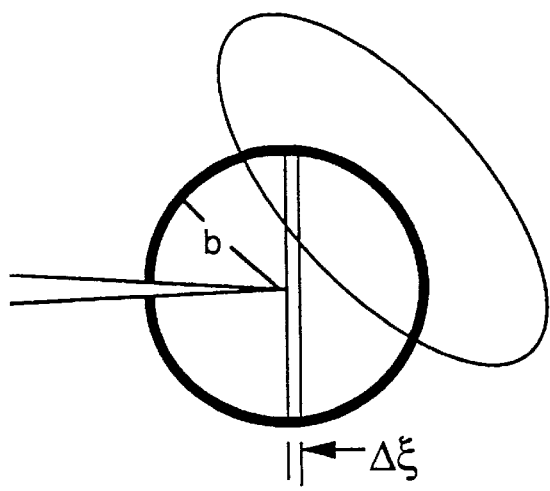
FIGS. 11A–11F show positions of radii of plasticity and of elasticity with respect to an elliptically shaped entity used to set the value of finalflag.
Figure 11B:
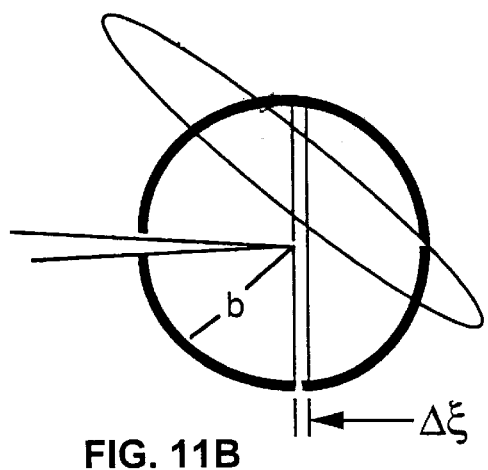
Figure 11C:
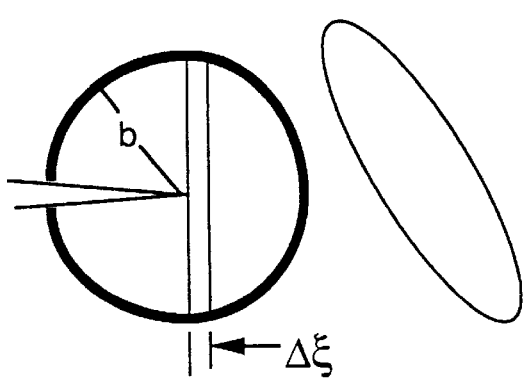
Figure 11D:
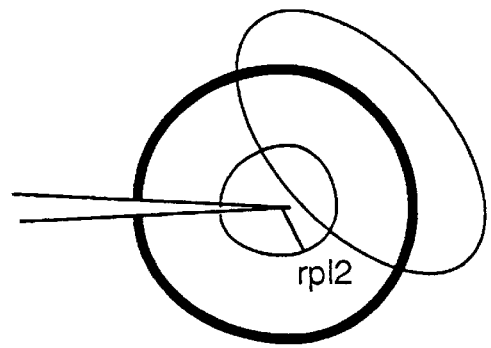
Figure 11E:
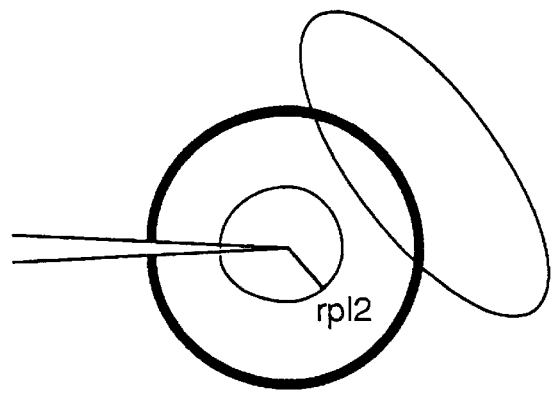
Figure 11F:
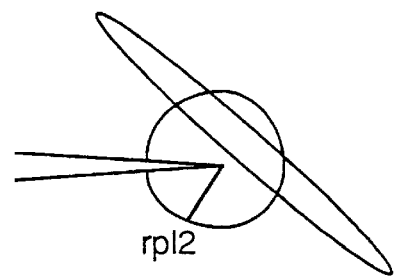
Figure 12A:
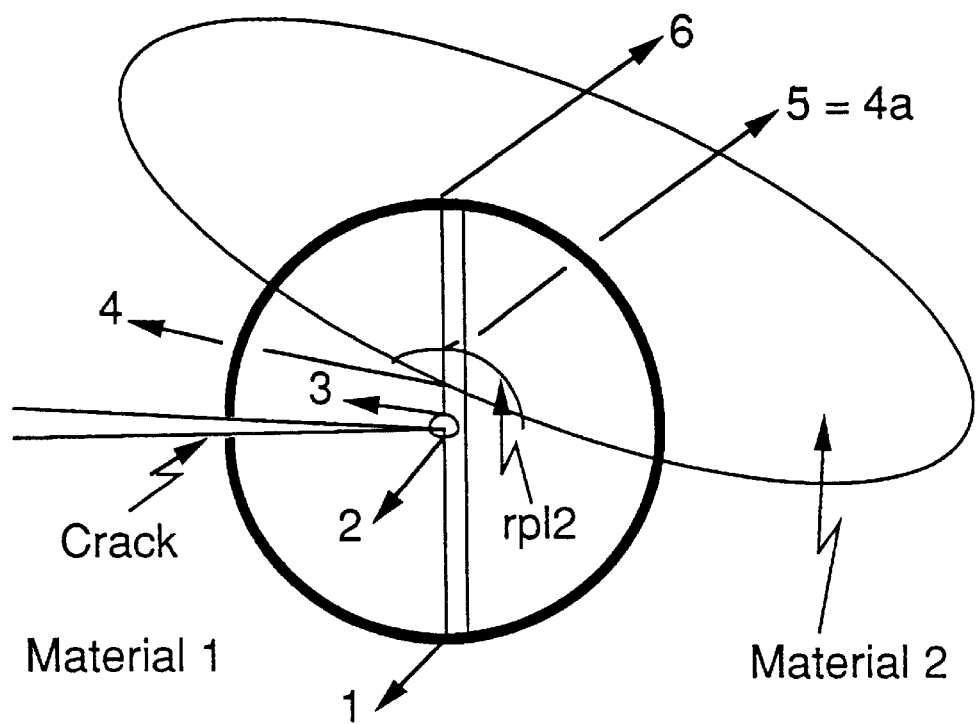
FIGS. 12A and 12B show integration limits for a region of width $\Delta\xi$ for a crack approaching an elliptically shaped entity.
Figure 12B:
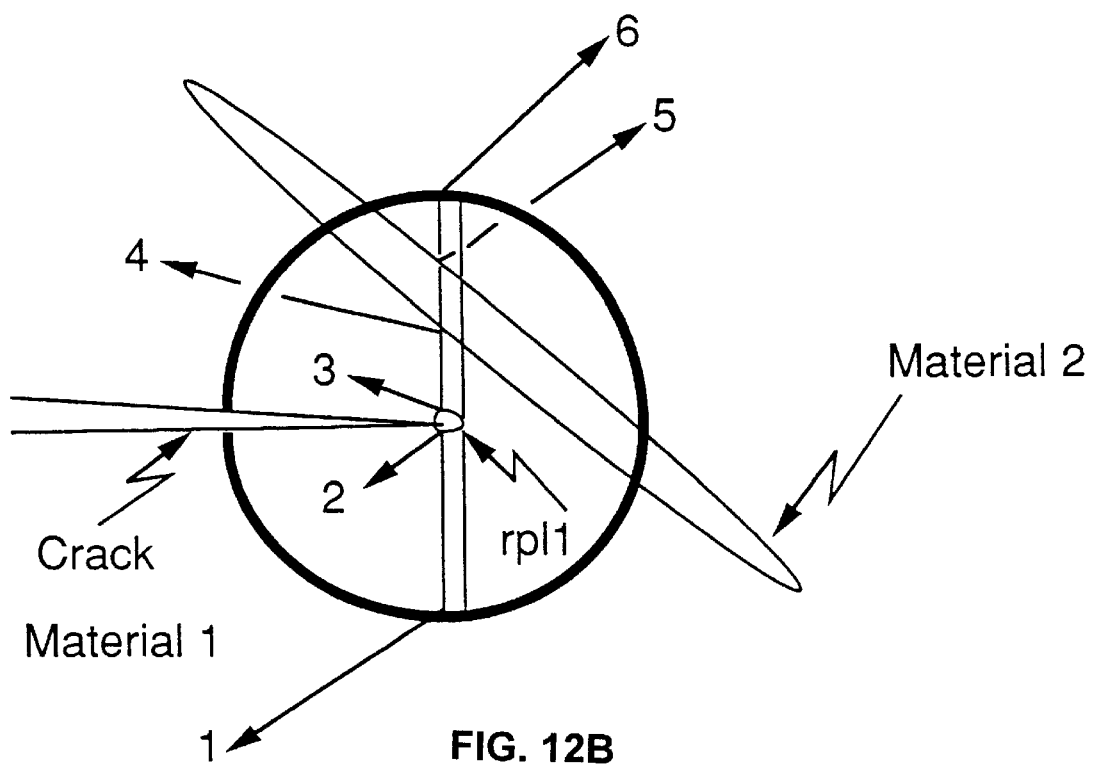

The program to assign energy release just above and below the increment of advance Δξ works in a manner very similar to that of a planar shaped entity. It uses the same flow of software as in FIGS. 38, 39A, 39B and 40, and as discussed in section IVA.1 FIGS. 11A–11F show the same conditions used to set finalflag as in FIGS. 9A–9F except that r1 and r2 now extend to the edge of the ellipse instead of the edge of a planar entity. Similarly, FIGS. 12A and 12B show the points 1 to 6 used to assign the integration limits I1 to I6, the only difference being that points 4 and 5 can lie on the edge of the ellipse instead of a planar entity.

To assign the ordinates in the x2, y2 coordinate system on the edge of the ellipse and to assign later in other programs the shortest distance between the crack tip and ellipse, the coefficients in the polynomial equation for the ellipse in the x2, y2 coordinate system are used. The process of assigning the coefficient is abbreviated "coeff" in FIGS. 48, 55 and 56. For the program to assign energy release in the region of width Δξ, the calculation of the coefficients takes place inside the procedure to set finalflag.

The coefficients for the equation of the ellipse are obtained by transforming the equation for the ellipse in its local x', y' coordinate system to the x2, y2 coordinate system. Both these coordinate systems are shown in FIG. 8. The equation for the ellipse may be written in the x', y' coordinate system as $(x'^2/j^2)+(y'^2/k^2)=1$. Combining this equation with equations to transform the coordinate systems from one to the other, namely $x'=(x1\cos\phi)+(y1\sin\phi)$, $y'=-x1\sin\phi+y1\cos\phi$, $x1=x2-g$ and $y2=y1-c$, one obtains an equation $c1(x^2)+c2(y2^2)+c3(x2)+c4(y2)+c5(x2y2)+c6=0$ for the ellipse. The coefficients refer to c1, c2, c3, c4, c5 and c6 in this equation.

Of the procedures to assign the coefficients c1 to c6, that of c1, c2 and c5 uses k, j, φ and c as inputs and that of c3, c4 and c6 uses k, j, φ, g, c, c1 and c2 as inputs. k, j, φ, g and c are geometrical parameters that are defined and discussed in section II and shown in FIGS. 6, 7A and 7B. When the entity does not intersect the crack path, g is set at ξ, as shown in FIG. 7B. When the entity does intersect the crack path, as shown in FIG. 7A, g is calculated by its own function that uses ξ, k, j, c, c1, c2 and c5 as inputs and solves for x1 along the line of the crack path where y2 is 0. The sequence coeff—g—coeff in FIGS. 48, 55 and 56 and done in the program for an elliptically shaped entity for energy release within Δξ refers to these procedures to assign c1, c2 and c5, assign g, and then assign c3, c4 and c6.

The function to assign the ordinates finally in the x2, y2 coordinate system use the coefficients c1, c2, c3, c4, c5 and c6 and the immediate value of x2 as inputs. The equation for the ellipse in the x2, y2 coordinate system is solved for y2 with the solution giving two values for y2, one with a higher y2 ordinate on the upper end of the ellipse and one with a lower y2 ordinate on the lower end of the ellipse. The function returns as outputs these two y2 ordinates.

Before r1 and r2 are calculated and the routines in FIGS. 39A, 39B and 40 are begun to set finalflag and integration limits, another set of quantities is calculated. These are the abscissas in the x2, y2 coordinate system for the critical points on the ellipse where the slope along the ellipse dy2/dx2 is either zero or infinity, which are labeled as the points c1, c2, c3 and c4 in FIG. 18. The functions that assign them use the coefficients c1 to c6 as inputs and the equation for dy2/dx2 for the ellipse. The equation has values of x2 where dy2/dx2 itself is infinity or is set to 0 and x2 is solved for. The points are used to keep track of where the crack is when setting finalflag, to divide the circumference of the ellipse into sections when pinpointing intersection points between one of the circles and the ellipse, and to set initial points away from the critical points before beginning a Newton-Raphson method to find intersection points. These other processes involving intersection points are discussed later in sections IVB.5 and IVB.6.

Figure 18:
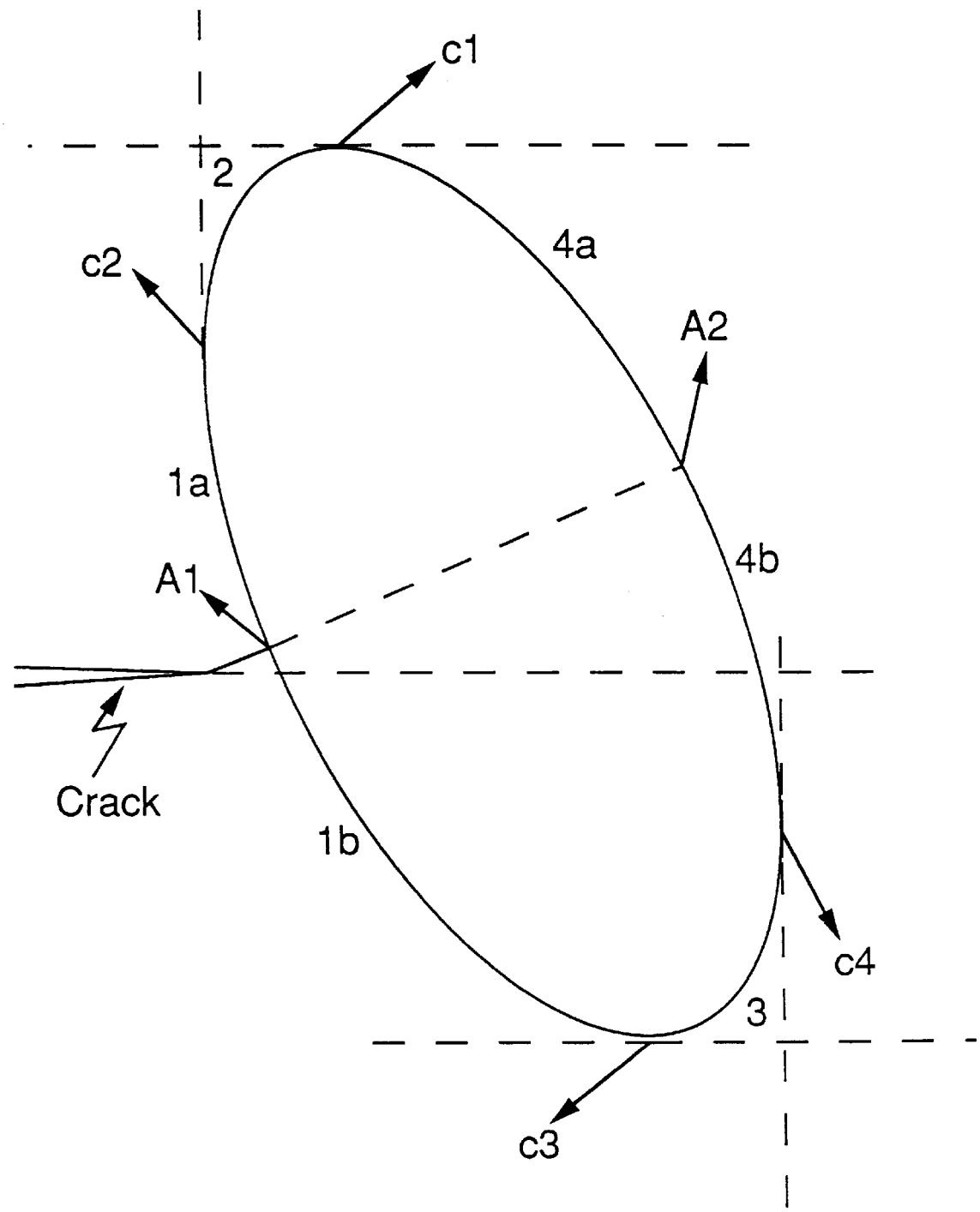
FIG. 18 shows critical points and a region for intersection points on the ellipse.

The program for strain energy just in front of the crack tip within $\Delta\xi$ recognizes where the crack tip is by asking if the immediate value of x2 during integration is less than the abscissa of the critical point c2 in FIG. 18. c2 is the point with the smaller abscissa in the x2, y2 coordinate system where the slope is infinity. If it lies to the left of the point, integration with respect to y2 will not involve material 2, as shown in FIG. 11C. Finalflag is accordingly set to zero.

Otherwise when x2 is greater than the abscissa of point c2 in FIG. 18, one of the situations in FIG. 11A, 11B, 11D or 11F will occur. r1 and r2 will then be calculated and assignment of finalflag according to the flow of software in FIGS. 39A and 39B takes place. Finally, the limits I1 to I6 corresponding to points 1 to 6 in FIGS. 12A–12B will be assigned according to the routines in FIG. 40. Strain energy will be calculated and stored in memory as shown in FIG. 38 and discussed for a planar entity in section IVA.1.

Figure 17:
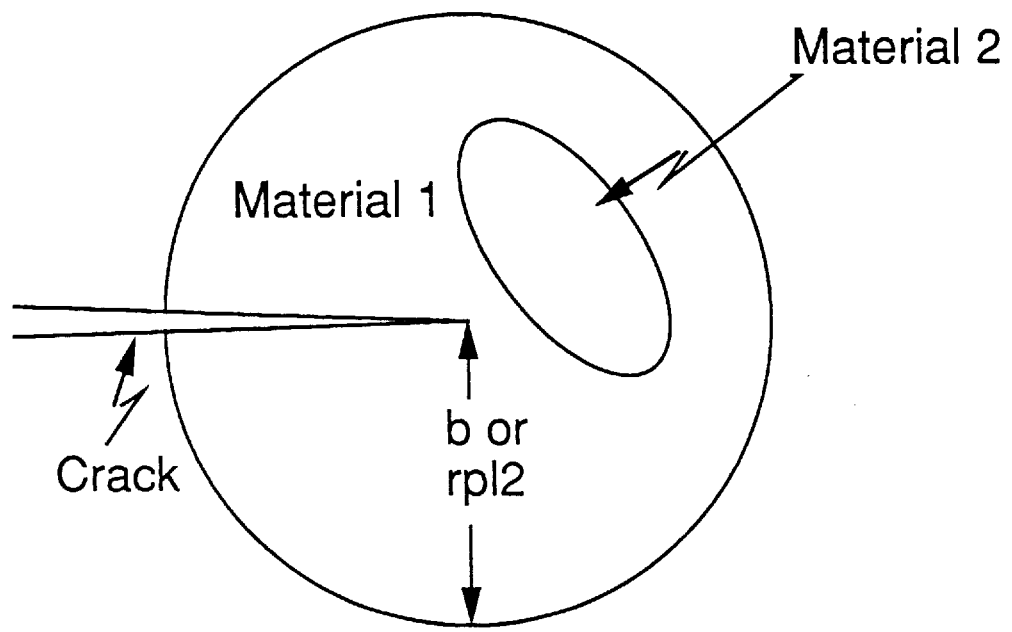
FIG. 17 shows a completely enclosed elliptically shaped entity.
Figure 46:
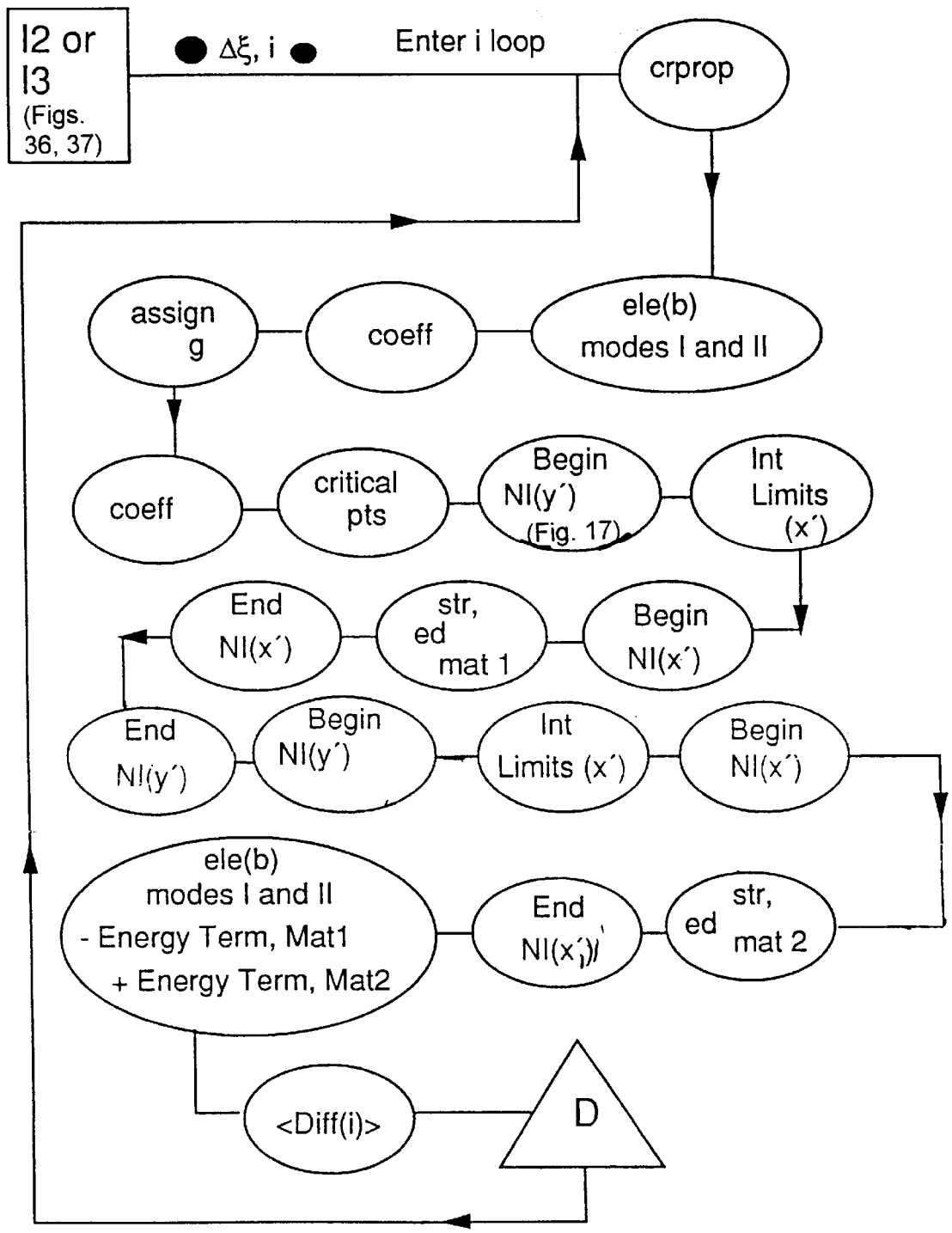
FIGS. 46 and 47 are flow charts for routines when the elliptically shaped entity is completely enclosed.
Figure 47:
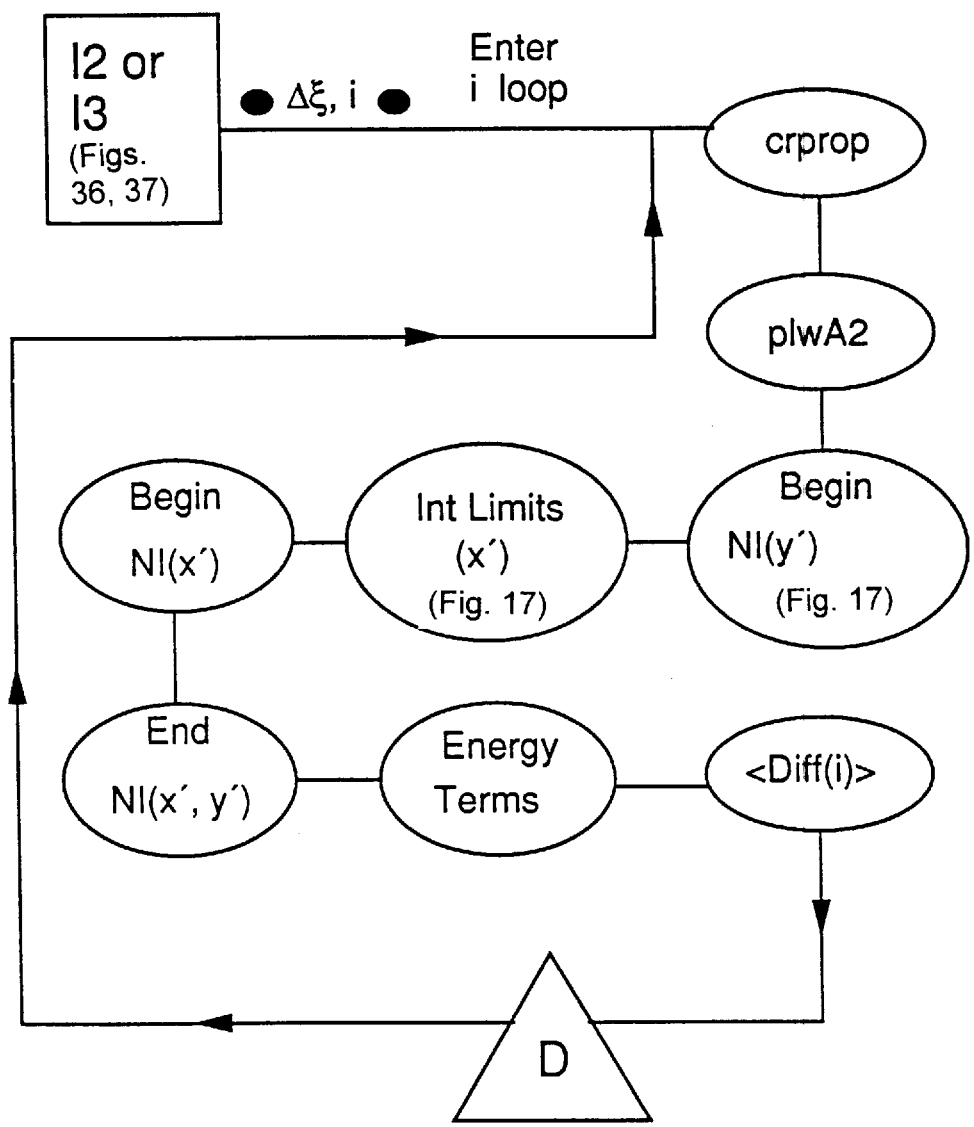

IVB.2 An Elliptically Shaped Entity is Completely Enclosed Within One of the Circular Regions of Radius b or rpl2 (FIGS. 17, 46 and 47)

If the elliptically shaped entity is completely enclosed within either the radius b or rpl2 for the entire crack advance, the program checks for overlap and assignment of intersection points discussed later in section IV need not occur. Numerical integration for strain energy or plastic work will occur over the entire entity. The flow of software in this case for the assignment of strain energy is shown in FIG. 46 and for the assignment of plastic work in material 2 in FIG. 47.

Both charts begin with Inquiries 2 and 3 or I2 and I3 to set up geometrical parameters which are shown in more detail in FIGS. 36 and 37 and discussed in section IIB. For both the calculations for strain energy and for plastic work, $\Delta\xi$ and i are calculated, the main loop for crack advance is entered, and crack properties abbreviated crprop are calculated as discussed in section II.

For strain energy in FIG. 46, the next step is to calculate it within the entire circle of radius b for material 1, as abbreviated ele(b) and discussed in more detail in section IVA.2. The next sequence of steps coeff—g—coeff—critical pts are for the coefficients for the equation of the ellipse in the x2, y2 coordinate system and for critical points as discussed in section IVB.1. The sequence is found in many of the programs for elliptically shaped entities and is used to get coefficients and critical points if they are needed later.

Numerical integration for the region within the ellipse in FIG. 17 then begins with Simpson's Rule between values of y' at −k and y' at k in FIG. 5. The local x', y' coordinate system for the ellipse is shown in FIG. 8. The next step, abbreviated Int Limits, is the assignment of limits of integration of x' before integration with respect to x' begins. For the routine here, these limits lie on the left and right hand sides of the ellipse for a given numerical value of y' that has been assigned in the loop for integration with respect to y'. The function to assign these limits uses j, k and y' as inputs, and uses the equation for the ellipse in the x', y' coordinate system to return two values of x' as outputs.

Inside the loop for integration with respect to y', integration then begins with respect to x'. A procedure than changes the x', y' coordinates to r, $\theta$ coordinates using equations discussed in section IVA.1 for elastic stresses and in section IVB.1. Stresses and energy densities for material 1 are calculated in the r, $\theta$ coordinate system as discussed in IVA.1 and numerical integration with respect to both x' and y' ends. The entire numerical integration process is then repeated for material 2.

The results from integration for both materials 1 and 2 are combined with elastic constants used to calculate final strain energy terms[1] for each material. The term for material 1 within the ellipse is then subtracted out of the term found earlier for the entire circular region of radius b. The term for material 2 covering the region within the ellipse is added in to give a final total strain energy corresponding to FIG. 17.

The strain energy for the entire region or differences between each increment of crack advance may be calculated and stored in a data file, as shown at the bottom of FIG. 46. The software then continues to the top of the chart within the main loop for crack advance and repeats the steps discussed in this section for each increment of crack advance.

The process shown in FIG. 47 is very similar to that just described for strain energy. The difference is that the entity lies within the radius rpl2 and plastic work instead of strain energy is used. Accordingly, plastic work per unit area, abbreviated plwA2, is assigned just after crack properties. The result of the numerical integration will be the area inside the ellipse. If the work term desired by a user is a function of r and $\theta$ or of x' and y', the appropriate procedures to change coordinate systems and assign the plastic work per unit area can be added by a user after the step marked Int Limits.

IVB.3 Assignment of flag1 (FIGS. 19, 20, 23 and 48)

Flag1 is the parameter by which the various programs recognize whether one of the circular regions either of radius b or rpl2 partially overlaps an elliptically shaped entity. The significance of the flag is that once a program recognizes that there is overlap and what type, it finds for each crack position the intersection points between the circle and the ellipse, sets everything up for numerical integration in the appropriate region, integrates over the region for the appropriate energy and stores the result in memory for each crack position.

Before discussing the function to assign flag1, it is useful to define a few terms. In this description, the term shortlength 1 will refer to the shortest distance between the crack tip and the ellipse. Suppose a line L extends from the crack tip to the ellipse covering this shortest distance. Shortlength 2 will then refer to the distance covered from the crack tip to the other side of the ellipse when the line L is extended in the same direction through the interior of the ellipse to the other side.

Figure 19:
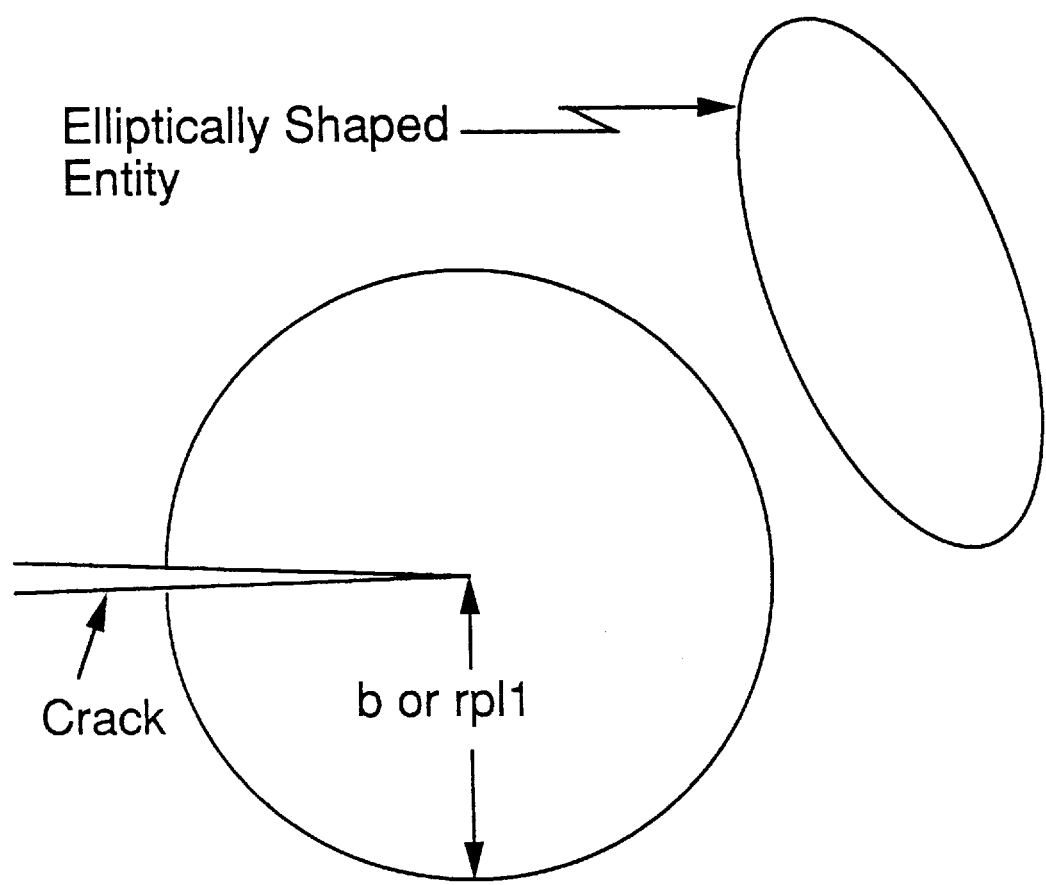
FIG. 19 shows a situation of no overlap between the circular regions and the elliptically shaped entity.
Figure 20:
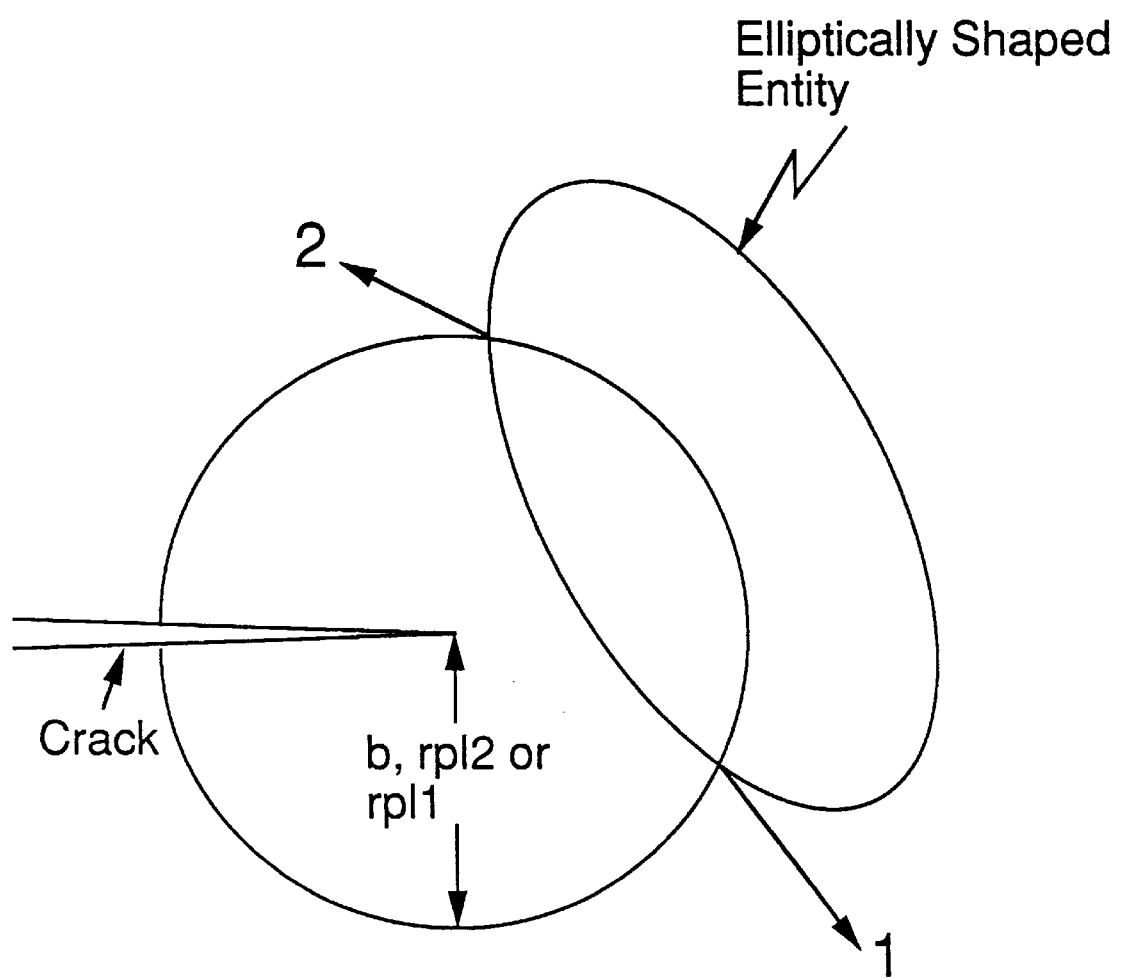
FIG. 20 shows a situation in which the overlap requires one numerical integration.
Figure 23:
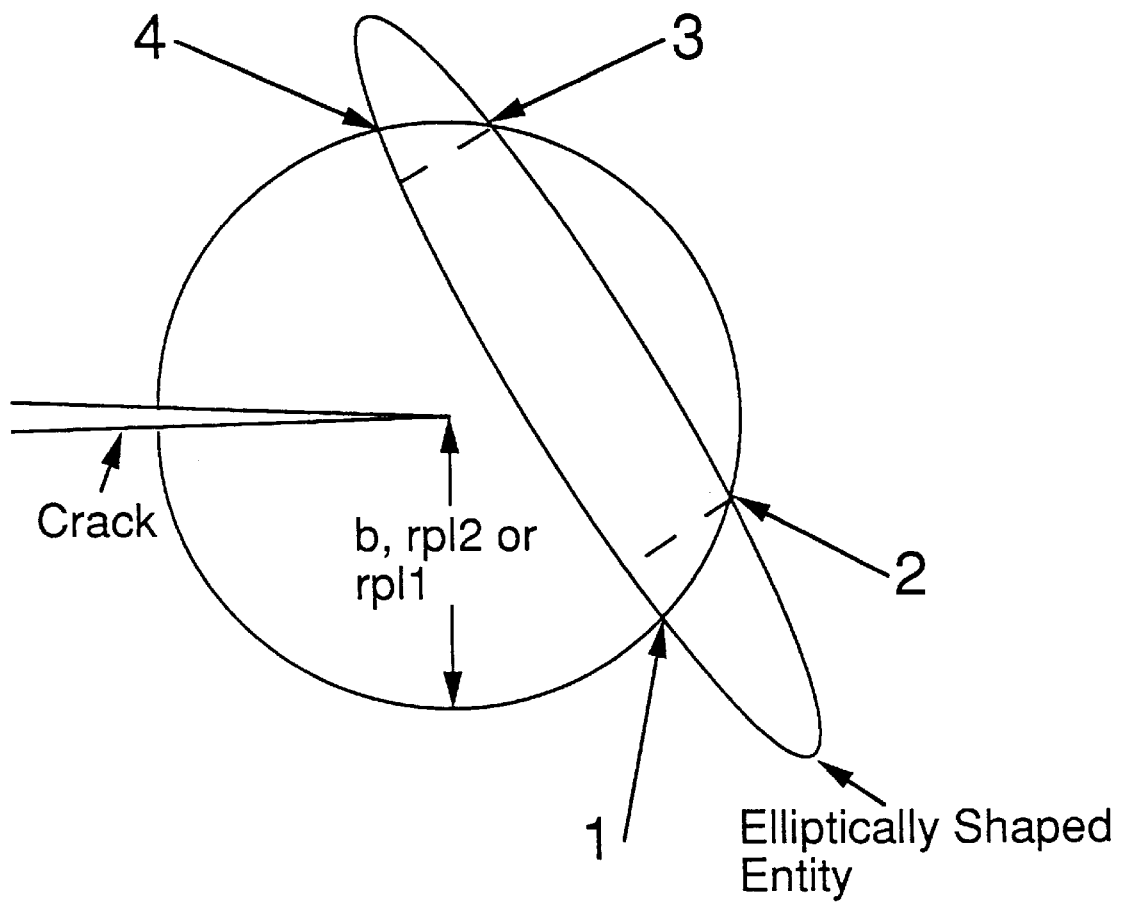
FIG. 23 shows a situation in which a circular region extends over the elliptically shaped entity and back into the matrix.

The function to assign flag1 compares the lengths of shortlength1 and shortlength2 with the radius of the circular region in question. Suppose, for example, that the program is for elastic strain energy and the radius of the circle in question then is b. If b is greater than shortlength 1, as shown in FIG. 20, the circular region will have a simple overlap onto the elliptically shaped entity. If b is less than shortlength 1, the situation will be as illustrated in FIG. 19. No overlap will occur and flag1 is set to 0. If b is greater than shortlength2, as shown in FIG. 23, the circular region will overlap the elliptically shaped entity and extend back into material 1. Flag1 is assigned a number 0, 1 or 2 corresponding to these three situations.

The function that assigns flag1 itself uses shortlength1, shortlength2 and b or rpl2 as inputs. It uses b or rpl2 depending upon whether the energy in question being assigned is strain energy or plastic work. Suppose again, for example, that the region in question has radius b. The function first assigns two temporary variables t1 and t2 to 0. t1 and t2 are similar to the intermediate flags f1 and f2 used to set finalflag in section IVA.1 in that they change their values when one length parameter is less than or greater than another length variable. If b is less than shortlength1, t1 remains at 0. t1 gets reassigned to 1 if there is overlap and b is greater than shortlengthl. t2 remains at 0 unless b is greater than shortlength2, denoting an overlap that extends back into material 1, as shown in FIG. 23. t1 will also be assigned a value of 1 if b is greater than shortlength2. Flag1 will then be a sum of t1 and t2, resulting in values of flag1 of 0, 1 or 2 corresponding to the situations in FIGS. 19, 20 and 23, respectively.

The function to get the shortest distance itself between the crack tip and ellipse uses the coordinates of an initial point and the coefficients c1 to c6 of the equation for the ellipse discussed in section IVB.1 as inputs. It uses a Newton-Raphson routine[3] to find two common roots x2, y2 of two equations. One equation is for the ellipse in the x2, y2 coordinate system discussed in section IVB.1. The other is the equation for the line that contains the segment whose length is the shortest distance between the crack tip and ellipse. The line passes through the origin 0, 0 of the x2, y2 coordinate system and, because it will be perpendicular to the ellipse, has a slope that is the negative of the reciprocal of the slope of the ellipse. The two roots found by the Newton-Raphson routine are the abscissa and ordinate in the x2, y2 coordinate system of the intersection of the line and ellipse. The shortest distance is then the distance from the origin to this point found through a right triangle.

The procedure to assign shortlength2 is based upon a general function used often in the programs for elliptically shaped entities that assigns a distance r in the r, θ coordinate system for points lying on the circumference of the ellipse. The parametric equations x2=rcosθ and y2=rsinθ can be substituted into the equation for the ellipse in the x2, y2 coordinate system discussed in section IVB.1 to yield an equation along the circumference of the ellipse of the form $h_1 r^2 + h_2 r + h_3 = 0$. For a known value of θ, r becomes the only independent variable in the equation with $h_1$, $h_2$ and $h_3$ being coefficients dependent upon θ and the variables c1 to c6 discussed in section IVB.1. For a given value of θ, the equation can be solved for two values of r, one on the left hand side of the ellipse and one on the right hand side of the ellipse when the line for r is extended through the interior of the ellipse.

Returning to the assignment of shortlength2, the Newton-Raphson routine discussed previously in this section returns coordinates x2, y2 on the ellipse at which the distance between the crack tip and the ellipse is a minimum. The position of θ for this point in the r, θ system is found from an angle having y2/x2 at this point as a tangent. Since the value of θ is known, the distance r to the right hand side of the ellipse is found by the method discussed in the last paragraph. The function for shortlength2 therefore uses this particular value of θ and the coefficients c1 to c6 of the equation for the ellipse in section IVB.1 as inputs and returns shortlength2 as an output.

The functions that set coordinates to begin the Newton-Raphson routine to find the shortest distance to the ellipse use a simple trigonometric approximation to get a point close to that calculated by the Newton-Raphson routine. The angle θ is set to φ and a right triangle is formed between ξ and a vector in the r direction at the angle θ of φ. The length of the vector r is ξcosφ and its projection onto the x2 axis is ξcos²φ. The component of r in the y2 direction is ξcosφsinφ. These components, the coordinates of the point of the end of the vector r in the x2, y2 coordinate system, are used as coordinates of a point to begin the Newton-Raphson routine. The functions for the x2, y2 coordinates therefore uses ξ and φ as inputs and returns the two components along the x2 and y2 axes as outputs for an initial point to begin the routines.

Figure 48:
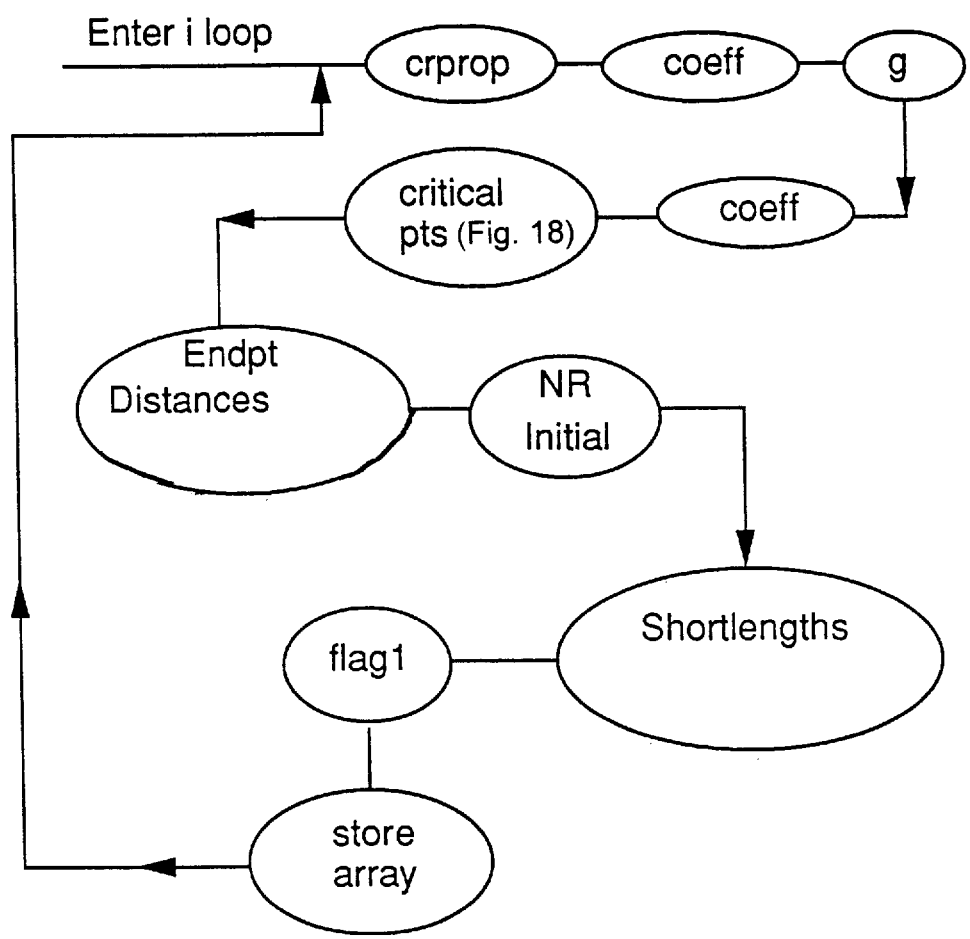
FIGS. 48–52, 53A, 53B and 54–56 are flow charts for flags for overlap, intersection points and number of integrations.

FIG. 48 shows the sequence used to set flag1. A loop with a maximum counting integer i is entered and the crack tip is incremented through all the positions to be used later to calculate energy. The first sequence crprop—coeff—g—coeff—critical pts—End pt Distances is a collection of procedures to get basic parameters commonly used in all the programs for elliptically shaped entities. crprop is discussed in section IIC and coeff—g—coeff—critical pts is discussed in section IVB.1. Endpt distances are a collection of procedures getting the distances to the ends of the ellipse. The distances are used primarily in finding and assigning intersection points and are discussed in more detail in section IVB.5.

Proceeding down the chart, one comes to NR initial, which is an abbreviation for assigning an initial starting point(s) for a Newton-Raphson routine discussed earlier in this section. The next step shortlengths refers to the assignment of shortlength1 and shortlength2. flag1 is then assigned using the function described at the beginning of this section.

Each flag1 for each crack position is then stored an array variable of dimension i. The label "store array" in FIG. 48 indicates this procedure. When the i loop is opened again for crack advancement and energy calculations, the corresponding component of the array variable is read for flag1 for each crack position before regions for numerical integration are determined. ps IVB.4 Overview of Assignment of Elastic Strain Energy and Plastic Work in Elliptically Shaped Entities (FIGS. 19–23 and 57–64)

Figure 57:
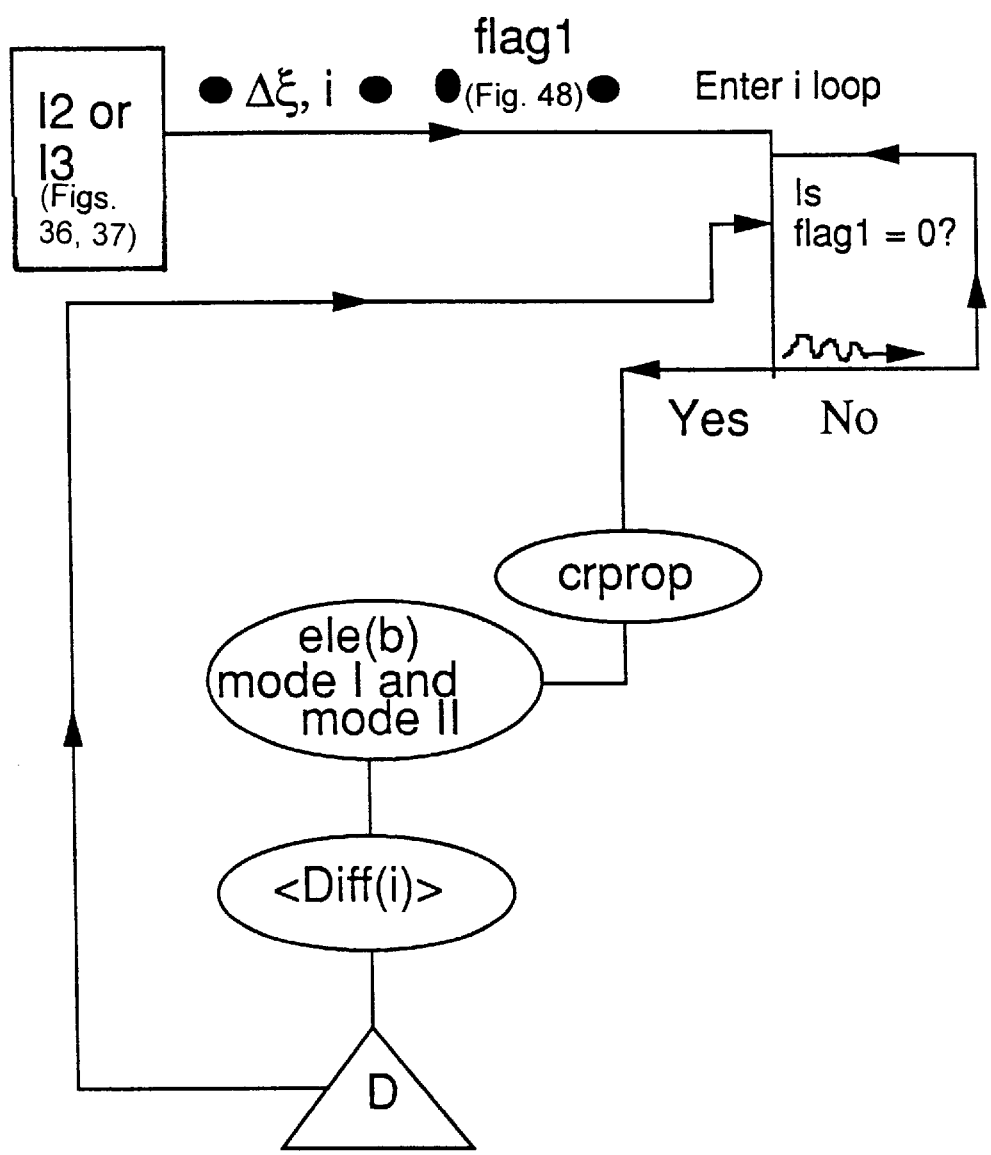
FIGS. 57–59 are flow charts for routines involving elastic energy.
Figure 58:
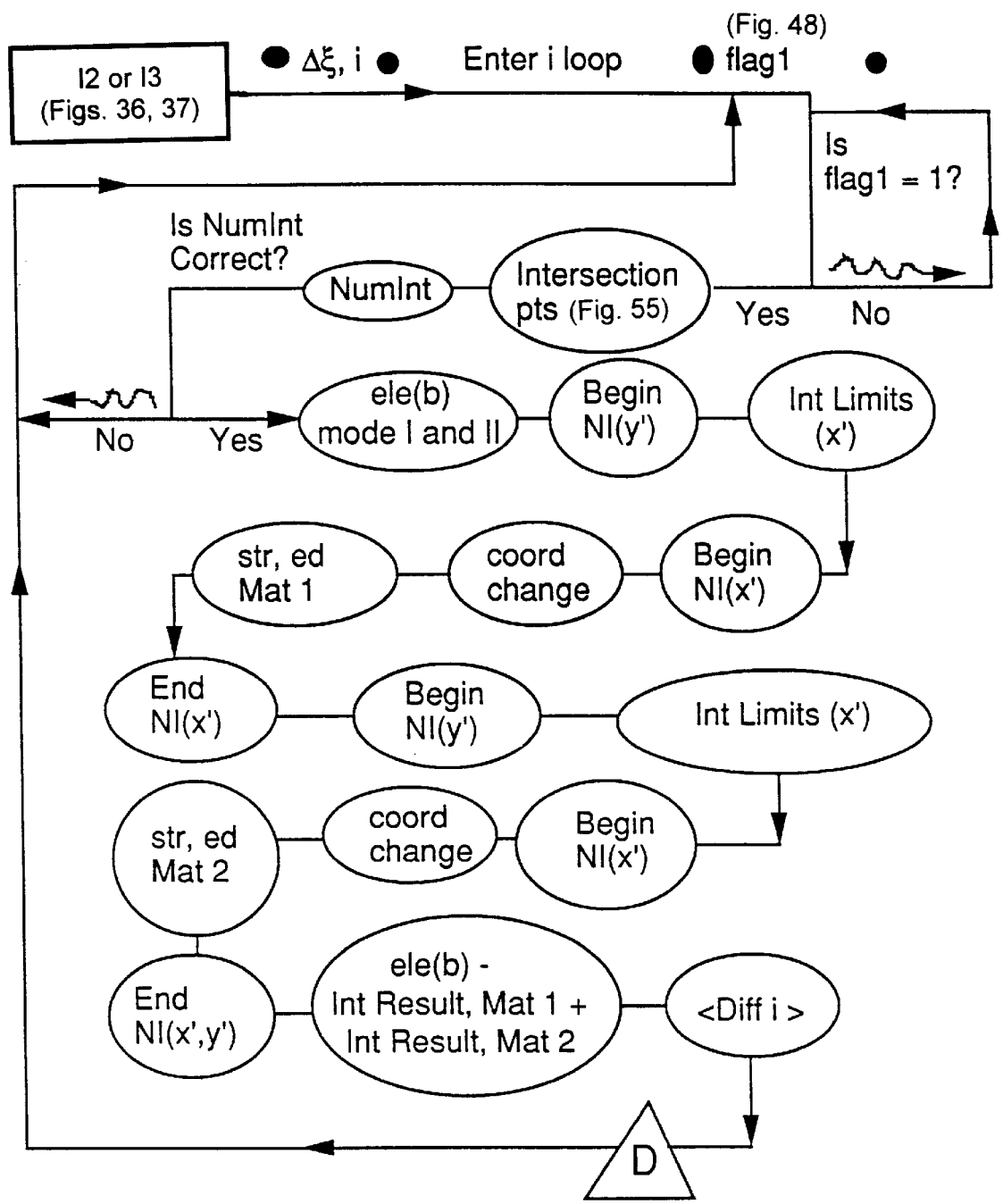
Figure 59:
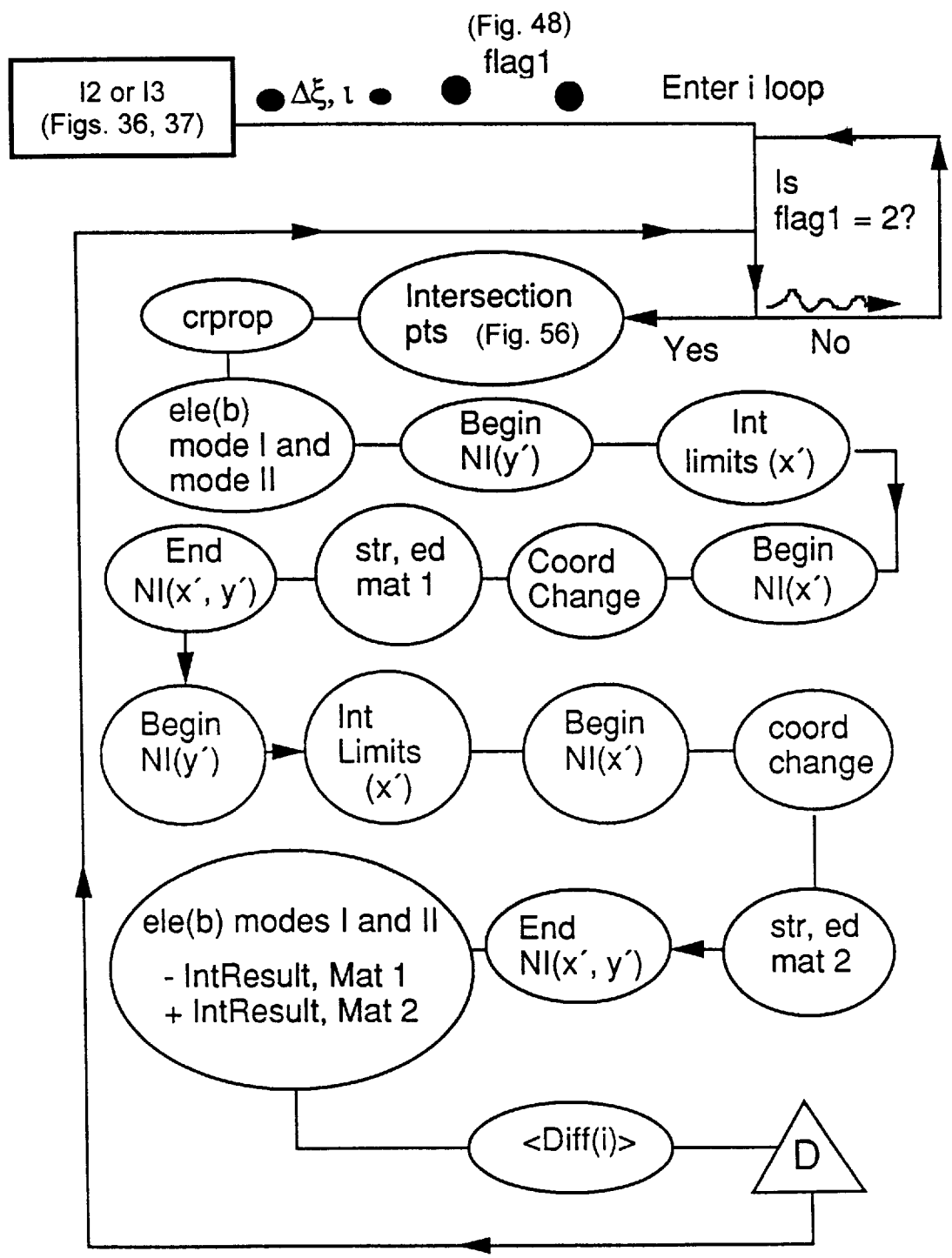
Figure 60:
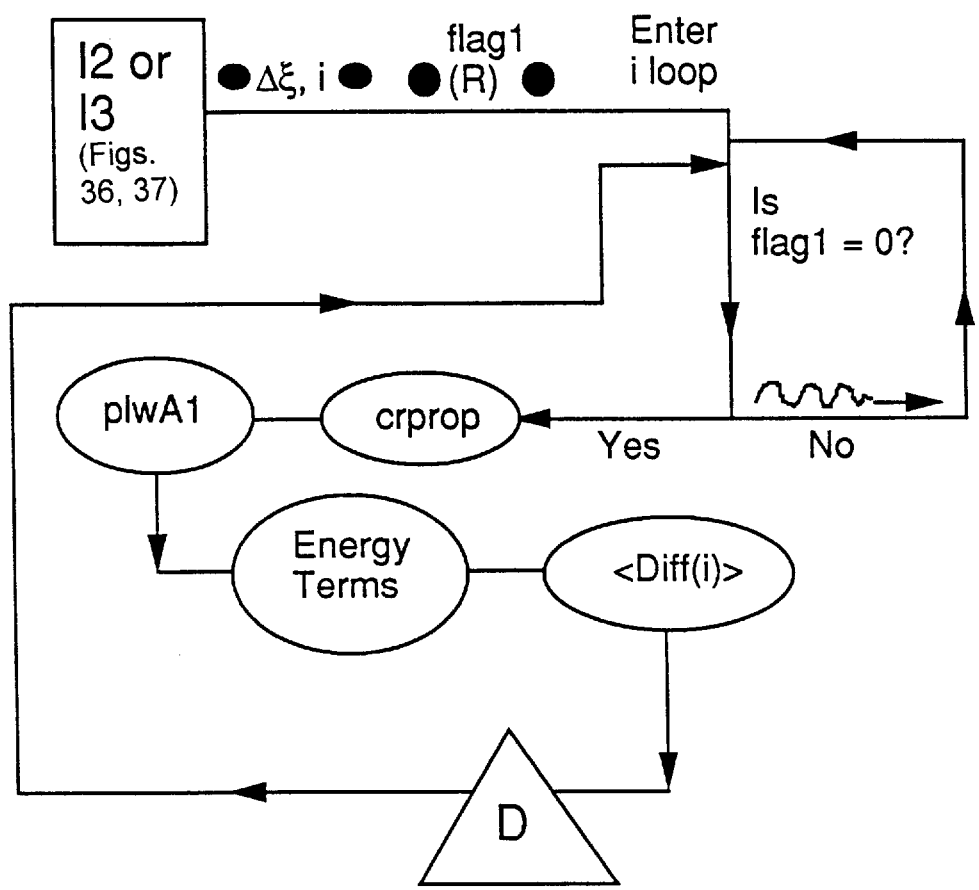
FIGS. 60–62 are flow charts for routines involving plastic work in material 1.
Figure 61:
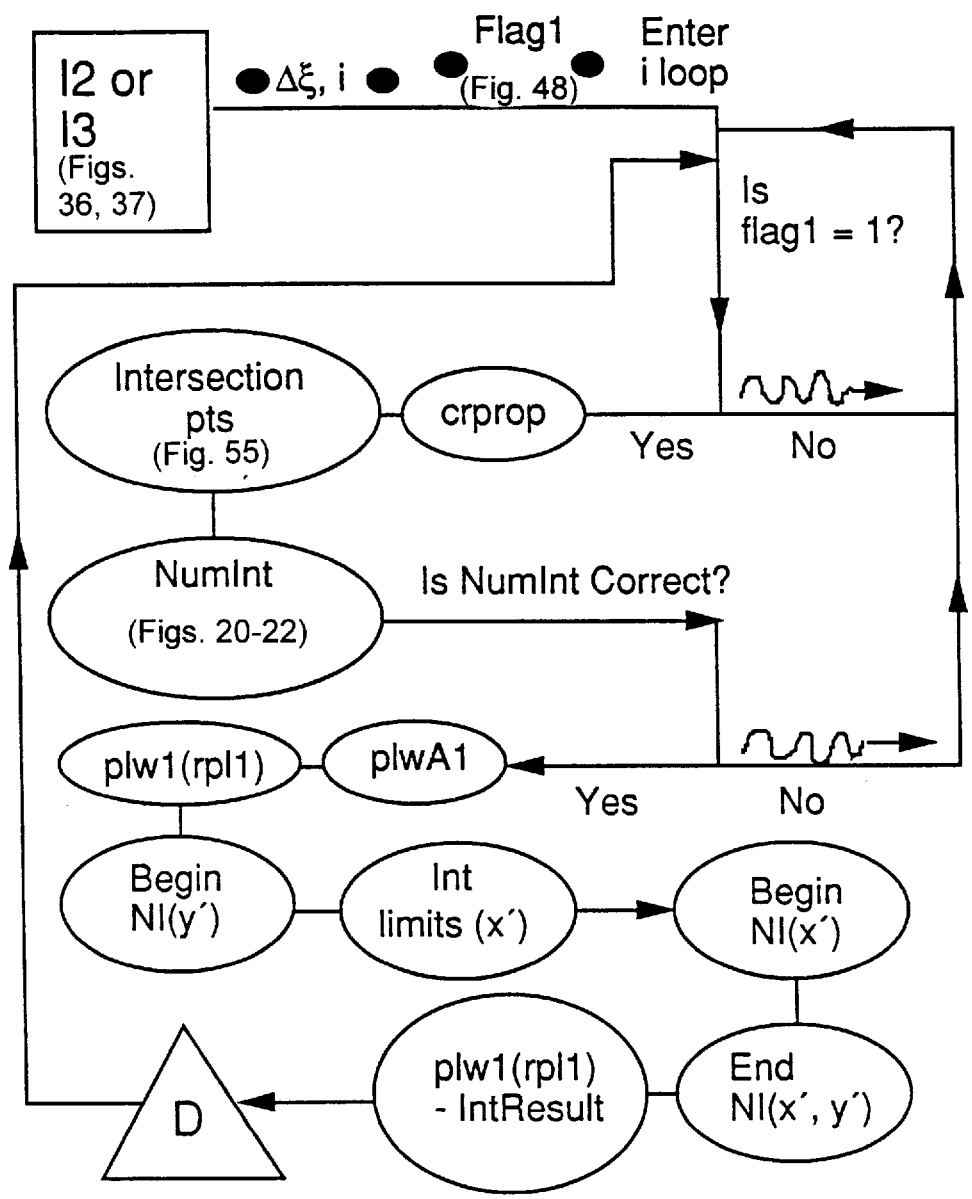
Figure 62:
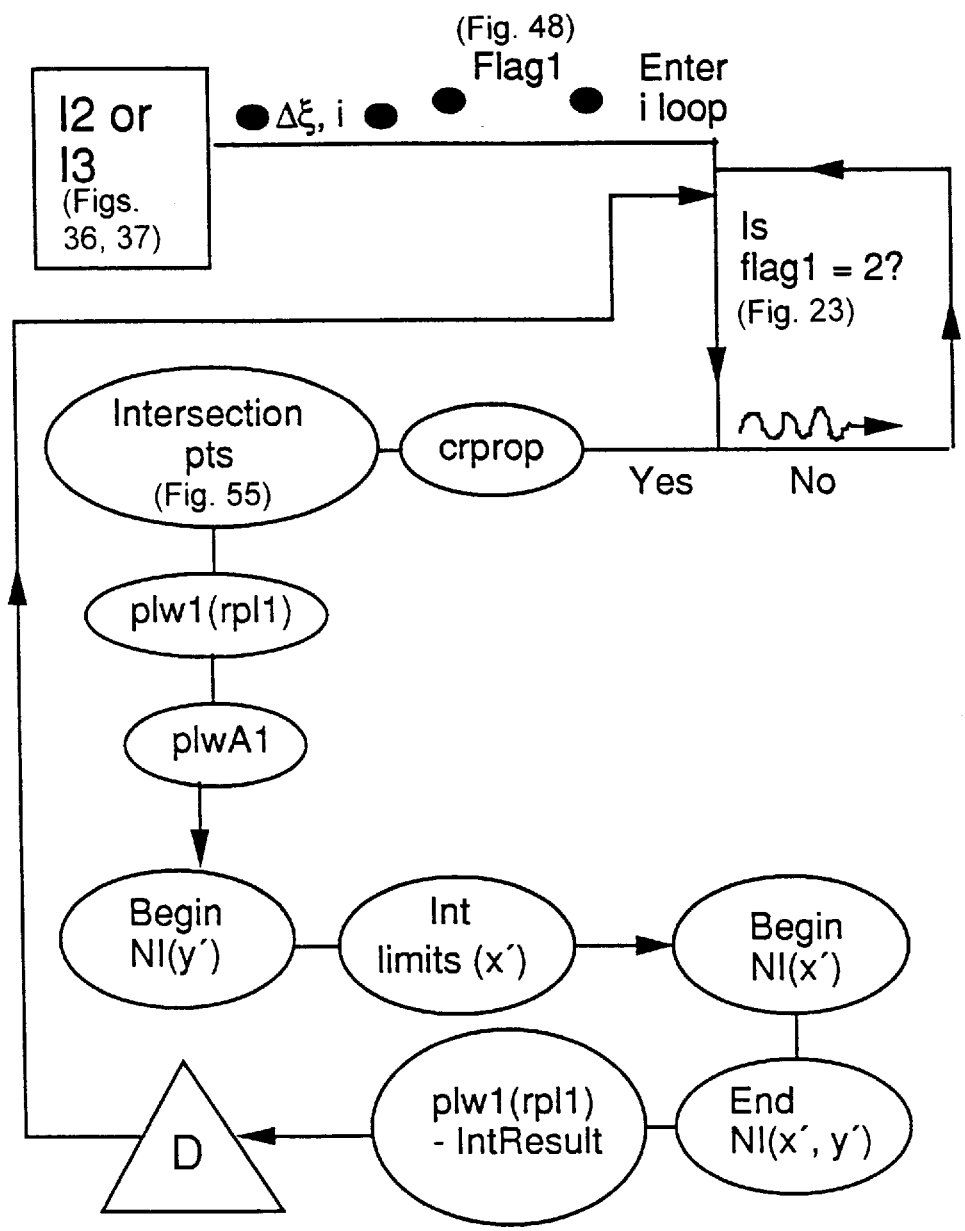
Figure 63:
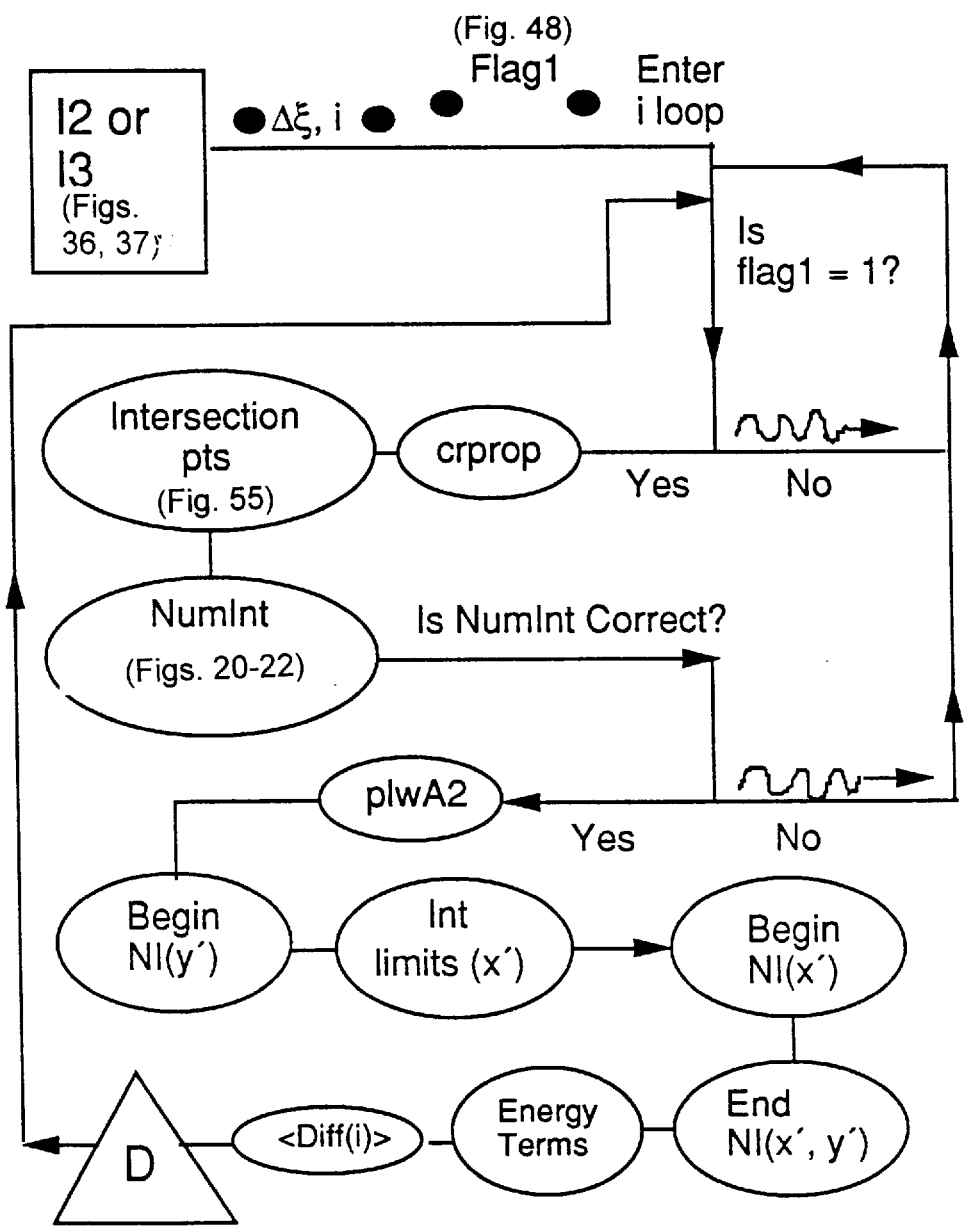
FIGS. 63 and 64 are flow charts for routines involving plastic work in material 2.
Figure 64:
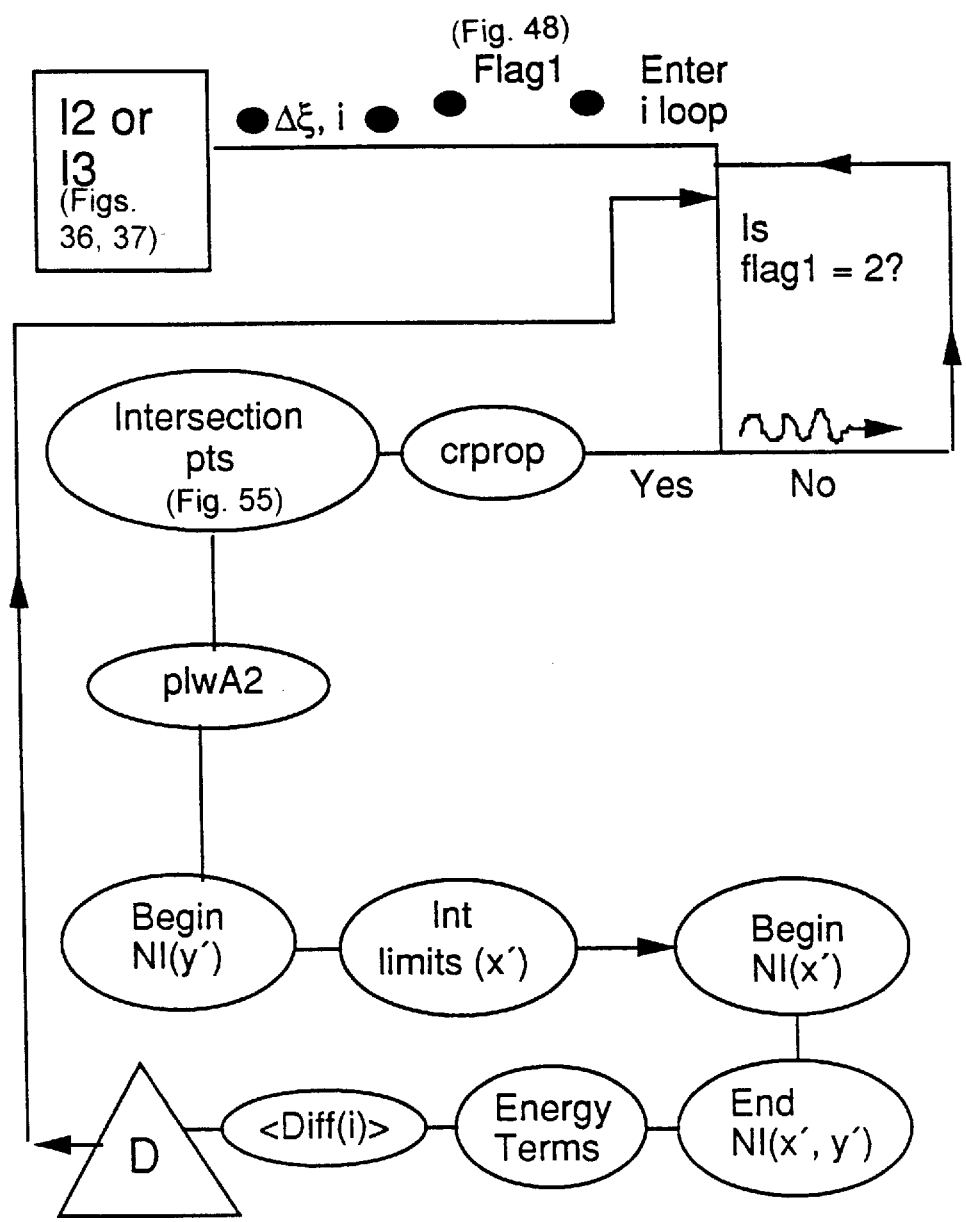

FIGS. 57–64 show the flow of software for the assignment of elastic strain energy and plastic work for setups with elliptically shaped entities. FIGS. 57–59 are for strain energy, FIGS. 60–62 are for plasticity around the crack tip in material 1, and FIGS. 63 and 64 are for plastic work in material 2.

FIGS. 57 and 60 are for when flag1 is 0 and the situation in FIG. 19 with no overlap occurs. FIGS. 58, 61 and 63 are for when a simple overlap occurs as in FIG. 20 and flag1 is 1. FIGS. 59, 62 and 64 show the flow of software when the overlap extends over the elliptically shaped entity and back into material 1 as shown in FIG. 23 and denoted by flag1 being 2.

Most of the processes have been discussed in previous sections, and what follows is an outline of some new and salient features in these processes. Assignment of strain energy, for example, is discussed in detail in section IVA.2. Plasticity in both material 1 and 2 is in section IVA.3. General procedures for numerical integration within an ellipse are discussed for a completely enclosed entity in section IVB.2.

At the top of the charts after the i loop has been entered a check point for the correct types of overlap through flag1 is passed. If the conditions are correct, assignment of an energy term will proceed and storage of a result in memory for that crack position will occur. Otherwise, the software goes back to the beginning of the main loop and flag1 is checked again for the next crack position.

In FIGS. 58, 61 and 64, for simple overlap, another check point called "NumInt" is passed. This is an abbreviation for the number of regions with differing limits for x' over which numerical integration must be completed to cover the entire region of overlap. In FIG. 20, for example, numerical integration mustcover only between points 1 and 2 to cover the entire region of overlap. Once integration with respect to y' has begun, the limits for integration with respect to x' remain on the left at the left hand side of the ellipse and on the right on the circle. Only one integration with respect to x' and y' is needed to cover the region of overlap and NumInt is 1.

Figure 21:
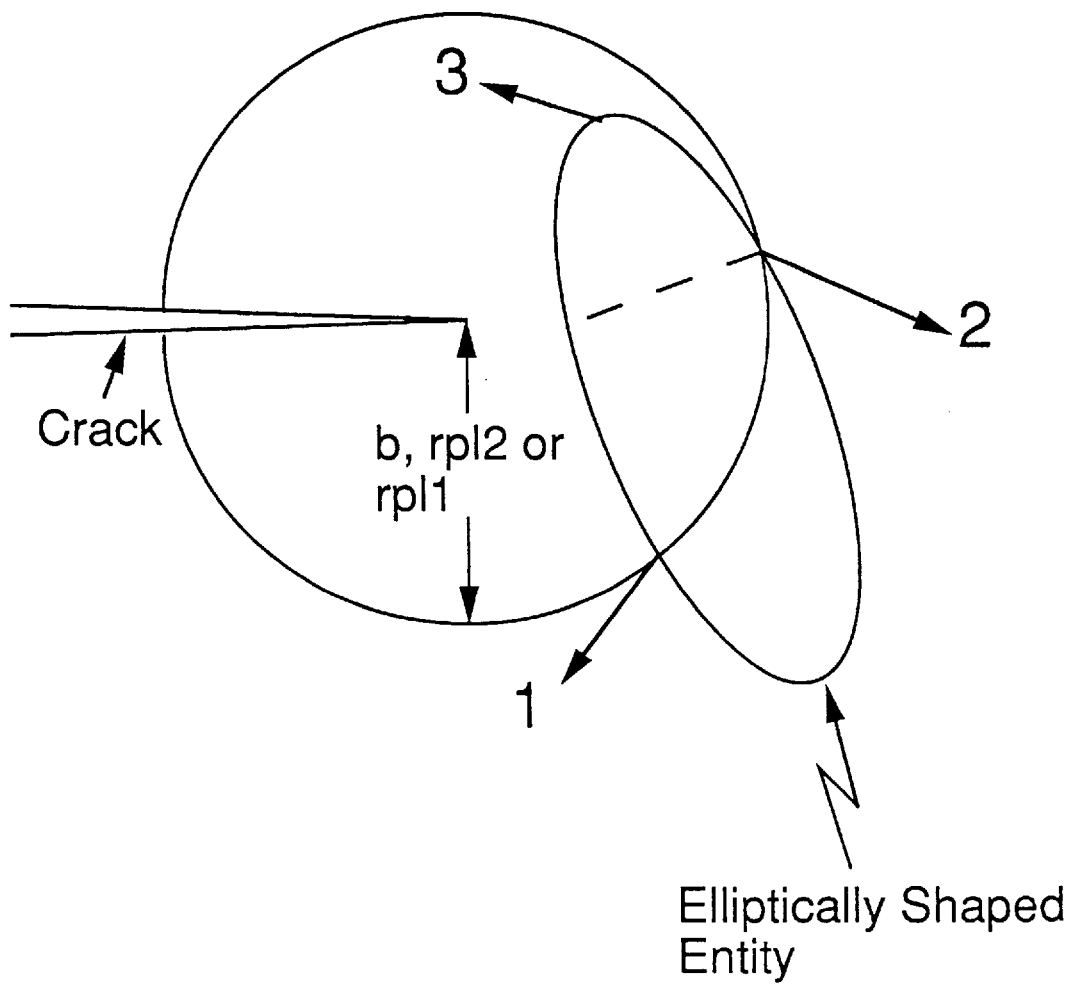
FIG. 21 shows a situation in which the overlap requires two numerical integrations.

In FIG. 21, integration with respect to y' must occur between points 1 and 3 to cover the entire region of overlap. At point 2, however, the limit for x' changes on the right hand side of the overlap. Between points 1 and 2, integration with respect to x' occurs between the left hand side of the ellipse and the circle. Between points 2 and 3, integration occurs between the left and right hand sides of the ellipse. There are two sets of integration limits for x' and NumInt is set at 2.

Figure 22:
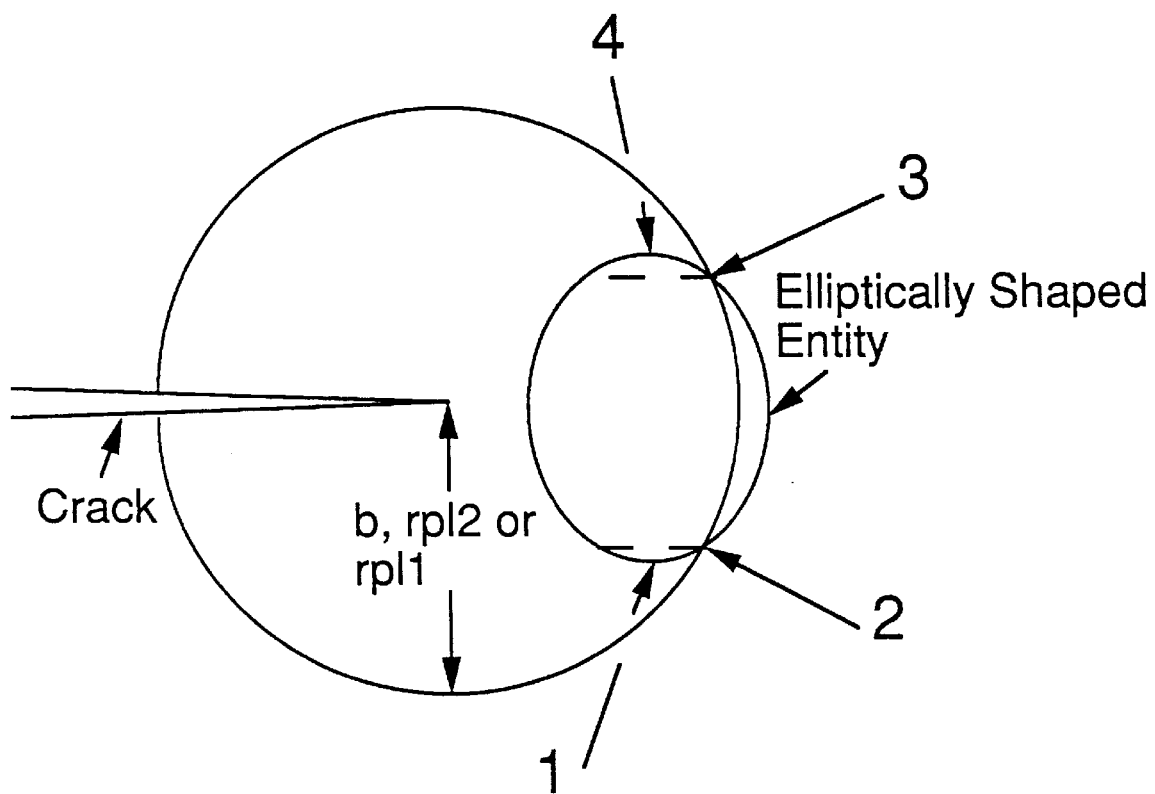
FIG. 22 shows a situation in which the overlap requires three numerical Integrations.

In FIG. 22, integration with respect to y' must occur between points 1 and 4 to cover the entire region of overlap. Between points 1 and 2, the limits for integration are at the left and right hand sides of the ellipse. Between points 2 and 3, integration with respect to x' must occur between the left hand side of the ellipse and the circle of radius b, rpl2 or rpl1 on the right. Between points 3 and 4, the limits for x' are between the left and right hand sides of the ellipse again. There are three sets of integration limits for x' and NumInt is 3.

In the system herein described, separate programs will numerically integrate over each separate region having a distinct set of integration limits for x'. In FIG. 22, for example, one program will integrate between points 1 and 2, another between points 2 and 3 and a third program between points 3 and 4. If an another type of overlap occurs for a particular crack position, NumInt will not be correct for that program and the crack is incremented to the next position without calculation and storage of an energy result in memory.

Once a user has run all the programs in a particular series, every possible type of overlap will have been checked for that particular energy quantity. After all the programs in a 60 series have been run, for example, the energy quantities will have been numerically integrated and stored in the correct positions in memory, even if no overlap as in FIG. 19 or an overlap extending back into material 1 has occurred as in FIG. 22.

Once a user has run all the programs for a particular entity, as discussed in section IID, all the energy quantities will appropriately calculated and stored on memory. The user need not keep track of which kind of partial overlap is occurring.

Under the term Int Limits x', one of the limits for x' as just discussed can be along one of the circles of radius b, rpl2 or rpl1. The function that assigns x' along the circle for a known numerical value of y' during the loop for numerical integration with respect to y' uses $\phi$, g, c, y' and the radius of the circular region at hand as inputs. The equation for the circle in the x2, y2 coordinate system is $x2^2+y2^2=radius^2$. This equation is combined with the equations to transfer between the x2, y2 and x', y' coordinate systems discussed in section IVB.1 to give x' on the circle as an output.

The term "coord change" within the numerical integration routines refers to procedures to move from the x', y' coordinate system in which actual numerical values for x' and y' are at hand to the r, $\theta$ coordinate system in which expressions for elastic stresses are written. These stresses in the r, $\theta$ coordinate system are discussed in more detail in section IVA.2 and equations for coordinate changes are in section IVB.1.

The term "Intersection Points" just after a correct flag1 has been passed at the word "Yes" refers to the process of finding the intersection points labeled 1, 2, 3 and 4 in FIGS. 20 to 23. The procedures are in more detail in FIGS. 55 and 56 and discussed in section IVB.5. The processes of recognizing where these intersection points are and how many integrations to do between which limits are in more detail in FIGS. 49–54 and discussed in section IVB.6.

IVB.5 Overview of Finding the Intersection Points between the Ellipse and One of the Circles (FIGS. 18, 20–23 and 55–56)

Figure 55:
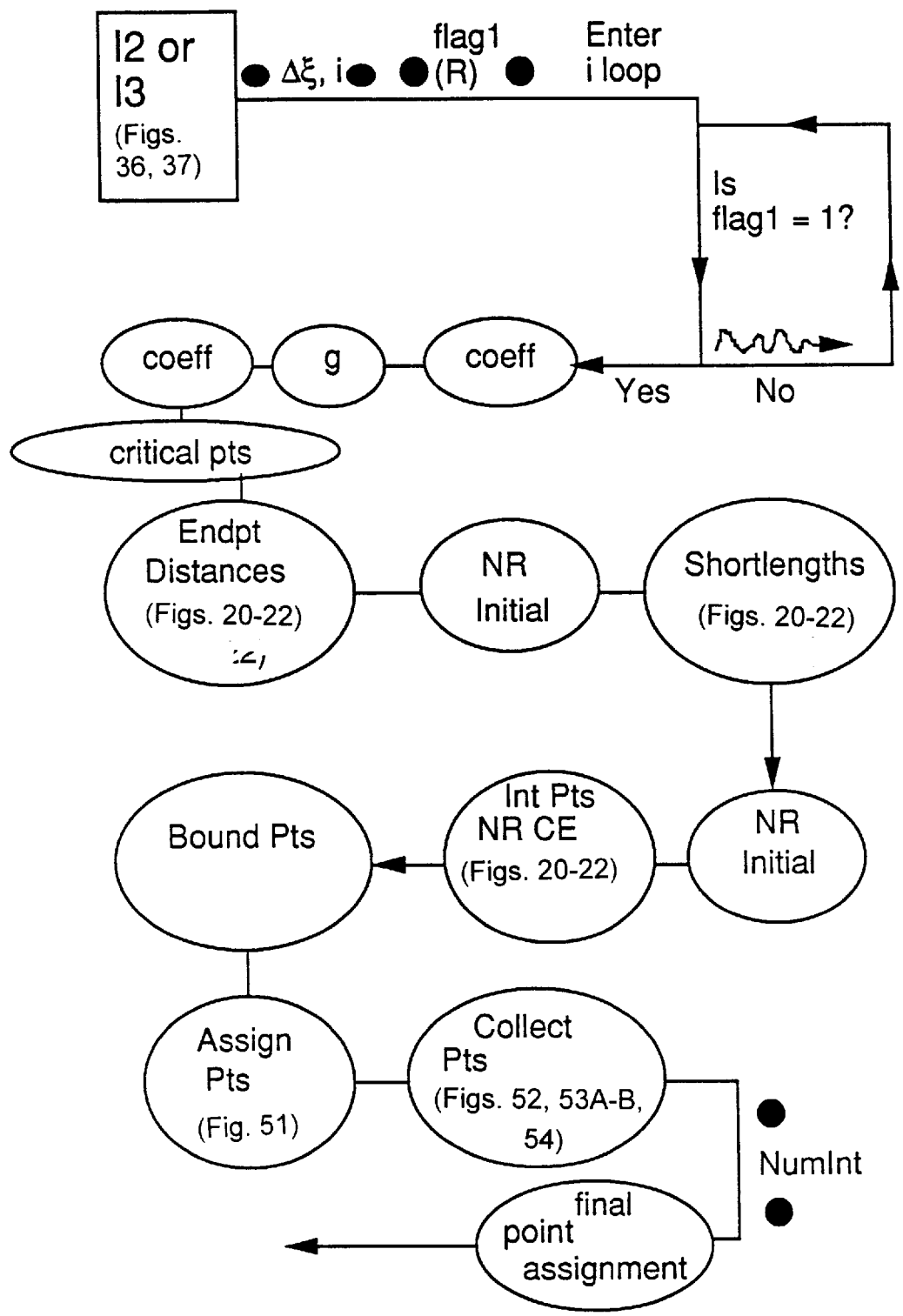
Figure 56:
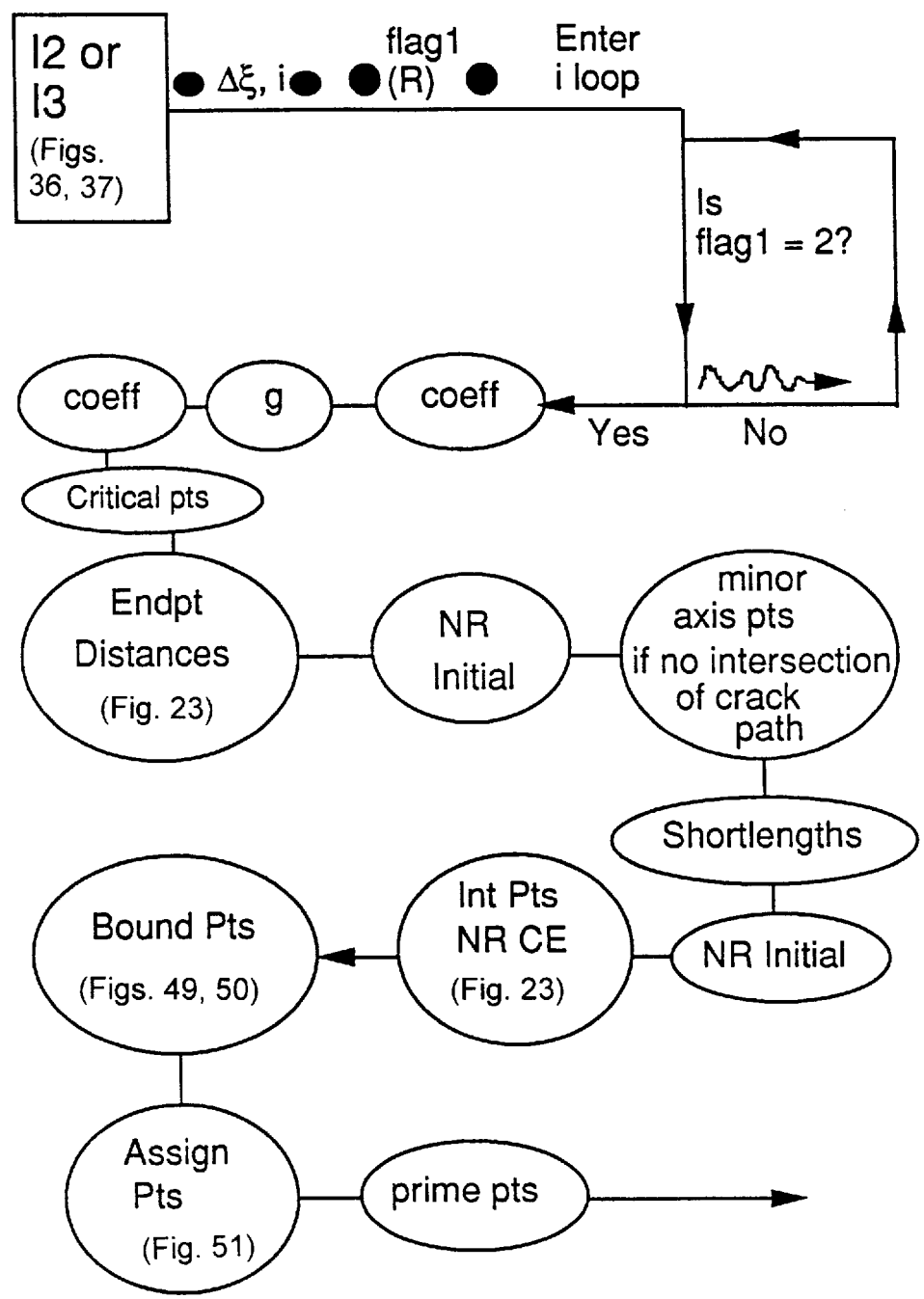

FIGS. 55 and 56 show the process of assigning intersection points between the elliptically shaped entity and one of the circles in more detail. The intersection points are the points 1 to 4 found in FIGS. 20, 21, 22 and 23. They are found and set up as limits for y' in numerical integration.

Both FIGS. 55 and 56 show very similar processes, with the basic difference being that FIG. 55 is for the cases shown in FIGS. 20 to 22 and FIG. 56 is for the situation in FIG. 23. In FIGS. 20 to 22 there are only two intersection points, but the different configurations in FIGS. 20 to 22 are distinguished and it is determined how many sets of limits for x' will be needed to cover the region of overlap. The term "Collect pts" near the bottom of FIG. 55 refers to these processes of finding the number of sets of limits for x'. Afterwards the term NumInt refers to the number of separate integrations involving different sets of limits for x' to cover the region of overlap as discussed in section IVB.4. The term "final point assignment" refers to the final assignment of ordinates of the intersection points in the x', y' system in which it is then known which ordinate of which intersection point is higher and which configuration in FIGS. 20 to 22 is relevant.

FIG. 56, in contrast, is for the situation in FIG. 23 in which there are four distinct intersection points. Between points 1 and 2, x' is integrated between the left hand side of the ellipse and the circle. Between points 2 and 3, x' is integrated between the left and right hand sides of the ellipse. Between points 3 and 4, the limits are between the left hand side of the ellipse and the circle. The number of sets of integration limits for x' is set at three.

Accordingly, the processes Collect Pts and NumInt are skipped at the bottom of FIG. 56. The final step "prime pts" simply refers to setting the ordinates of points 1, 2, 3 and 4 in the x', y' coordinate system so that they are ready for numerical integration.

Returning to the top of the Charts, after flag 1 is passed and the sequence coeff—g—coeff discussed in section IVB.1 is passed, the next four steps are identifying points and calculating distances to divide the circumference of the ellipse into identifiable and quantifiable regions, as shown in FIG. 18. These regions are labeled 1a, 1b, 2, 3, 4a and 4b as shown in the figure. When the crack approaches the entity at a right angle or when the ellipse degenerates into a circle, regions 2 and 3 disappear and there are simply four regions corresponding to what is 1a, 1b, 4a and 4b on the ellipse in FIG. 18.

The first step "critical pts" is discussed in section IVB.1. The coordinates of these points are calculated and stored especially for any Newton-Raphson routine in one variable, such as that used for shortlength1 that could have difficulties where the slope on the ellipse in the x2, y2 coordinate system can be zero or infinity.

The step Endpoint Distances is assigning distances and coordinates to the ends of the ellipse and to the points on the circumference where y2 is 0. These distances and coordinates become important later in identifying where intersection points are and in determining the number of regions of integration.

The calculation of shortlength1 and shortlength2 with the coordinates of their points in intersection, labeled points A1 and A2 in FIG. 18, are repeated in the next step from the time they were first calculated to assign flag1. Their assignment along with the NR initial that is an abbreviation for the initial points to begin a Newton-Raphson routine are discussed in more detail later in this section. The coordinates are used because one intersection point will lie above these points and one below. This particular dividing point on the circumference of the ellipse becomes especially important when there is a small amount of overlap between the interiors of the ellipse and one of the circles.

"Int Pts NR CE" is an abbreviation for assigning intersection points between the circle and the ellipse using a Newton-Raphson routine on two nonlinear equations[3]. This step actually calculates or gets the raw data on the intersection points. The procedure uses some initial points and the coefficients of the equation of the ellipse in the x2, y2 coordinate system as inputs and works with the equation for the ellipse and the equation for one of the circles in the x2, y2 coordinate system. The equation for the ellipse in the x2, y2 coordinate system along with its coefficients was discussed in section IVB.1 and the equation for the circle in section IVB.4. The step NR initial beforehand is the assignment of initial points to begin the Newton-Raphson routines in the regions of the circumference of the ellipse. The points are near the midpoints of regions 1$a$, 1$b$, 2, 3, 4$a$ and 4$b$ and are discussed in more detail later in this section.

"Bound Pts" is a collection of procedures that bounds the raw data coming from the Newton-Raphson Method. The method is used in each of the region 1$a$, 1$b$, 2, 3, 4$a$ and 4$b$ on the ellipse to ensure that all intersection points are found, even if there are four of them as in FIG. 23. The Newton-Raphson method can often be so strong that an intersection point is found twice from two sets of initial points, particularly if the ellipse is small or one of the points is near the boundary of two regions on the circumference. Bound Pts finds out where the calculated intersection points actually are. The procedures are discussed in more detail in section IVB.6 and in FIGS. 49 and 50.

"Assign Pts" is an abbreviation for assigning an actual intersection point 1 on the lower half of the ellipse and an intersection point 2 on the upper half of the ellipse. For the situation for flag1=2 or that in FIG. 23, the procedures find and assign each of the distinct points 1, 2, 3 and 4. Assign pts is discussed in more detail in section IVB.6 and in FIG. 51.

"Collect Pts", as mentioned previously, finds where points 1 and 2 are on the ellipse in FIGS. 20 to 22 in terms of the number of separate integration with respect to x' that need to be done. The procedure puts a label on the points so that the number of integrations can be read. "NumInt" then becomes a simple function that returns a number 1, 2 or 3 that was discussed earlier in this section.

The rest of this section discusses some inputs, outputs and procedures of some of the processes just mentioned, including the rectangular regions and their boundaries used to get initial points in the Newton-Raphson routines and used in the process Bound Pts. Bound Pts, Assign Pts and Collect pts are by themselves discussed in detail in section IVB.6.

The functions that assign the abscissas to the critical points c1 to c4 and to points A1 and A2 in FIG. 18 all use the coefficients c1 to c6 discussed in section IVB.1 as inputs.

They also use the equation for the ellipse in the x2, y2 coordinate system in section IVEB.2. The equation is rearranged to that y2 is expressed as a function of x2. The abscissa at points A1 and A2 are solved for by setting y' to zero. The same equation is also differentiated with respect to x2 to yield an equation for dy2/dx2. This equation is set to zero and infinity to solve for the abscissa at the critical points.

Once an abscissa is obtained for a point on the circumference of the ellipse, a function for the ordinate uses the abscissa and the coefficients c1 to c6 in section IVB.1 as inputs and uses the equation for the ellipse in the x2, y2 coordinate system in section IVB.1. If the abscissa is in the x', y' coordinate system, as is the case later when points are in final preparation, a function uses the abscissa, j and k and inputs and the equation for the ellipse in the x', y' coordinate system discussed in section IVB.2. The outputs of these functions are ordinates for points in the relevant coordinate system.

The functions to assign the abscissa at the ends of the ellipse use k, $\phi$ and g as inputs. The abscissa is simply g+(k×sin(±$\phi$)) with positive or negative $\phi$ used for the lower and upper ends respectively. The distances to the ends of the ellipse in the x2, y2 coordinate system are found through a right triangle.

The initial points to begin the Newton-Raphson routines are put at the midpoints in the rectangular regions containing the portion of the circumference of the ellipse in question. Region 1$a$ in FIG. 18, for example, is bounded by a rectangle with a left side that lies at the abscissa of point c2, a right side at the abscissa of point A1, an upper side at the ordinate of point c2 and a lower side at the ordinate of point A2. These abscissas and ordinates at the "left", "right", "upper" and "lower" sides of these rectangles also become the variables "boundleft", "boundright", "bounbupper" and "boundlower" that denote boundaries of the same rectangles within which checks are made in Bound Pts for actual intersection points between the ellipse and a circle.

Depending upon the orientation and position of the ellipse, sometimes the points on the ellipse at y2=0 are used to help bound the intersection points. If the ellipse does not intersect the crack path, some points called "minor axis points" as labeled in the middle of FIG. 56 are used. These are points on the circumference of the ellipse at the ends of the minor axis of length j where y' is zero. The procedure to set the coordinates of the minor axis points uses g, c, j and $\phi$ as inputs. The abscissas are g added to the appropriate component along the x2 axis of positive or negative j. The component is expressed through the cosine of $\phi$. Similarly, the ordinates are c added to the component of positive or negative/along the y2 axis. The component of j along the y2 axis is expressed through the sine of $\phi$.

IVB.6. Details of Setting up Intersection Points for Numerical Integration (FIGS. 20–23 and 49–54)

Figure 49:
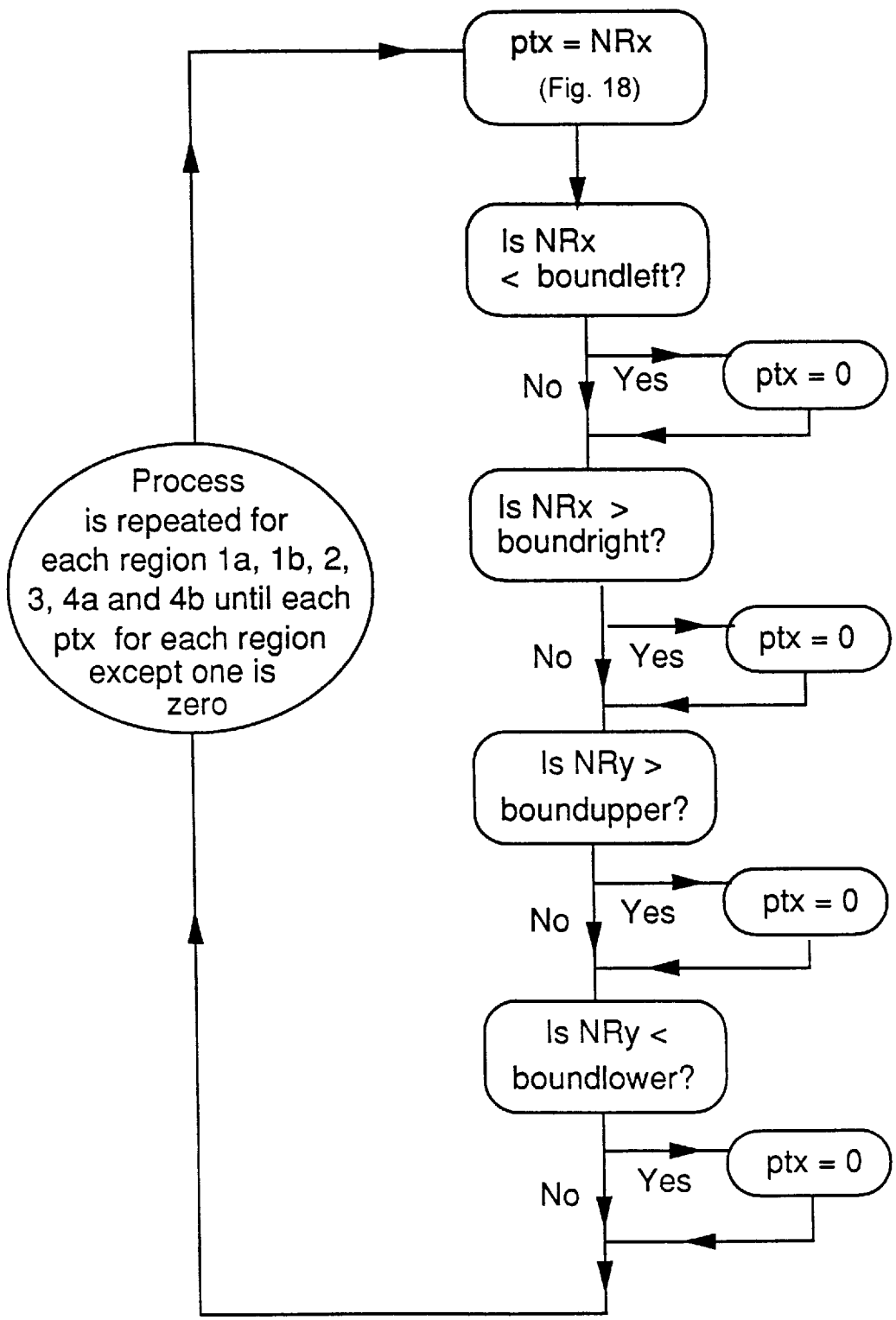
Figure 50:
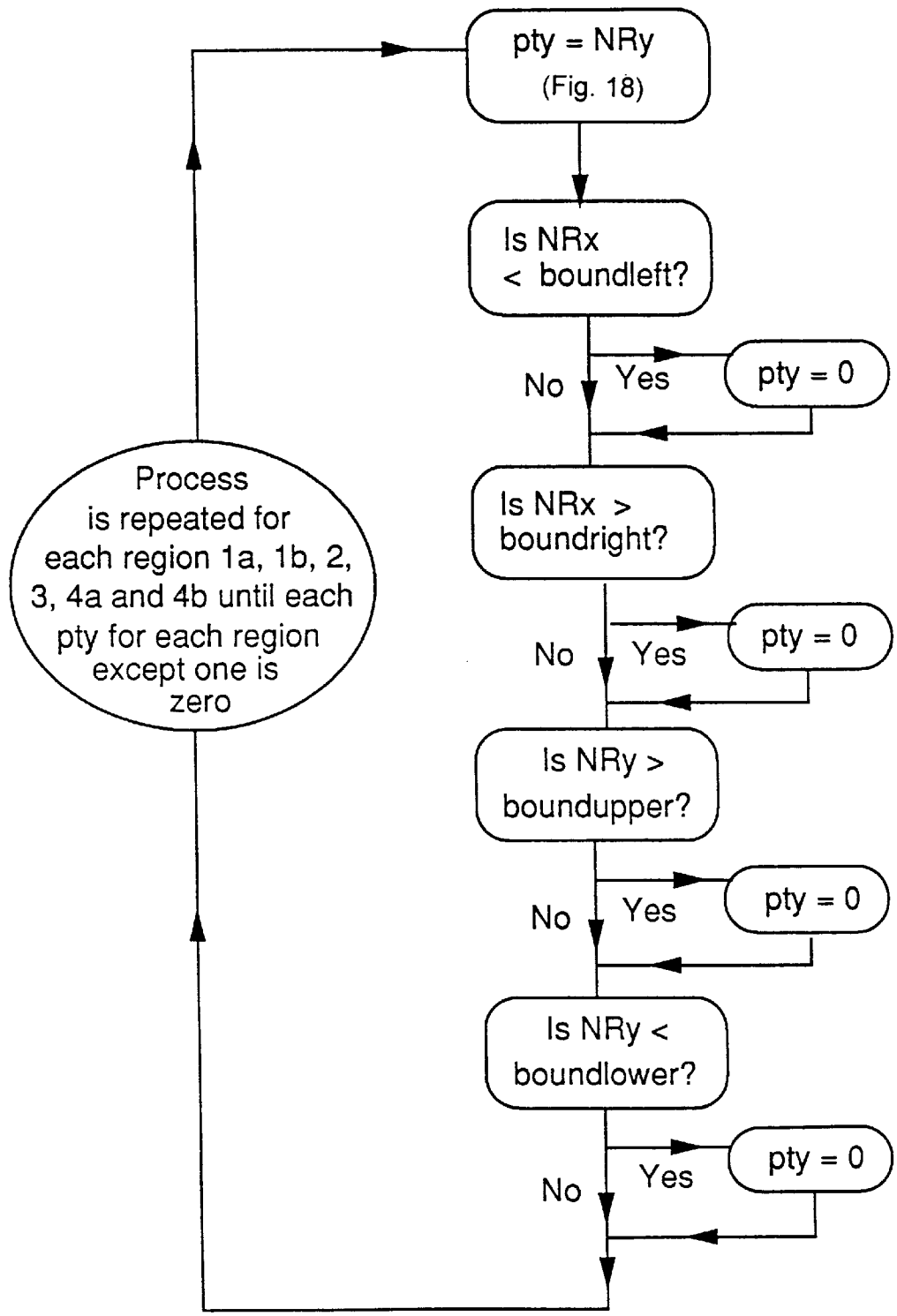

FIGS. 49 and 50 show the details of bounding the intersection points found by the Newton-Raphson routines. The rectangular regions with sides at boundleft and boundright, etc. were discussed toward the end the last section. This section will discuss in detail the flow of the software for the process.

In FIGS. 49 and 50, the terms NRx and NRy are abscissas and ordinates respectively of an intersection point found in the Newton-Raphson method. ptx and pty are test abscissas and ordinates. There is a pair ptx and pty for each region on the circumference of the ellipse. Discussion of these regions can be found in section IVB.1.

At the end of the routines in FIGS. 49 and 50, the point with coordinates ptx, pty in each region will be either 0, 0 or NRx, NRy. A coordinate pair ptx, pty in a region will become NRx, NRy only if the point NRx, NRy from the Newton-Raphson method actually lies within that region. Otherwise ptx, pty will be zero in that region. At the end of the routines, a particular intersection point that might have turned up more than once in the Newton-Raphson routines is now a single point in only one of the regions on the circumference of the ellipse.

At the top of FIGS. 49 and 50, ptx and pty are initially assigned to NRx and NRy respectively. The next four questions are asking if the actual coordinates NRx, NRy, which have numerical values, are outside the rectangle enclosing the region on the circumference. If the coordinate being tested or the other coordinate in the pair falls outside of the rectangle, the test coordinates ptx and pty will be set to zero for that region. The two coordinates will pass all the questions in the negative only once for one of the regions. For this region, ptx, pty becomes NRx, NRy.

Figure 51:
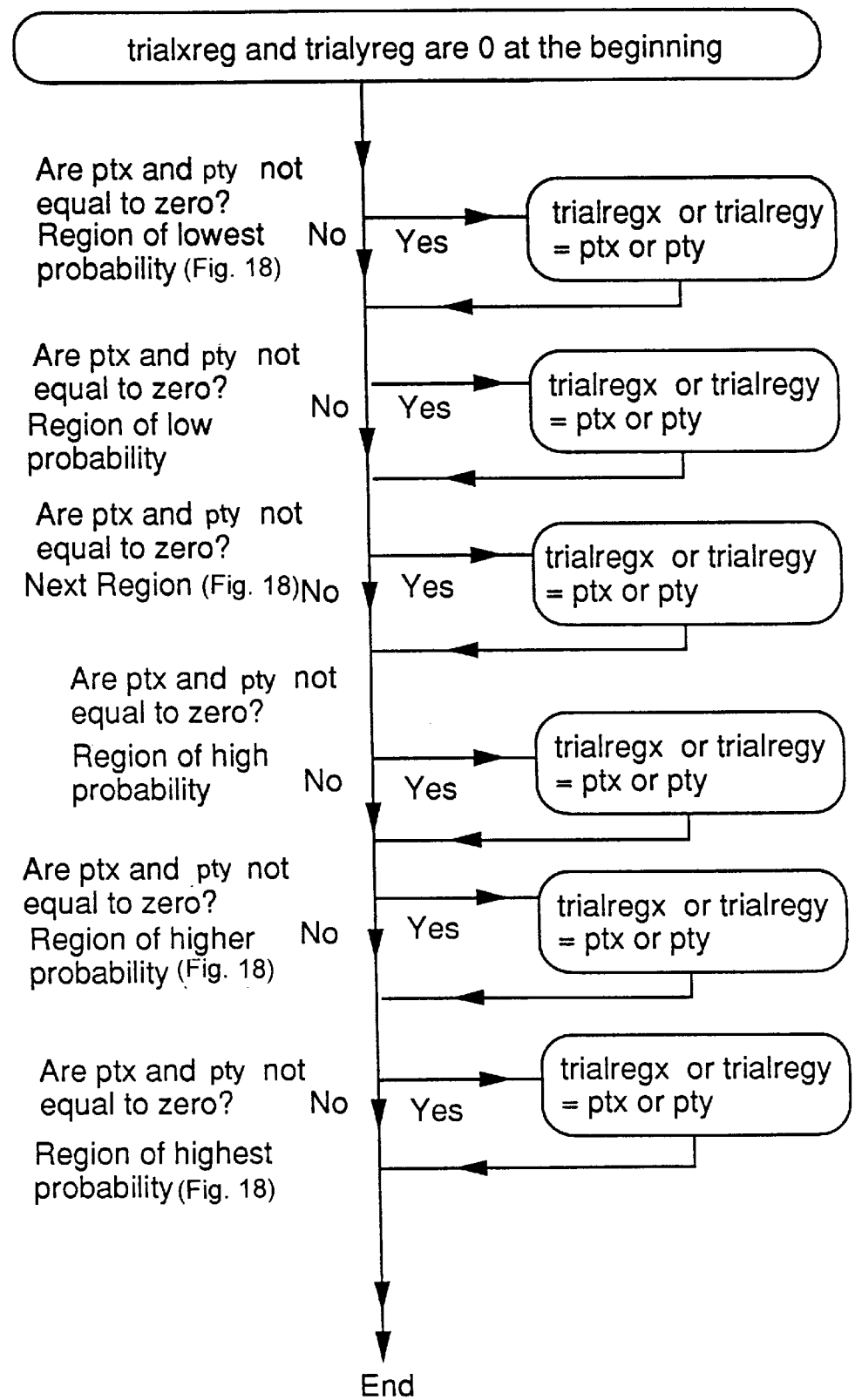

FIG. 51 shows the sequences for Assign Pts discussed in the last section. The point ptx, pty now has a numerical value from the bounding just described. The points trialxreg, trialyreg are test coordinates that begin 0, 0 and are abbreviations for a trial x coordinate in a region and a trial y coordinate in a region.

The routines in FIG. 51 are assigning points 1 and 2 in FIGS. 20 to 22 or points 1, 2, 3, and 4 in FIG. 23. The computer code does this based upon the probability of a point 1, 2, 3 or 4 being in a particular region on the circumference of the ellipse. In FIGS. 20 and 21 the point 2 and in FIG. 22 the point labeled 3, for example, will lie on the upper half of the ellipse when the ellipse is viewed in its local x', y' coordinate system. Point 2 will therefore have a high probability of lying in regions 1a, 2 or 4a on the upper half of the ellipse but not in regions 1b, 3 or 4b. Similarly, the point 3 in FIG. 23, for example, will probably lie in region 4a in FIG. 18 but not in region 1b.

In FIG. 51, there a test pair of coordinates trialxreg, trialyreg begins at 0, 0 at the top of the chart. Continuing downward, it is then asked whether ptx, pty with a numerical value other than 0, 0 actually lies in a particular region. Note that from the bounding procedures in FIGS. 49 and 50 that ptx, pty will be 0, 0 unless it is in one particular region.

At the end of FIG. 51, the coordinates trialregx, trialregy will be the nonzero point ptx, pty in the region of highest probability in which it will be found or in one of the regions of higher probability on the lower end of the chart. The coordinates trialregx, trialregy then become one of the points 1, 2, 3 or 4 in the FIG. 20, 21, 22, or 23 mentioned. The process in FIG. 51 is repeated for each point 1, 2, 3 or 4 needing to be assigned.

Figure 52:
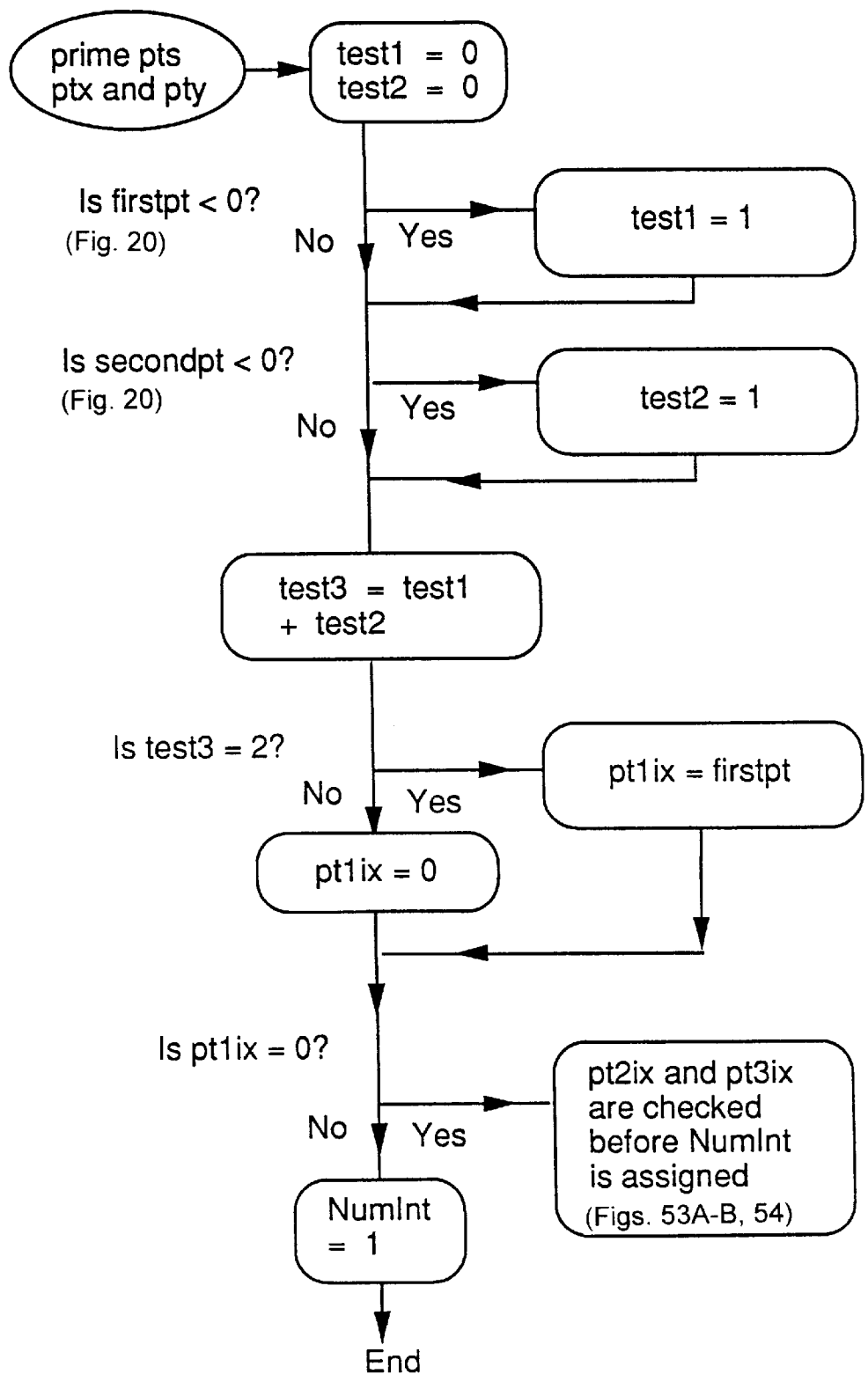

For the situation illustrated in FIG. 23, points 1, 2, 3 and 4 will have been placed by the end of the routines in FIG. 52. For the cases in FIGS. 20, 21 and 22, a point will have been placed on the lower half of the ellipse and a point labeled 2 will have been placed on the upper half of the ellipse. It then remains to be determined which of the configurations in FIGS. 20 to 22 is occurring, which is the purpose of the procedures abbreviated Collect Pts in FIG. 55 and shown in more detail in FIGS. 52, 53A, 53B and 54.

Figure 54:
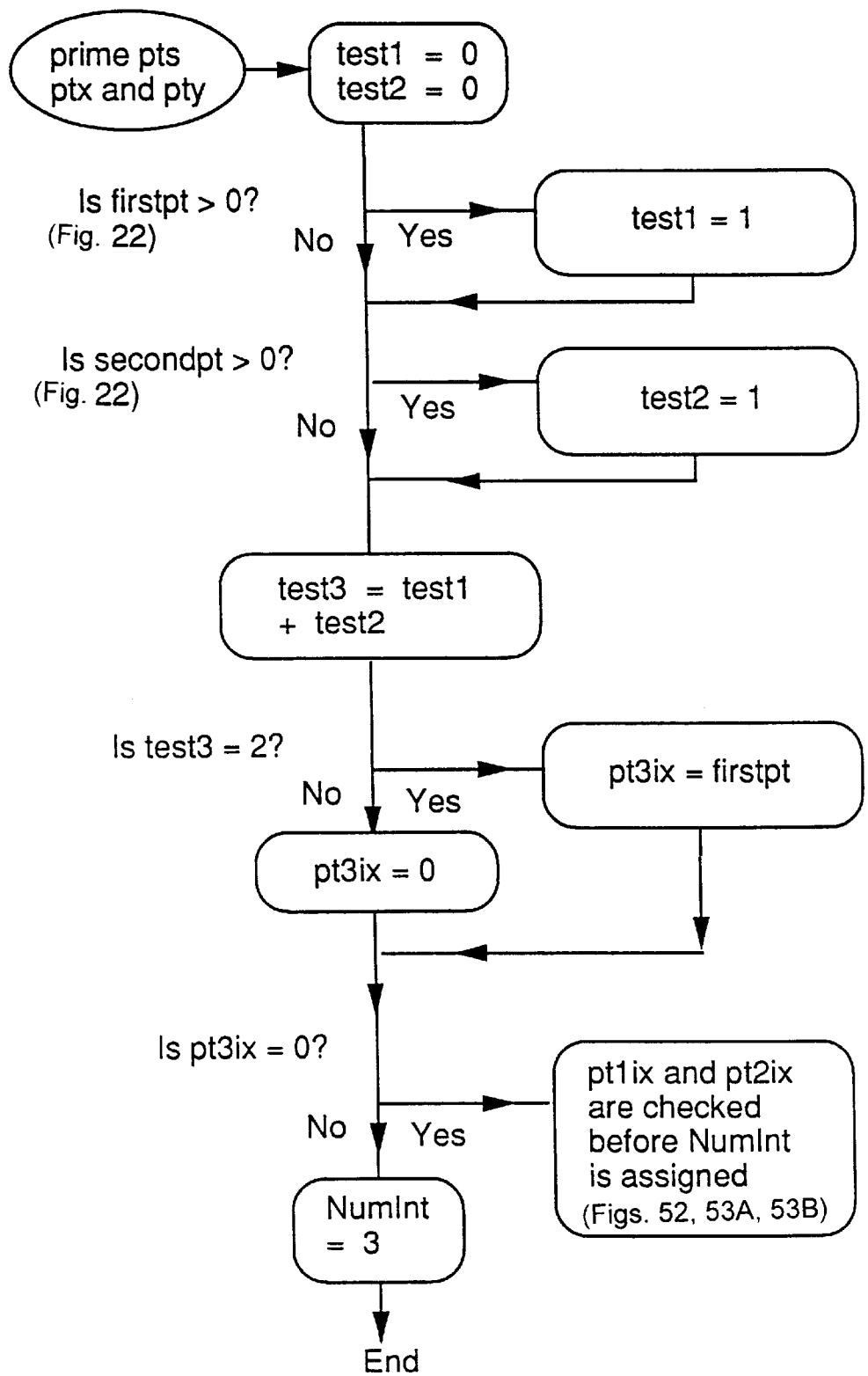

FIGS. 52 and 54 determine whether the intersection points 1 and 2 or 2 and 3 are in the configurations of FIGS. 20 and 22 respectively. The routines are fairly simple because in either case, the points both lie on either the left or right hand side of the ellipse.

Accordingly, both points 1 and 2 or 2 and 3 are put in x', y' coordinates at the top of FIGS. 52 and 54 in the step abbreviated "prime pts". Two intermediate flags, labeled test1 and test2, are set to 0. Test1 and test2 can take values of either 0 or 1. The abscissa of the coordinate pair trialregx, trialregy having numerical values for point 1, for example, is now firstpt. Similarly, the abscissa of the coordinate pair trialregx, trialregy for point 2, for example, is now labeled secondpt.

The charts continue downward to ask if both firstpt and secondpt are less than or greater than zero. In the x', y' coordinate system, this is the same as asking if they are both on the left or right hand sides of the ellipse. If the two abscissas are on the correct side of the ellipse for the number of integrations with respect to x' being tested for, test1 and test2 both become 1. A final flag of test3, the sum of test1 and test2, will then be 2 and an abscissa pt1$ix$ or pt3$ix$ for 1 or 3 integrations as needed will be assigned to firstpt. Firstpt now has a label with the number of integrations needed. NumInt comes from a function that reads ptl$ix$, pt2$ix$ and pt3$ix$ as inputs and returns a number 1, 2 or 3 depending upon which abscissa is nonzero.

Figure 53A:
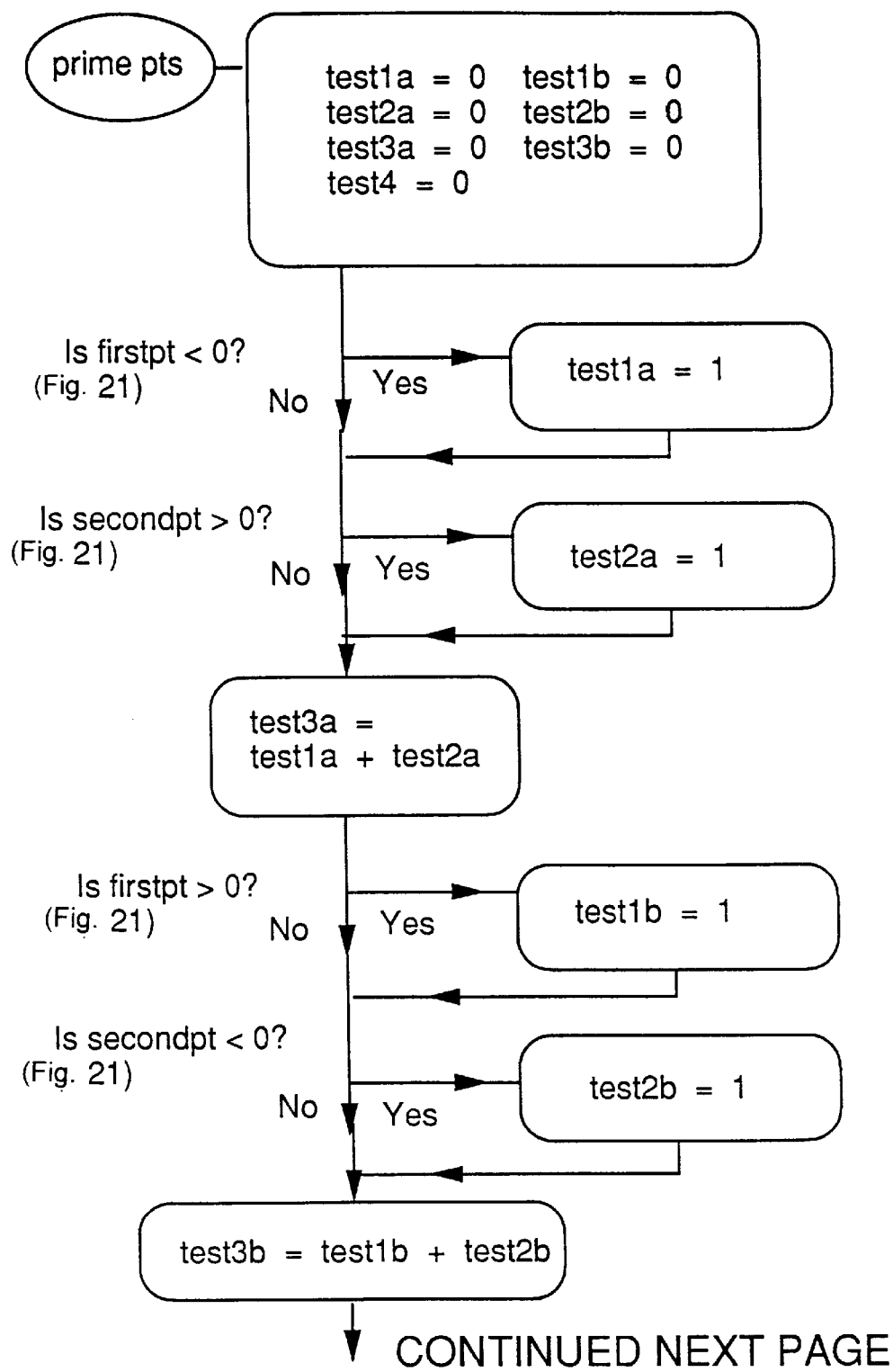
Figure 53B:
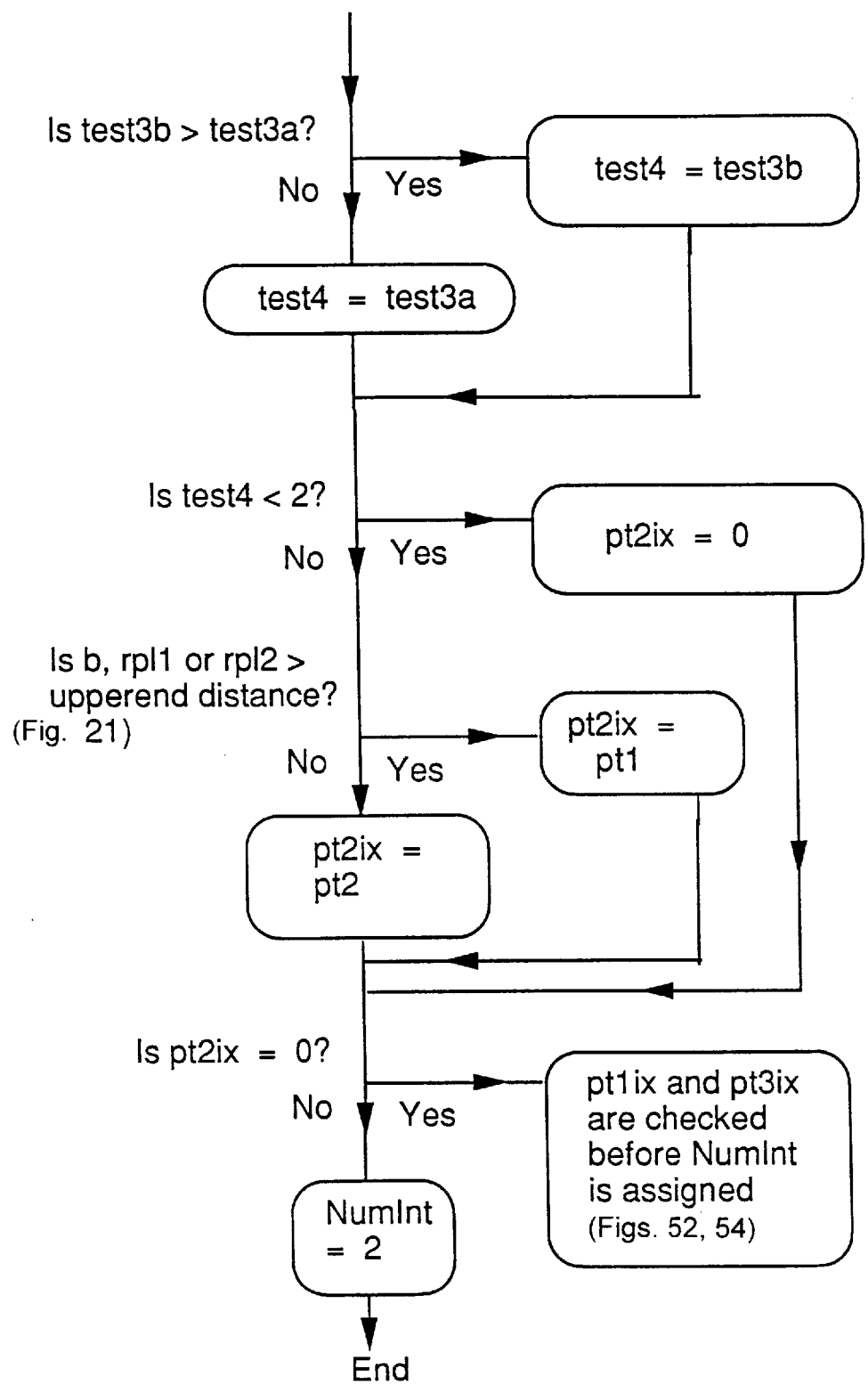

The flow chart of FIGS. 53A and 53B, showing the sequence for the assignment of pt2$ix$, is more involved because it determines which of points 1 or 2 in FIG. 21 is at the boundary where limits for integration with respect to x' will be between the left and right hand sides of the ellipse. Pt2$ix$ will eventually be the other point where integration with respect to x' between the circle and ellipse ends without switching to the left and right hand sides of the ellipse. In FIG. 21, for example, pt2$ix$ would become the abscissa of point 1.

At the top of FIG. 53A, the points are once again put into the x', y' system. The flags test1$a$ and test1$b$, which can have values of 0 or 1, correspond to firstpt. Similarly, the flags test2$a$ and test2$b$ correspond to secondpt.

Continuing downward on FIG. 53A, the first four questions are asking if the abscissas of points 1 and 2 are on opposite sides of the ellipse. If this holds true, one of the pairs of flags test1$a$ and test2$a$ or test1$b$ and test2$b$ together will add up to 2, making either the flag test3$a$ or test3$b$ equal to 2.

The next step, shown at the top of FIG. 53B, is assigning a flag test4 to the larger of test 3$a$ or test3$b$, if one is larger than the other. It is then assured that test4 gets a value of 2 if either test3$a$ or test3$b$ is 2. The next question is asking if test4 is 2, and, if it is not, the flow of software exits the chart because one of the situations in FIG. 20 or 22 is occurring.

Otherwise, FIG. 53B continues downward to ask whether the radius of the circle in question larger than the distance to the upper end of the ellipse. pt2$ix$, as described previously with respect to limits for x' in integration, will always lie on the end of the ellipse that is opposite to the end whose distance from the crack tip is less than the radius of the circle. An example of pt2$ix$ is the abscissa of point 1 in FIG. 21.

IVB.7 Processes Involving Rotation of Rigid Elliptical Entities or a General Modification of a Stress Field Using the $\rho$, $\eta$ Coordinate System (FIGS. 8, 32–34)

There are programs in the system that allow the change from the x', y' coordinate systems to the $\rho$, $\eta$ coordinate system shown in FIG. 8. The $\rho$, $\eta$ coordinates are sometimes convenient to use around the ellipse because on the boundary between the ellipse and material 1 $\rho$ is equal to 1. $\rho$ is a constant along elliptical contours surrounding the center of the ellipse. $\eta$ is an angular coordinate orthogonal to the $\rho$ direction extending outward at a right angle from the elliptical contours.

The present system contains programs that allow calculation of compressive stresses in material 1 due to the rotation of rigid elliptically shaped entity under the applied stress. The compressive stresses help counteract the concentrated tensile stresses near the crack tip and are an example of a modification of a stress field discussed in section I.

Figure 32:
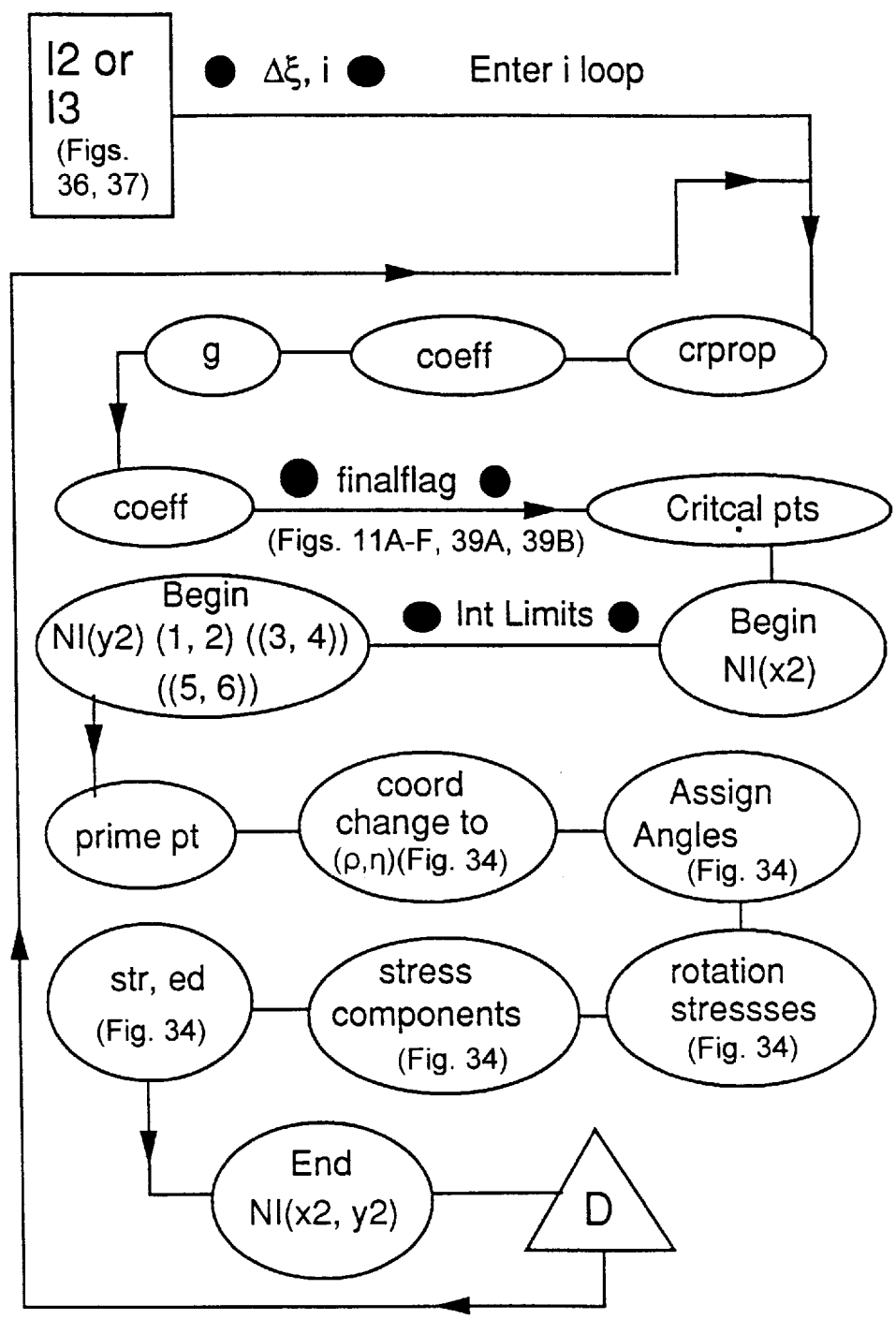
FIG. 32 is a flow chart for programs involving rotation of elliptically shaped entities or modification of elastic stress fields for calculating energy release just above and below the increment of crack advance.
Figure 33:
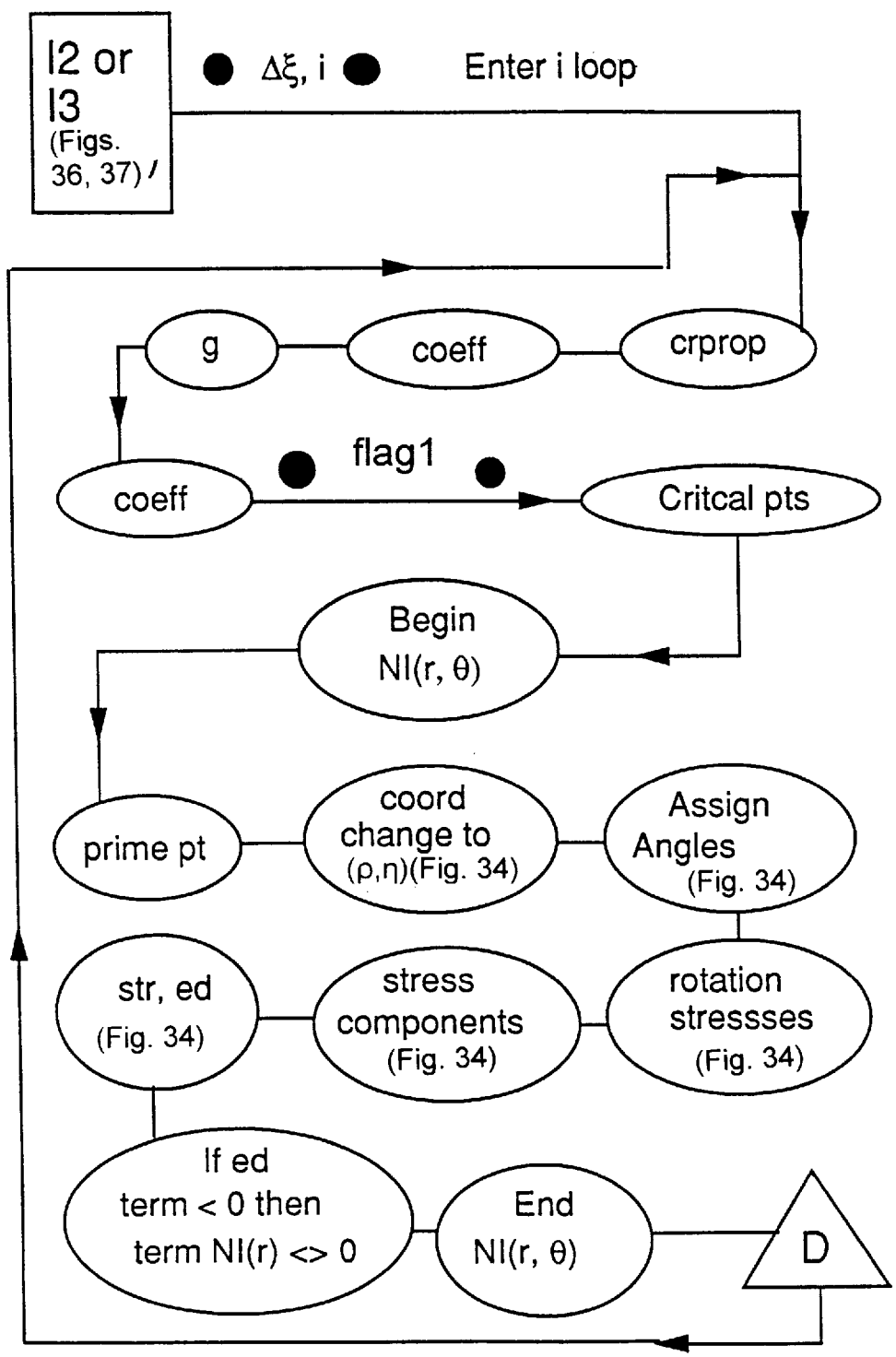
FIG. 33 is a flow chart for programs involving rotation of elliptically shaped entities or modification of elastic stress fields for calculating energy potentially absorbed in areas about the crack tip.

An overview of the flow of software for these programs is shown in FIGS. 32 and 33. FIG. 32 is analogous to FIG. 38 discussed in sections IVA.1 and IVB.1 in that it involves energy released or absorbed just in front of the crack tip with the region of width $\Delta\xi$. FIG. 33 is analogous to FIG. 58 discussed in section IVB.4 and IVA.2 in that it shows the flow of routines for strain energy within the circle of radius b. Some of the basic features of FIGS. 32 and 33, particularly the upper portions before numerical integration begins, were discussed in sections IIB.1, IIB.3, IVB.1 and IVB.3.

The basic difference is in the middle of the charts after numerical integration begins where the stresses due to the rotation of a rigid elliptically shaped entity are calculated. These processes are in more detail in FIG. 34 but an overview will be presented here.

After the numerical integration begins in FIGS. 32 and 33 in either the x2, y2 or r, $\theta$ coordinate system, the immediate point x2, y2 or r, $\theta$ having numerical values for coordinates is changed to the x', y' coordinate system. The step "Assign Angles" refers not to the then changed to the $\rho$, $\eta$ coordinate system. The step "Assign Angles" refers not to the assignment of limits of integration but to various angles to calculate the additional stresses in material 1 due to the rotation of the elliptically shaped entity. The step "rotation stresses" is the actual calculation of stresses due to the rotation and "stress components" is the process of getting the components of the stress from rotation back into the r, $\theta$ coordinate system that counteract the concentrated tensile stresses from the crack in the r, $\theta$ coordinate system.

Figure 34:
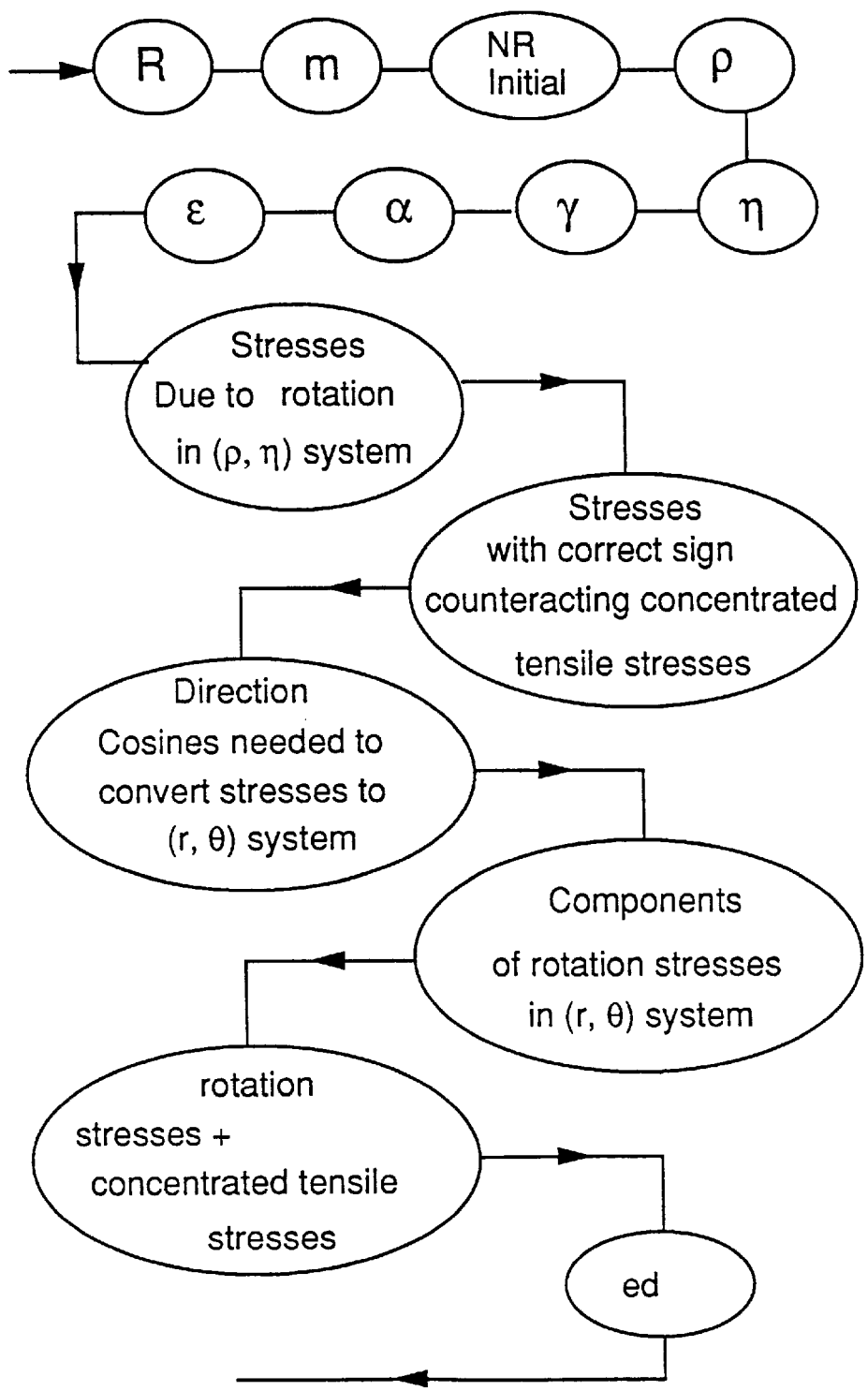
FIG. 34 is a flow chart for programs involving modification of elastic stress fields.

The steps just outlined in the last paragraph are shown in more detail in FIG. 34. The first seven parameters, R, m, $\rho$, $\eta$, $\gamma$, $\alpha$ and $\epsilon$, are parameters used to calculate the stresses due to rotation[4] indicated in the next step in the chart.

R and m are parameters describing the size and character of the ellipse similar to the manner in which the length of the major axis k and minor axis j do. R and m are related to k and j by the relations k=R(1+m) and j=R(1-m), making R a measure of the general size of the ellipse and m its eccentricity. When m is 0, the ellipse degenerates into a circle and when m approaches 1, it elongates to a long narrow entity. The function that assign R therefore uses k and j as inputs and that of m uses j and R as inputs.

$\rho$ is assigned by using a Newton-Raphson method to find the root of a polynomial equation of the form $d_1\rho^8 + d_2\rho^6 + d_3\rho^4 + d_4\rho^2 + d_5 = 0$. The two equations relating x' and y' to $\rho$ and $\eta$, which are given by $x' = -R(\rho - (m/\rho))\sin\eta$ and $y' = R(\rho + (m/\rho))\cos\eta$. In these calculations, the angle $\eta$ is measured counterclockwise and begins at a value of 0 at the line coinciding with the positive y1 axis in FIG. 8 along which k is measured.

Once x' and y' are set with numerical values after beginning numerical integration and from converting a particular point in the integration from either the r, $\theta$ coordinate system or the x2, y2 coordinate system to the x, y' coordinate system, $\eta$ can be eliminated from the two equations just mentioned for x' and y' to yield the polynomial equation for $\rho$ at the beginning of the last paragraph in which the coefficients d1 to d5 have numerical values. The procedure to assign d1 to d5 therefore uses x', y', R and m as inputs. The step "NR initial" after the calculation of R and m in FIG. 34 refers to assigning an initial value for $\rho$, usually set at 1.2, to begin a Newton-Raphson routine[3] to solve the polynomial equation for $\rho$. The function for $\eta$ uses in turn x', y', R, m and $\rho$ as inputs and uses the same equations for x' and y' just discussed to assign $\eta$.

The next step in FIG. 34 is the calculation of $\gamma$. $\gamma$ is an angle between unit vectors in the r and $\rho$ directions and is used later to get components in the r, $\theta$ coordinate system of the stresses from rotation that are originally in the $\rho$, $\eta$ coordinate system. The step "Direction cosines . . . " further down refers to assigning sines and cosines of this angle $\gamma$, commonly known as direction cosines that are used to get components of quantities along various axes. They are later used to convert a stress from rotation in the $\rho$, $\eta$ coordinate system to the r, $\theta$ coordinate system.

The procedure that produces the set of direction cosines uses the angle $\gamma$ as an input. The outputs of the procedure are trigonometric functions of the angles between the $\rho$, $\eta$, r and $\theta$ directions and of the angles between the planes normal to these directions.

The procedure for the next step labeled "components of rotation stresses . . . " is actually assigning components in the r, $\theta$ coordinate system of the rotation stresses in the $\rho$, $\eta$ system found three steps earlier. The procedure uses as inputs the normal stresses in the $\rho$ and $\eta$ directions and the shear stress in the $\eta$ direction on a plane perpendicular to the $\rho$ direction that are from the rotation. It also uses all the direction cosines mentioned in the previous paragraph as inputs. From standard equations relating the stresses in one coordinate system to those in another coordinate system[1], the procedure produces as outputs normal stresses in the r and $\theta$ directions and the shear stress in the $\theta$ direction on a plane perpendicular to the r direction.

Returning to the angle $\gamma$, the function that returns it uses R, m, $\eta$, j, k, x2 and y2 as inputs. The angle is calculated at some point with numerical coordinates x2, y2 in the x2, y2 coordinate system and is the angle between the unit vectors in the r and $\rho$ directions at that point. The angle is calculated using the gradient vector to the ellipse, which is perpendicular to the circumference of the ellipse but in the same direction as a unit vector in the $\rho$ direction.

The function used to assign $\gamma$ is developed from a function $f(x', y') = k^2 x'^2 + j^2 y'^2 j^2 k^2 = 0$ for the circumference of the ellipse in the x', y' coordinate system. A gradient vector g is written first from the function f in the x', y' coordinate system. From the equations in section IVB.1, the unit vectors in the x' and y' directions in the gradient vector g can changed to a set of unit vectors in the x2 and y2 directions. A vector r in the r direction at the same point in question is x2<u>x2</u>+y2<u>y2</u> where <u>x2</u> and <u>y2</u> are unit vectors in the x2 and y2 directions respectively. The angle $\gamma$ is then found from a product between the two vectors r and the gradient vector g, which is a product of the magnitudes of the vectors multiplied by the cosine of the angle $\gamma$.

The last two parameters assigned in FIG. 34 before the calculation of stresses due to rotation are $\alpha$ and $\epsilon$. $\alpha$ is the larger of the two angles between the direction of the positive y1 axis of the ellipse in FIG. 8 and the line of the applied stress discussed at the beginning of section IIB.1. The function that assigns it uses the angle $\beta$ in both degrees and radians as inputs.

$\epsilon$ is the actual angle of rotation of a rigid elliptically shaped entity and is found in section 83a of reference 4. The function that assigns it uses the applied stress, E1, m, $\alpha$ and $\kappa$ as inputs, where $\kappa$ is the constant $3-(4\times v1)$.

Expressions for the compressive stresses due to the rotation of a rigid elliptically shaped particle may be found from two complex functions in section 83a of reference 4 and by equations given in section 50 of the same reference. The function itself in the computer system that assigns the stresses uses the applied stress, R, m, E1, ε, α, ρ, η and the constant κ in the last paragraph as inputs.

Figure 24:
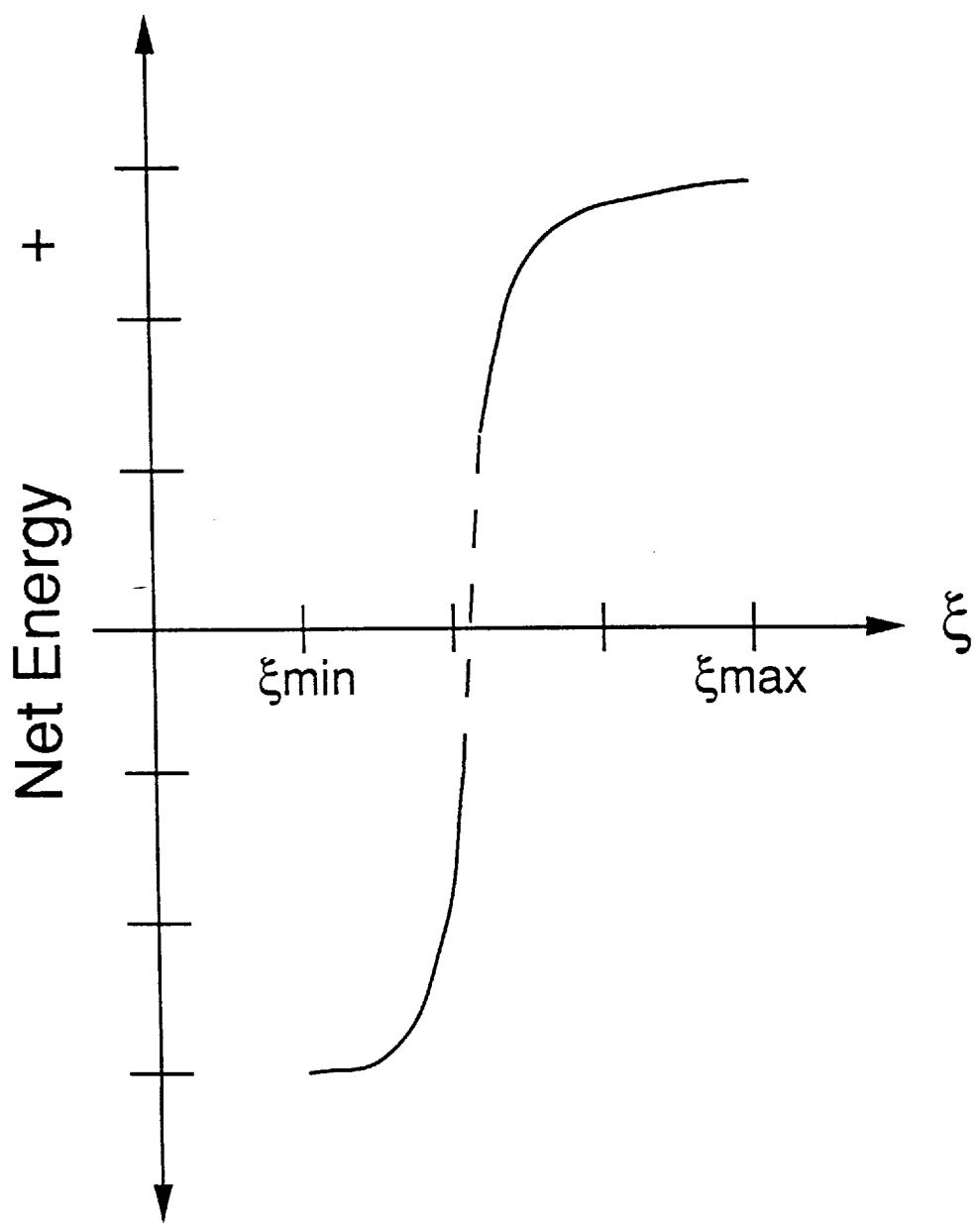
FIG. 24 shows a schematic of a graph of net energy change versus crack distance from the interface.
Figure 65:
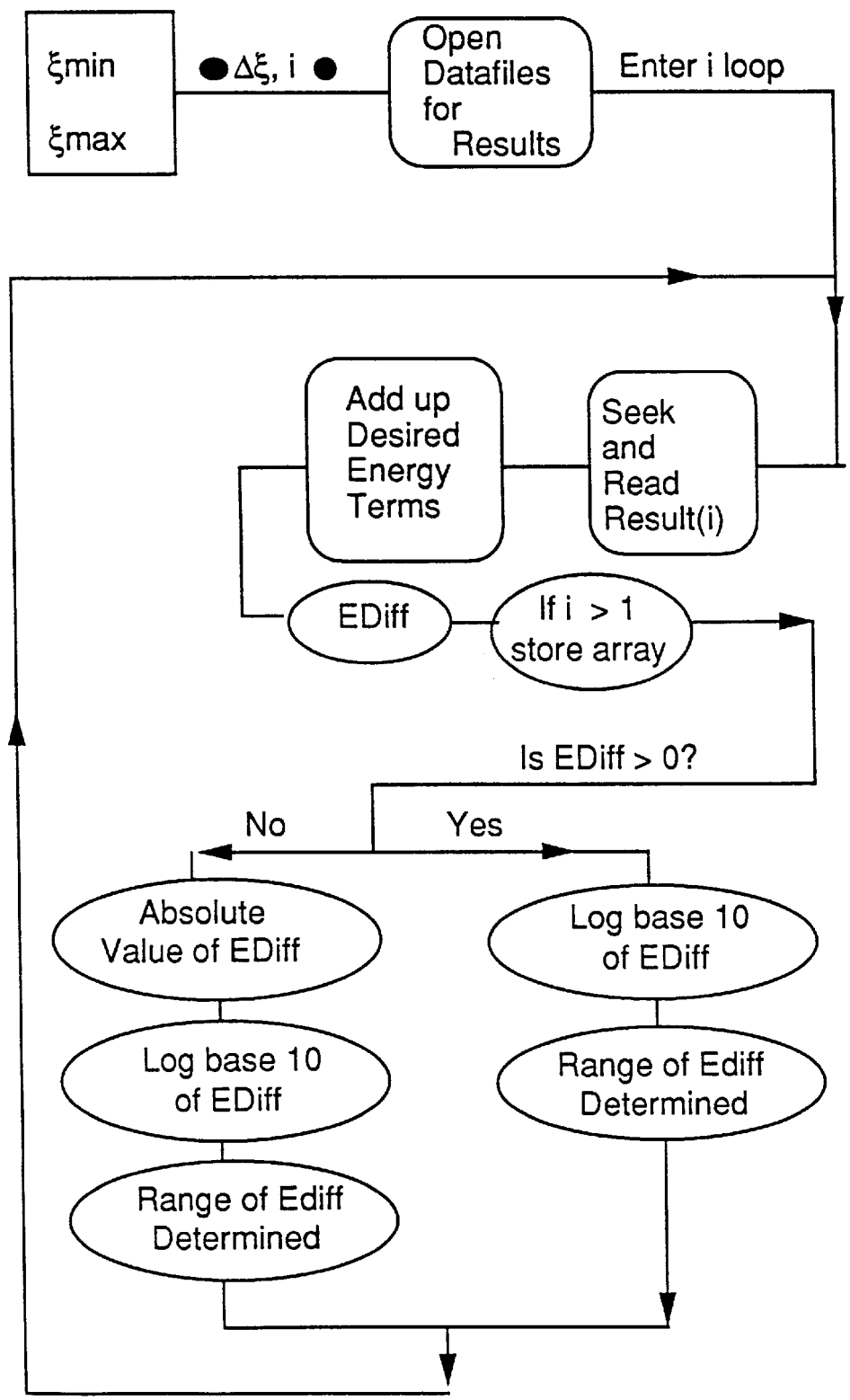
FIGS. 65 and 66 are flow charts for routines for graphics.
Figure 66:
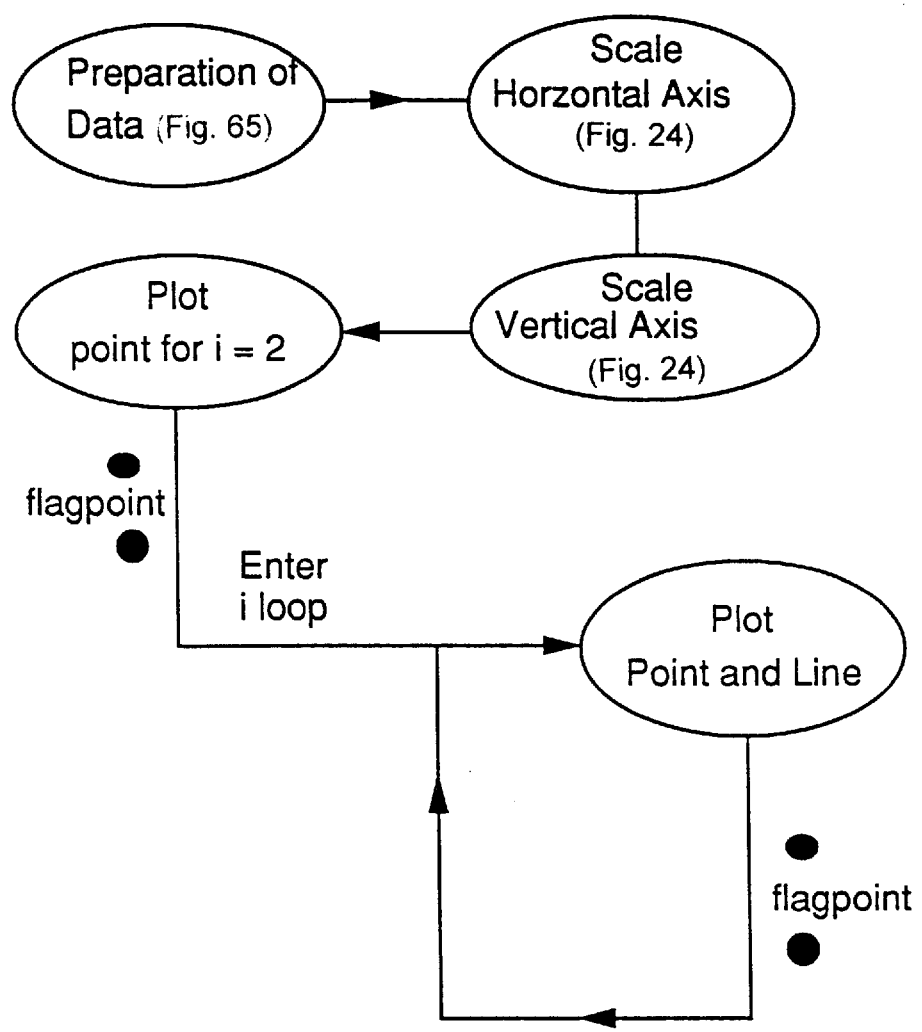

V. Production of a Graph (FIGS. 24, 65, 66)

VA. Introduction

The computer system allows a user to look at a graph at the end. The graph is automatically scaled to fit the results generated within the programs and to fit the initial and final distances of the crack tip from the interface first selected by the user. The graph is of the total net amount of energy being absorbed and released per increment of crack advance as a function of the distance of the crack tip from the interface and is shown schematically in FIG. 24.

VB. Preparation of Data (FIGS. 24 and 65)

FIG. 65 shows the flow of software for the preparation of data from the programs for the graph. As shown at the top of the chart, the user is first asked to key in the values of $\xi_{min}$ and $\xi_{max}$ used throughout the programs that were used to generate a set of energies in memory. i is then calculated because a loop similar to those for crack advancement will be entered to process data at each increment of crack advance. $\Delta \xi$ is again calculated not only to obtain the maximum counting integer i for the loop, but to calculate later the total change in energy per incremental length $\Delta \xi$ of crack advance.

In the next step, the data files containing the results found from running the programs and that were discussed in section IIIB.2 are opened. A loop of maximum counting integer i is entered, with each circuit of the loop corresponding to a different crack position. Once inside the loop, the energy results are sought and read for that particular crack position. At each crack position, the value of $\xi$ is also calculated and stored later in an array variable to be used later for scaling and marking the horizontal axis.

The next step is that the energy terms for a particular crack position are added up. At this point a user can adjust some of the assignment statements to look at all or a portion of the energy terms being generated as the crack advances. The term "EDiff" in the next step is the sum of the energy terms from the data files divided by $\Delta \xi$.

Moving to the right in the chart, the next step is storing EDiff and $\xi$ in one dimensional array variables. During production of a graph, small loops of maximum counting integer i are entered and values of EDiff or $\xi$ are recalled as needed.

The reason the data is stored for i>1 is that the crack position for i=1 is at the end of the advancement near the interface. As discussed in section IIB.4, during calculations the crack actually begins at the interface and backs up from the interface. Since most of the energy terms are differences between successive crack positions when the crack is moving forward, the energy term for i=1 was used to calculate an energy difference between the last and second to the last positions of the crack near the interface and is not used as a data point by itself on the graph.

The net energy terms themselves, even for a crack moving about 10 microns near an entity, do not differ by one or ten percent but often by one to three orders of magnitude (factor of 10 to a thousand or more). Consequently, the log base 10 of EDiff is taken before graphics to have the results scale easily on the vertical axis.

The net energy terms can also be positive or negative. The energy terms are also divided up into two groups depending upon whether they are positive or negative.

Of the next step after "store array", the dividing of the data into positive and negative terms and taking a logarithm base ten of each term is often done in small loops during the graphics. If the net energy term is negative, its absolute value is taken before its logarithm, but the term itself is plotted on the lower portion of the graph depicted in FIG. 24.

The range of EDiff is determined within the loop shown for both groups of positive and negative values of EDiff. The range is used later to put tic marks and labels at appropriate intervals along both the upper and lower portions of the vertical axis.

As the loop for the crack positions circulates, the range of EDiff for positive values of EDiff, for example, is determined by setting initially two temporary variables at the ends of but far outside of the ends of possible ranges of EDiff. A minimum of the logarithm base 10, for example, is first set at 50 and a maximum at −50. The next value of the logarithm of EDiff of course is less than the minimum and greater than the maximum, so the two temporary variables at the ends of the range are set to this logarithm of EDiff. Each time a logarithm of an EDiff value is either less than the immediate minimum or greater than the immediate maximum of the range being accumulated, as expressed by these two temporary variables, one of the variables is reassigned to the logarithm of that particular EDiff value.

At the end of circulating the loop i times, the two temporary variables will then have the minimum and maximum of the values of the logarithms of EDiff for the entire crack advance. If none of the values of Ediff before logarithms are taken happen to be positive or if none are negative, default values for the ends of a range are set before scaling that half of the vertical axis.

VC. Production of a Graph

FIG. 66 shows the flow of software for the production of a graph. The commands used to plot points themselves and to draw lines are contained within Turbo Pascal and its standard graphics unit called Graph. Of course, if another programming language is used, the corresponding graphics unit is called. The description here focuses on parameters generated within the computer system herein described that correctly scale the axis and data, the functions that directly use these parameters and the character of the graph itself.

After the preparation of data shown in more detail in FIG. 65 and discussed in the last section, the horizontal axis is scaled with tic marks and labeled with values of $\xi$. $\xi_{min}$ and $\xi_{max}$ are used as inputs to assign a range number, which is based upon the difference between $\xi_{max}$ and $\xi_{min}$. When the difference is less than 2, the range number is simply the difference, and when the difference is greater than 2, the range number is the difference rounded to the nearest integer.

Another function then uses the range number as an input to assign an interval number, which basically assigns the number of tic marks that will appear. A final function for the interval between tic marks uses the range number, the interval number and the pixel range on the screen to assign the interval as the interval number divided by the product of the range number and the pixel range.

The tic marks and labels for $\xi$ are plotted in a small counting loop. The maximum integer for the counting numbers for the loop is the range number divided by the interval number rounded to the nearest integer. For plotting the tic marks and labels, $\xi_{min}$ is rounded to the nearest integer. Tic marks are put at a starting pixel added to a quantity that is the counting integer multiplied by the interval number. Labels begin at $\xi_{min}$ rounded to the nearest integer added to the product of the counting integer and the interval number.

Scaling and marking both the upper and lower portions of the vertical axis in FIG. 24 works in a similar manner. The range of logarithmic values for both portions of the vertical axis are found by taking differences between the ends of the ranges for the logarithms of the results that were discussed in section VB. The maximum counting integer that scales each axis is set to one of these differences added to the integer 2 so that the scale of the axes is a little larger than the range of data points.

The placement vertically of a data point itself uses a variable that is the a quantity that is the logarithm of EDiff minus the minimum value in the range of results divided by the maximum counting integer described in the last paragraph. Similarly, the placement of the data point horizontally uses a variable that is a quantity that is the difference between $\xi$ for the data point and the minimum value for the range of $\xi$ divided by the range number for $\xi$.

The lower part of FIG. 66 shows that after i=2, points and connecting lines are plotted for i greater than or equal to 3. The flag called flag point gets a value of 0 or 1 depending upon whether the last data point plotted was on the upper or lower portion of the graph. The flag is used to connect points for positive energy with solid lines of one color and points for negative energies with solid lines of another color. The flag is also used to place a dotted line between adjacent points that are on opposite sides of the horizontal axis, as shown in FIG. 24.

LISTING OF ABBREVIATIONS AND TERMS USED IN THE FLOW CHARTS $\Delta\xi$—increment of crack advance i—size of counting integer controlling the size of the loop changing the crack positions Assign Angles—Procedures needed to assign angles such as g, a and e that are used to get stresses arising from rotation and their components in the r and q directions.

Assign Pts—The results from Bound Pts are checked and point assignments are made for the upper and lower parts of the ellipse based upon the probability of finding the point in one of the upper or lower regions.

Bound Pts—Regions on the perimeter of the ellipse are checked for intersection points found by the Newton-Raphson Method.

coeff—coefficients of the equation for the ellipse in the X2, Y2 coordinate system.

Collect Pts—procedures that determine whether the ordinates of the points assigned in Assign Pts fulfill the conditions for one, two, or three numerical integrations to be performed to cover the overlap area on the ellipse and assigns a label to each ordinate denoting the number of integrations Coord Change—procedures to change coordinate systems to facilitate handling formulas in a different coordinate system Critical Pts—points on an ellipse representing an elliptically shaped entity where the slope is either zero or infinity.

Diff(i)—Difference is taken between the final energy term in the loop of counting number i and that of counting number i-1.

Endpt Distances—distances from the crack tip to the ends of an elliptically shaped entity where x' is zero are calculated, the coordinates of the endpoints in the x2, y2 coordinate system are calculated, and the distances along the crack path to both sides of the ellipse when the ellipse intersects the crack path are calculated.

Energy Terms—Results of numerical integration are combined with various elastic constants to produce final energy terms.

Finalflag—a combined flag of two digits determining where the radius b of elasticity and the radius of plasticity of material 2 is with respect to the second material.

flag1—flag determining where the radius of plasticity of material 1 or material 2 is with respect to the second material flagpoint—flag determining whether the energy term just previously plotted was positive or negative so that connecting lines of negative energy terms, of positive energy terms and of lines between them may collectively be of different colors or styles.

i loop—main loop changing the crack positions.

Intersection Pts—A collection of procedures to find intersection points and get them ready as limits for numerical integration.

Int Limits ( )—Limits of integration for the variable in parentheses.

Int Pts NR CE—Intersection points between the circle and the ellipse are obtained by a Newton-Raphson method for two nonlinear equations.

Mat 1—pertaining to material 1

Mat 2—pertaining to material 2

NI( )—numerical integration with respect to the variable (s) in parentheses.

NR Initial—coordinates of points based on results of Critical Pts used to start the Newton-Raphson routines to get the shortest distances in Shortlengths. p1 NumInt—procedures for assigning NumInt, the number of regions in the overlap over which numerical integration is to be performed, depending upon how many times the function for x' as a function of y' changes when needing to get limits of integration for x'.

PlotPoint—functions and procedures that take the logarithm of a result for a crack position prepared previously under Preparation of Results and plots it accordingly on the graph and draws a connecting line whose color and style is determined by flagpoint.

Plot Point and Line—Procedures and functions that plot a datapoint from Preparation of Results in the correct place on the graph and draws connecting lines between points whose color and/or style is set by flagpoint.

plw1(rpl1)—procedures for getting plastic work in material 1 in the entire circular area of radius rp1.

rotation stresses—procedures to assign expressions to stresses arising from rotation of an elliptically shaped entity.

Scale Horizontal Axis—Procedures that scale and mark the horizontal axis according to the range of x originally set by the user.

Scale Vertical Axis—Procedures that scale and mark both the positive and negative portions of the vertical axis based upon the range of results read from the datafiles.

Shortlengths—Procedures to calculate the shortest distance from the crack tip to a microstructural entity and also the distance to the other side of the microstructural entity when the line L from the crack tip to the entity covering the shortest distance is extended to the other side. Coordinates of the intersection points between L and the entity and the angle between L and the crack path are calculated as needed.

store array—The variable or flag determined in the last step in a flow chart is stored in an array variable to be recalled later.

stress components—procedures to get components of rotation stresses in the coordinate system ($\rho$, $\eta$) of the concentrated tensile stress at the crack tip and to get the correct sign of the stresses when they counteract the concentrated tensile stresses.

LISTING OF REPRESENTATIVE PROGRAMS

PROGRAMS FOR DATA FILES AND GRAPHICS

Rfile0—datafiles 1 to 13 filled—sets positions in all files for results or those selected by the user to zero Rtest1—reads results from datafiles, prepares the data for plotting and provides a graph for the results.

PROGRAMS FOR ENERGY RELEASE WITHIN $\Delta\xi$

Itest1—datafile 1 filled—assigns and stores energy released in a narrow region of width $\Delta\xi$ just ahead of the crack when the microstructural entity is elliptically shaped.

Itest2—datafile 1 filled—assigns and stores energy released in a narrow region of width $\Delta\xi$ just ahead of the crack when the microstructural entity is planar.

PROGRAMS FOR ENTITIES WITH PLANAR SIDES

Itest71—datafile 2 filled—mode I elastic energy change between crack positions for a full circular area about the crack tip and the second material is planar.

Itest72—datafile 3 filled—mode II elastic energy release between crack positions.

Itest73—datafile 4 filled—elastic energy change to be subtracted out of the results of Itest71 and Itest72 when part of material is plastically deforming.

Itest74—datafile 5 filled—assigns plastic work in material 1 for each increment of crack advance.

Itest75—datafile 6 filled—assigns plastic work in material 2 for each increment of crack advance.

PROGRAMS FOR ELLIPTICALLY SHAPED ENTITIES

I5full—datafile 2 filled—assigns total elastic energy in the circular region or its difference between crack positions taking into account the presence of the elliptically shaped entity.

Itest50—datafile 11 filled—assigns plastic work in the elliptically shaped entity.

Itest60—datafile 2 filled—assigns elastic energy in modes I and II when the circular region does not overlap with the elliptical entity.

Itest61—datafile 2 filled—one numerical integration is required to cover the region of overlap.

Itest62—datafile 3 filled—two numerical integrations are required to cover the region of overlap; program integrates between the end of the ellipse and its nearest intersection point.

Itest63—datafile 2 filled—two numerical integrations are required to cover the region of overlap; program integrates between the two intersection points.

Itest64—datafile 3 filled—three numerical integrations are required to cover the region of overlap; program integrates between the two intersection points.

Itest65—datafile 2 filled—three numerical integrations are required to cover the region of overlap; program usually integrates between the lower end of the ellipse and the intersection point with the lower y' ordinate.

Itest66—datafile 4 filled—three numerical integrations are required to cover the region of overlap; program usually integrates in the region between the upper end of the ellipse and the intersection point with the higher ordinate in the (x', y') system, which is the end region not covered in program Itest65.

Itest67—datafile 2 filled—circular region overlaps with the elliptical entity by extends back into material 1 outside the elliptical entity; program integrates between the two intersection points with the lowest ordinates in the (x', y') system.

Itest68—datafile 3 filled—circular region overlaps with the elliptical entity but extends back into material 1 outside the elliptical entity; program integrates between the two intersection points with the greatest abscissas in the (x', y') system.

Itest69—datafile 4 filled—circular region overlaps with the elliptical entity but extends back into material 1 outside the elliptical entity; program integrates between the two intersection points with the greatest ordinates in the (x', y') system.

MEANING OF LABELS ON OTHER PROGRAMS

Other series of programs integrate over the same types of regions as those listed except that the circular area may involve, for example, plastic work within the radius of plasticity of material 1. The 40's series assigns plastic work in material 1, the 50's series plastic work in material 2 and the 80's series subtracts out elastic energy in regions of the second material where there is plastic work.

Program Itest51, for example, calculates plastic work within the radius of plasticity of material 2 in the region where the circular area for potential plasticity overlaps with the elliptical entity. Like Itest61, the program runs to completion for each crack position at which the overlap requires one numerical integration to be covered. Itest85, for another example, subtracts out elastic energy within the radius of plasticity of material 2, and like Itest65, runs to completion when three numerical integrations are required to cover the region of overlap and then integrates between the lower end of the ellipse and the intersection point with the lower ordinate in the (x', y') system.

MEANING OF DIGIT IN HUNDREDS PLACE OR 100, 200 AND 300 SERIES

When the second material is planar, a 1 in the hundreds place (170 series) denotes thicknesses of the second material that is always greater than the radius b of the circular region within which elastic energy is calculated.

For elliptically shaped entities, "approach at a right angle" means that the crack path (or the plane between the open crack surfaces) is at an angle of 90 degrees to the major axis of the elliptical entity.

000 series—crack does not approach the elliptically shaped entity at a right angle and the entity intersects the crack path

100 series—crack does not approach the elliptically shaped entity at a right angle but the entity does not intersect the crack path

200 series—crack approaches the elliptically shaped entity at a right angle and the entity intersects the crack path

300 series—crack approaches at a right angle and the elliptically shaped entity does not intersect the crack path

PROGRAMS INVOLVING THE $\rho$, $\eta$ COORDINATE SYSTEM OR THE ROTATION OF RIGID ELLIPTICALLY SHAPED ENTITIES I1I2rotate—datafile 1 filled—net elastic energy release in the region of width $\Delta\xi$ in front of the crack and of length between the radius of plasticity of material 1 and the radius of elasticity below the crack.

I3I4rotate—datafile 2 filled—same as I1I2 rotate except the length of the region is between the radius of plasticity of material 1 and the boundary of the ellipse.

I5I6rotate—datafile 3 filled—same as I1I2rotate except the length of the region is between the upper boundary of the ellipse and the radius of elasticity above the crack tip.

rregion—datafile 4 filled—elastic energy absorbed or released in all or selected parts within the radius within which elastic energy is calculated.

What is claimed:

1. A series of operational steps to be performed by means of a computing device including a processor, input means for receiving input from a user, and output means for displaying an output to the user, the series of operational steps comprising:

(a) prompting the user, with the output means, for information regarding a material having a crack therein;

(b) receiving the information from the user with the input means;

(c) selecting an increment of crack advance; and (d) in accordance with the information received in step (b) and the increment of crack advance selected in step (c), integrating numerically by means of the processor over a region surrounding a tip of the crack to determine an energy change in the region caused by an advance of the crack by the increment of crack advance selected in step (c).

2. A series of operational steps as in claim 1 further comprising:

(e) performing step (d) repeatedly for successive advances of the crack by the increment of crack advance to obtain a succession of energy changes;

(f) in accordance with the succession of energy changes obtained in step (e), deriving, by means of the processor, a graph of net energy change per unit length of advance of the crack; and (g) displaying to the user, by means of the output means, the graph derived in step (f).

3. A series of operational steps as in claim 2 wherein:

the increment of crack advance has a value $\Delta\xi$;

step (d) is performed i times;

the information received from the user comprises a minimum crack length $\xi_{min}$ and a maximum crack length $\xi_{max}$; and $\Delta\xi$ and i are determined by (i) calculating a difference $\xi_{max}-\xi_{min}$, (ii) determining i in accordance with $\xi_{max}-\xi_{min}$, and (iii) defining $(\xi_{max}-\xi_{min})/i \equiv \Delta\xi$.

4. A series of operational steps as in claim 1 wherein:

the information comprises a radius of elasticity selected by the user;

a circular region within the radius of elasticity of the tip of the crack is defined as the region of elasticity; and the region surrounding the tip of the crack in which the numerical integration of step (d) is performed is at least part of the region of elasticity.

5. A series of operational steps as in claim 4 wherein step (d) comprises calculating elastic strain energy release within a portion of the region of elasticity whose lower and upper boundaries lie along a boundary of the region of elasticity and whose left and right boundaries lie within the advance of the crack, the portion of the region of elasticity excluding any regions of plasticity in the material.

6. A series of operational steps as in claim 4 wherein:

the material comprises a first material region and a second material region, the first material region containing at least part of the crack, the first and second material regions having a material interface therebetween; and the information includes physical information regarding the first material region and the second material region and geometrical information regarding the material interface.

7. A series of operational steps as in claim 6 wherein:

the material interface is one of an elliptical interface and a planar interface; and the geometrical information regarding the material interface comprises an identification of whether the boundary is the elliptical interface or the planar interface and an initial location of the crack tip relative to the material interface.

8. A series of operational steps as in claim 7 wherein step (d) comprises determining regions of overlap between the region of elasticity and the first and second material regions.

9. A series of operational steps as in claim 8 wherein when the material interface is the elliptical interface, the step of determining regions of overlap comprises determining points of intersection between a circle bounding the region of elasticity and elliptical interface by a Newton-Raphson method which is performed in accordance with equations representing the elliptical interface and the circle bounding the region of elasticity.

10. A series of operational steps as in claim 9 wherein the Newton-Raphson method comprises a probabilistic method performed in accordance with test variables entered in step (b) and a probability of finding one of the points of intersection on any particular portion of the elliptical interface.

11. A computing device comprising a processor means for receiving input from a user, and output means for displaying an output to the user, the processor comprising means for controlling the computing device to perform the following operational steps:

(a) prompting the user, with the output means, for information regarding a material having a crack therein;

(b) receiving the information from the user with the input means;

(c) selecting an increment of crack advance; and (d) in accordance with the information received in step (b) and the increment of crack advance selected in step (c), integrating numerically by means of the processor over a region surrounding a tip of the crack to determine an energy change in the region caused by an advance of the crack by the increment of crack advance selected in step (c).

12. A computing device as in claim 11 wherein the processor comprises means for controlling the computer device to perform the following additional operational steps:

(e) performing operational step (d) repeatedly for successive advances of the crack by the increment of crack advance to obtain a succession of energy changes;

(f) in accordance with the succession of energy changes obtained in step (e), deriving, by means of the processor, a graph of net energy change per unit length of advance of the crack; and (g) displaying to the user, by means of the output means, the graph derived in step (f).

13. A computing device as in claim 12 wherein:

the increment of crack advance has a value $\Delta\xi$;

operational step (d) is performed i times;

the information received from the user comprises a minimum crack length $\xi_{min}$ and a maximum crack length $\xi_{max}$; and $\Delta\xi$ and i are determined by (i) calculating a difference $\xi_{max}-\xi_{min}$, (ii) determining i in accordance with $\xi_{max}-\xi_{min}$, and (iii) defining $(\xi_{max}-\xi_{min})/i \equiv \Delta\xi$.

14. A computing device as in claim 11 wherein:

the information comprises a radius of elasticity selected by the user:

a circular region within the radius of elasticity of the tip of the crack is defined as the region of elasticity; and the region surrounding the tip of the crack in which the numerical integration of step (d) is performed is at least part of the region of elasticity.

15. A computing device as in claim 14 wherein operational step (d) comprises calculating elastic strain energy release within a portion of the region of elasticity whose lower and upper boundaries lie along a boundary of the region of elasticity and whose left and right boundaries within the advance of the crack, the portion of the region of elasticity excluding any regions of plasticity in the material.

16. A computing device as in claim 14 wherein:

the material comprises a first material region and a second material region, the first material region containing at least part of the crack, the first and second material regions having a material interface therebetween; and the information includes physical information regarding the first material region and the second material region and geometrical information regarding the material interface.

17. A computing device as in claim 16 wherein:

the material interface is one of an elliptical and a planar surface; and the geometrical information regarding the material interface comprises an identification of whether the boundary is the elliptical interface or the planar interface and an initial location of the crack tip relative to the material interface.

18. A computing device as in claim 17 wherein operational step (d) comprises determining regions of overlap between the region of elasticity and the first and second material regions.

19. A computing device as in claim 18 wherein when the material interface is the elliptical interface, the step of determining regions of overlap comprises determining points of intersection between a circle bounding the region of elasticity and the elliptical interface by a Newton-Raphson method which is performed in accordance with equations representing the elliptical interface and the circle bounding the region of elasticity.

20. A computing device as in claim 19 wherein the Newton-Raphson method comprises a probabilistic method performed in accordance with test variables entered in step (b) and a probability of finding one of the points of intersection on any particular portion of the elliptical interface.

21. A computing device comprising:

a processor:

input means for receiving input from a user; and output means for displaying an output to the user;

the processor comprising:

means for prompting the user, with the output means, for information regarding material having a crack therein;

means for receiving the information from the user with the input means;

means for selecting an increment of crack advance; and means for integrating numerically over a region surrounding a tip of the crack in accordance with the information and the selected increment of crack advance to determine an energy change in the region caused by an advance of the crack by the increment of crack advance.

22. A computing device as in claim 21, wherein the processor comprises:

means for incrementing the crack advance for a number i of successive advances of the crack in accordance with the succession of energy changes;

means for deriving a graph of net energy change per unit length of advance of the crack in accordance with the succession of energy changes; and means for displaying the graph on the output means.

23. A computing device as in claim 22 wherein:

the increment of crack advance has a value $\Delta\xi$;

the means for incrementing is operated i times;

the information received from the user comprises a minimum crack length $\xi_{min}$ and a maximum crack length $\xi_{max}$; and the processor further comprises means for calculating $\Delta\xi$ as $(\xi_{max}-\xi_{min})/i$.

24. A computing device as in claim 21 wherein:

the information comprises a radius of elasticity selected by the user;

a circular region within the radius of elasticity of the tip of the crack is defined as the region of elasticity; and the region surrounding the tip of the crack in which the means for integrating numerically operates is at least part of the region of elasticity.

25. A computing device as in claim 24 wherein the means for integrating numerically comprises means for calculating elastic strain energy release within a portion of the region of elasticity whose lower and upper boundaries lie along a boundary of the region of elasticity and whose left and right boundaries lie within the advance of the crack, the portion of the region of elasticity excluding any regions of plasticity in the material.

26. A computing device as in claim 24 wherein:

the material comprises a first material region and a second material region, the first material region containing at least part of the crack, the first and second material regions having a material interface therebetween; and the information includes physical information regarding the first material region and the second material region and geometrical information regarding the material interface.

27. A computing device as in claim 26 wherein:

the material interface is one of an elliptical interface and a planar interface; and the geometrical information regarding the material interface comprises an identification of whether the boundary is the elliptical interface or the planar interface and an initial location of the crack tip relative to the material interface.

28. A computing device as in claim 27 wherein the means for integrating numerically comprises means for determining regions of overlap between the region of elasticity and the first and second material regions.

29. A computing device as in claim 28 wherein the means for determining regions of overlap comprises means for determining, when the material interface is the elliptical interface, points of intersection between a circle bounding the region of elasticity and the elliptical interface.

30. A computing device as in claim 29 wherein the means for determining points of intersection comprises means for performing a Newton-Raphson method in accordance with equations representing the elliptical interface and the circle bounding the region of elasticity.

31. A computing device as in claim 29, wherein the means for determining points of intersection comprises means for performing a probabilistic method, responsive to the information received by the input means, for determining a probability of finding one of the points of intersection on any particular portion of the elliptical interface.

32. A computer-readable storage medium in which a data structure is written regarding calculations of advance of a crack in a material performed with a plurality of programs, the data structure having a form of a two-dimensional array, a first dimension of the two-dimensional array representing an increment of the advance of the crack, and a second dimension of the two dimensional array representing one of the plurality of programs.

33. A series of operational steps to be performed on or by means of a computing device to determine a spatial relationship between (i) at least one region of integration surrounding a crack tip which is in a first material region in a material and (ii) first and second boundaries between the first material region and a second material region in the material, the first boundary being closer to the crack tip than the second boundary, the computing device comprising a processor, an input, and an output, the series of operational steps comprising:
  (a) prompting the user, by means of the output, to enter data comprising material characteristics of portions of the material within the first and second material regions, a thickness d of the second material region, a distance $\xi$ of the crack tip to the first boundary along a crack path, a radius b around the crack tip in which energy release caused by the crack is to be calculated, and an angle $\psi$ representing an orientation of the crack path with respect to the first boundary;
  (b) receiving the data from the user by means of the input;
  (c) calculating, in accordance with the data received in step (b), a shortest distance r1 from the crack tip to the first boundary and a shortest distance r2 from the crack tip to the second boundary;
  (d) calculating, in accordance with the material characteristics received in step (b), a radius of plasticity rpl1 of the portion of the material within the first material region and a radius of plasticity rpl2 of the portion of the material within the second material region, wherein the radii b, rpl1, and rpl2 define the at least one region of integration;
  (e) determining whether b<r1 or b>r1;
  (f) if b<r1, determining whether r1<rpl2 or r1>rpl2;
  (g) if b>r1, determining whether r2<rpl2 or r2>rpl2; and
  (h) determining the spatial relationship in accordance with results of the determining steps in steps (e)–(g).

34. A series of operational steps as in claim 33, wherein:
  in a direction perpendicular to the direction of the crack path, the crack tip is separated from the first boundary by a distance ord1;
  the energy release is calculated through a numerical integration performed within limits of integration selected from –b, b, –rpl1, rpl1, and ord1; and
  the series of operational steps further comprises:
    (i) calculating ord1 and rpl1 in accordance with the data received in step (b); and
    (j) selecting the limits of integration in accordance with the spatial relationship determined in step (h).

35. A series of operational steps to be performed on or by means of a computing device for locating an intersection point between an ellipse and another curve, the operational steps comprising:
  (a) dividing the ellipse into a plurality of regions, each of the regions being defined by four values boundleft, boundright, boundlower, and boundupper such that said each of the regions of the ellipse consists of points whose x coordinates lie between boundleft and boundright and whose y coordinates lie between boundlower and boundupper;
  (b) determining, by numerical approximation, a numerically approximated intersection point between the ellipse and said another curve, the numerically approximated intersection point having coordinates NRx and NRy; and
  (c) for each one of the plurality of regions:
    (i) determining whether boundleft≦NRx≦boundright;
    (ii) determining whether boundlower≦NRy≦boundupper;
    (iii) if both of determining steps (c)(i) and (c)(ii) yield affirmative answers, locating the intersection point within that one of the plurality of regions and assigning NRx and NRy as coordinates of the intersection point; and
    (iv) if at least one of determining steps (c)(i) and (c)(ii) yields a negative answer, determining that the intersection point lies outside that one of the plurality of regions;
  so that the intersection point is uniquely located in only one of the plurality of regions.

36. A series of operational steps as in claim 35, wherein the numerical approximation in step (b) is carried out by a Newton-Raphson method.

37. A series of operational steps as in claim 35, further comprising:
  (d) ranking the plurality of regions in order of likelihood that the intersection point is found in each of the plurality of regions, from a region of lowest probability to a region of highest probability;
  (e) defining trial coordinates trialxreg and trialyreg for the intersection point and initially setting trialxreg=0 and trialyreg=0;
  (f) for each of the plurality of regions in the order of likelihood:
    (i) determining whether the intersection point has been located in said each of the plurality of regions in step (c)(iii); and
    (ii) if so, setting trialxreg=NRx and trialyreg=NRy;
  so that the intersection point is located in a most likely one of the plurality of regions.

38. A series of operational steps as in claim 37, wherein:
  the ellipse and said another curve have a plurality of intersection points, each with its own values of NRx and NRy; and
  steps (d)–(f) are performed for each of the plurality of intersection points;
  so that said each of the intersection points is located in a most likely one of the plurality of regions for that one of the intersection points.

39. A series of operational steps as in claim 38, wherein:
  the ellipse and said another curve bound a closed area in which numerical integration is to take place;
  the ellipse has a left side and a right side which are defined with reference to a center of the ellipse; and
  the series of operational steps further comprises:
    (g) determining a number of regions of the numerical integration in accordance with positions of the plurality of intersection points on the left side or the right side of the ellipse.

40. A series of operational steps as in claim 39, wherein the number of regions of the numerical integration is further determined in accordance with relative dimensions of the ellipse and said another curve.

* * * * *